US005705343A

United States Patent [19]
Drayna et al.

[11] Patent Number: 5,705,343
[45] Date of Patent: Jan. 6, 1998

[54] METHOD TO DIAGNOSE HEREDITARY HEMOCHROMATOSIS

[75] Inventors: Dennis T. Drayna, San Mateo; John N. Feder, Mount View; Andreas Gnirke, San Carlos; Bruce E. Kimmel; Winston J. Thomas, both of San Mateo; Roger K. Wolff, Belmont, all of Calif.

[73] Assignee: Mercator Genetics, Inc., Menlo Park, Calif.

[21] Appl. No.: 599,252

[22] Filed: Feb. 9, 1996

Related U.S. Application Data

[63] Continuation-in-part of Ser. No. 559,302, Nov. 15, 1995, which is a continuation-in-part of Ser. No. 436,074, May 8, 1995.

[51] Int. Cl.$^6$ .............................. C12Q 1/68; C12P 19/34; C07H 21/04; C12N 15/00
[52] U.S. Cl. .......................... 435/6; 435/91.1; 435/91.2; 435/810; 536/23.1; 536/23.5; 536/24.3; 536/24.31; 536/24.33; 935/8; 935/9; 935/10; 935/77; 935/78
[58] Field of Search ........................ 435/6, 91.1, 91.2, 435/183, 7.1, 7.4, 70.2, 810, 960; 436/94; 536/23.1, 23.5, 24.3, 24.31, 24.33; 935/8, 9, 10, 77, 78

[56] References Cited

PUBLICATIONS

Jazwinska, E.C. et al., "Localization of the hemochromatosis Gene Close to D6S105," *Am. J. Hum. Genet.* (1993) 53:347–352.

Worwood, M. et al., "Alleles at D6S265 and D6S105 define a haemochromatosis–specific genotype," *British Journal of Haematology* (1994) 86:863–866.

Jazwinska, E.C. et al., "Haplotype Analysis in Australian Hemochromatosis Patients: Evidence for a Predominant Ancestral Haplotype Exclusively Associated with Hemochromatosis," *Am. J. Hum. Genet.* (1995) 56:428–433.

Finch, C.A., "Hemochromatosis—Treatment Is Easy, Diagnosis Hard," *The Western Journal of Medicine* (Sep. 1990) 153(3):323–325.

"Hemochromatosis [HFE]," *Autosomal Recessive Catalog*, Art. No. 235200, pp. 1882–1887.

Cartwright, G.E. et al., "Inheritance of Hemochromatosis: Linkage to HLA," *Hereditary Hemochromatosis*, pp. 273–281.

Lipinski, M. et al., "Idiopathic Hemochromatosis: Linkage with HLA," *Tissue Antigens* (1978) 11:471–474.

Simon, M. et al., "A Study of 609 HLA Haplotypes Marking for the Hemochromatosis Gene: (1) Mapping of the Gene near the HLA0A Locus and Characters Required to Define a Heterozygous Population and (2) Hypothesis Concerning the Underlying Cause of Hemochromatosis–HLA Association," *Am. J. Hum. Genet.* (1987) 41:89–105.

Summers, K.M. et al., "HLA Determinants in an Australian Population of Hemochromatosis Patients and Their Families," *Am. J. Hum. Genet.* (1989) 45:41–48.

"Report of a Joint WHO/Hemochromatosis Foundation/French Hemochromatosis Association Meeting on the Prevention and control of Hemochromatosis," Hereditary Disease Programme, WHO/HDP/HF/FHA/93.2, Kiryat Anavim, Israel, 27 Apr. 1993.

Gyapay, G., et al., "The 1993–94 Genethon Human Genetic Linkage Map", *Nature Genetics*, vol. 7, pp. 246–339, Jun. 1994.

Stone, C., et al., "Isolation of CA Dinucleotide Repeats Close to D6S105; Linkage Disequilibrium with Haemochromatosis", *Human Molecular Genetics*, vol. 3, No. 11, pp. 2043–2046, Nov. 1994.

Pearson, W.R., et al., "Improved Tools for Biological Sequence Comparison", *Proc. Natl. Acad. Sci. USA*, vol. 85, pp. 2444–2448, Apr. 1998.

Niederau, C., et al., "Disease Associations: Which Factors Determine the Development of Liver Cancer in Hereditary Hemochromatosis?", *Cancer Biotechnology Weekly*, p. 415, 11 Mar. 1996.

Piperno, A., et al., "Liver Damage in Italian Patients with Hereditary Hemochromatosis is Highly Influenced by Hepatitis B and C Virus Infection", *Journal of Hepatology*, vol. 16, No. 3, pp. 364–368, 1992.

Rubin, R.B., et al., "Iron and Chronic Viral Hepatitis: Emerging Evidence for an Important Interaction", *Digestive Diseases*, vol. 13, No. 4, pp. 223–238, Jul. 1995.

Arber, N., et al., "Elevated Serum Iron Predicts Poor Response to Interferon Treatment in Patients with Chronic HCV Infection", *Digestive Diseases and Sciences*, vol. 40, No. 11, pp. 2431–2433, Nov. 1995.

Wilbur, W.J., et al., "Rapid Similarity Searches of Nucleic Acid and Protein Data Banks", *Proc. Natl., Acad. Sci. USA*, vol. 80, pp. 726–730, Feb. 1983.

Beutler, E., et al., "A Strategy for Cloning the Hereditary Hemochromatosis Gene", *Blood Cells, Molecules, and Diseases*, vol. 21, No. 21, pp. 207–216, 15 Nov. 1995.

Burt, M.J., et al., "A 4.5–Megabase YAC Contig and Physical Map Over the Hemochromatosis Gene Region", *Genomics*, vol. 33, pp. 153–158, Feb. 1996.

Totaro, A., et al., "Hereditary Hemochromatosis: Generation of a Transcription Map Within a Refined and Extended Map of the HLA Class I Region", *Genomics*, vol. 31, pp. 319–326, 1996.

Calandro, L.M., et al., "Characterization of a Recombinant That Locates the Hereditary Hemochromatosis Gene Telomeric to HLA–F", *Human Genetics*, vol. 96, pp. 339–342, 1995.

(List continued on next page.)

*Primary Examiner*—Bradley L. Sisson
*Attorney, Agent, or Firm*—Townsend and Townsend and Crew LLP

[57] ABSTRACT

New genetic markers for the presence of a mutation in the common hereditary hemochromatosis (HH) gene are disclosed. The multiplicity of markers permits definition of genotypes characteristic of carriers and homozygotes containing this mutation in their genomic DNA.

13 Claims, 24 Drawing Sheets

OTHER PUBLICATIONS

Gasparini, P., et al., "Linkage Analysis of 6p21 Polymorphic Markers and the Hereditary Hemochromatosis: Localization of the Gene Centromeric to HLA–F", *Human Molecular Genetics*, vol. 2, No. 5, pp. 571–576, May 1993.

Totaro, A., et al., "New Markers and Polymorphisms in the Hereditary Hemochromatosis (HFE) Gene Region", *Miami Biotechnology Short Report: Conference Proceedings Mol. Biol. Hum. Diseases*, vol. 5, p. 53, Nov. 1994.

Totaro, A., et al., "New Polymorphisms and Markers in the HLA Class I Region: Relevance to Hereditary Hemochromatosis (HFE)", *Human Genetics*, vol. 95, No. 4, pp. 429–434, Apr. 1995.

Yaouang, J., et al., "Anonymous Marker Loci Within 400 kb of HLA–A Generate Haplotypes in Linkage Disequilibrium with the Hemochromatosis Gene (HFE)", *Am. J. Hum. Genet.*, vol. 54, pp. 252–263, 1994.

1260 bp around the polymorphism 18B4

```
AGCTATACTA AAATTCTTCA GCTTTCATTT TTGGGCCCAT GCTTAGTATT GTTAAAAACT
TATTTGTAGA ACATTCATGT TTTTGATATA AATTGTATGA ATACAATTTA TTTCAAAACA
TTTCCTTTGG CTGAAAACGC CATAGCCTTA AGAAAACTTT ATTAAAAAGA CAAAGTCTTT
CAGACATTTG CAAAAATGCA TCAGTAATAA CCCTAATTCA TCACACTGGA TAAAATTTCT
ATCTGGTTAA GATTTCATCA CTTCAAGCTA AAGCGGAAGA AGGAGGTTTT TATATTGATA
TTGGAAAAGT CCTTGATTGT ATTGGATGCC ATTATTCTTA TCTCTAAACA TGAACTGATG
TCACCATTTC TTTATATCAG TCTCAGTTTT GATAACAAAT TGACTCTCTT AAACTTCTTA
AGCAGATTGA TAATTCATGC ACTTCCTTGT ATCCAGTGAC TCTAATCTTA AACAAATGGA
ACATAAAATA CTGAACCAAT TAGCAAAATG AACTGTTTCT TAAACGTTTA TAACAATCTA
TGGATCTTAT TGTGCCTAAA TAGATTAATC ATTTTAATTT TTTTAAAAAT TTAAAATTTC
TCTAAAGTTT TCTTTTGCTT TCTAGATACA CAAATTACAC ACACACACAC ACACACACAC
ACAAACACAC ACACAGTGGC AATTAAATAT TCGTGCCTTG AAAAGTGAGA AAGGATACAG
ATGTCCTTCT GCCTAGTAGA CCTGTTTATG AGAGGTCCTG TAGACTCCCT GTACTCACTT
GACTCCCAAA TTCATTACCT CTATCAACCC AAATATGCTC CTTTTCCTTC TGTGTATCTA
CTTCATTAAA CATCTGTGCA ATCAGCCAGA CACAAACTTG CAGACCCCGC CTCACCACTC
TCCTGCCTCT TATCTGATAA ATCTCCAGT GCCGCAAATT CTCCCTCTAG CCCGGCTTGT
TCATCTGTAC ACTTGCCTTT ATTACAGCTC TCATACCATA GCAGATCACC ACTGCTTTTC
TCCTAGATTA CTGCAGCCAT CTCCTGTTTG TCTCTCATTT TCCAGTATCA CTCTCTTCTA
ATTTGCTGCA GCTGGAGTTA GGTTCTAAAT TCCAAATTCA TTCATGTATC TACTTTAAAT
AACTCAGTAC TTCTTTTTTG TTTGTTTGTT TTTCATAATG ACAAAACTCC TTAACATGAG
CTACAAGATC ATGCATATTC TGGTCCCTAT TCCTTAACTA GTCAGAGTGA ATGTCATTCC
```

Figure 1A 1260 bp around polymorphism 19D9

```
GTAATAAAAT TATTTAGGGT TTTGGATTGT GTCAAAGCCC TATTCAGCAA TGTCTACTTG
AAAATTTCAT TGAAAAAGTA ACTTAAATAA AGTAGCTATT TGAAGGGCTC AGTAGGATAG
AACCCTTGTC CTTAGCATGA ATCATAGTGA GAAGACACTT TTGAATATGT TTGTTTTTCT
TCTATTACCA GGAAAACATA GGATCATAAA TCACAATTAT TCCATATGTT TTAGAAATTA
ATCATGTGTA TCTTTGCACA AGCACCATAA TGCTTGTGTG TATAAATGAG TATGCATGCA
TACTTGTAAA CACACAGCTT TCATACTCGC TTTTATTATT GTCACTTTTA ACAGCCCCTT
ACATGAAATT TATATTTAAA AAGTGAGAAC ATTTATATTC ATTCTGATGT ATTCAGACAC
TTGTATTAAA TTCTTAGCTC TACTATTTGT GGTCTGTTTG ATAATGTTTC CTAATCTATC
AAATGAAAGG ATTCTGAATT GATCATTTGT TTTCAAATGT ATATTCATGT TAGAATCTCA
CAAGGAGCTT TTTCAACAAA ATATTCCAG  ACTTTCAAAA ACTCACAATC ACTGTGGTTG
GAACTTGAAA CAAACATATG TGTGTCTGTG TGTGTATATA TATATATATA CACACACACA
GACACACATA TATATATCTT TATGTAATTT TAATGCAGCT GATCAGTGAA ACAGTGTTAA
GCTCAAAAAT TTTAATGATG TCATTTCCA  TGTCTTCACT AACCTTCTCT CTTCTCCTTT
TCTCTCTTTT CCTTCCTACC AAATTTTTC  CTACCTATTT TTACTCTCCA TTTTCTCACT
CCCCTTTAAC TCATTTCCAT TACACAAACT ACTATTACAC AAACTACTCA TATAATTTTT
CCTCATCTTA TCTTCCCAAA GCATAACTTC TGTCAGTCAA TCCACAGTAC TAAAGCATTG
ATTTATGGTT CTGTTGGATT TTAATTAGCT GTGGTCAATT TGGAAAGGAG GAGAAAAAAT
GATTTGACAT GTCAGATACA ACATGTTATA CAGATTAAAT TTCAGCTGTA ATCTAACTAG
TCATCAGCAT TTTATTCAGG GCTTTACAAT AAGTATTCCC AAGTTCTGCC TCTGTAGGTT
TGTATTGGGT AGGTAGGAAT ATTTAAATGA ATTTTGAAGT TTCACTTCAA GAATTATTTA
TTTCTATTAA ATAAGTAAAG AAGCAGTCTC AAGAGCAGTC ACTGTCACTG TGTTTTCTAG
```

Figure 1B

Approximately 1 kb of sequence around the polymorphism 1A2

TTGTTCTGTG CCTTAGCTTT ATTTCCAAAG TTCCAGAAAA GACAAGTCAC AGATCGGGAG

AAAATATTTG CAAAACATAT ATACCATGAC CCATGAGGCC CCTCCTCTGC CACTGCCACT

GCCACTGCCA CTGAGATGGT GTATCTCACT TCCTACCTAT TACCTTCCCT CATGAGCAAC

ACCTCCCTTA GTGCCAAGGA CATTAAGAAG ATCCTGGACA GAGTAGGCAT GGAGGCAACT

GATGACTGGC TAAACAAGGT TATCAGTGAG CTGAATGGAA AAAATATTGA AGATATCATT

GCCCAAGGTA TTGGTGAGCT TGCCAGTGTG CCTGCTGGTG GGCTGTGGC CCTCTCTGCT

TCTCTGGGCT CTGCAGGTCC TGCTGCTGGT TCTACCCCTG CTGCAGAAGA AAGATGACAA

GAAGGAGGAG TCATCTGAAG AGTTGGCCTG TTCAATTAAA TTCCTGGTGT CCTACAAACA

AAGCCTTTTC ACATTAAAAA AAAACAAACA AACCA<u>GTGTG TGTGTGTGTG TGTGTGTGTG</u>

<u>TGTGTGT</u>AAT AGAGGCTTTG TATTCAAAAT ATACAAAGAA CTCCAAAGTT CAACAATAAG

AAAACATGTA AACCAATTAA AAAATGGGCA AAATATCTGA ACTGACACCT TAACAAAGAA

GACATGCAAA TGGCAAATAA GCATGTAAAA AGATAGTCAA TGTCATTTTT TATTAGGAAA

TTGCAAACCA GAAAACAGGG AGATACCACT ACATTCTTAT TAGAATGGAC TAAAATCTAA

AAAATCGACA ATACCAATTG CTAGCAAGGA TGCGGAGTGG CAGAAAGTCT CATTTATTTC

TTGTGAGATG CAGAAGAGTA CATCAATTTC CTGATCACTG CAATTCATTC CATGACCCAC

ATAGATATTT TTCTCCCCAT ATGTTAGGGA AGCAGATCTC TCATGGTCTT CATGGACTTC

TCTTTCTGAG TGGAAATTCA CAAGGGTATC TTCTAGTTAT CTATTCCAAT CTCCCCCACC

CTCATCTAGC ATCTTGAAGG GTCTTGGTTG

Figure 1C

Approximately 1380bp around polymorphism 1E4

```
CTGTAAAGTT ACCATTTTTC CTTTTTAAAT TAATAATTAT CTTGAGAGGG AATATTTTGA
GATTATGAAA ATATTCTGTT TCTCATCATA TTTTTGCTAC TTATATTGAT GTTCATCAGT
GATTCTTGCC TGCAACAATT ATTTCTGTAG CATCTATTTT CTATTTCTAT TGCTAATTCT
ACATTTATTA ATTGGAATTC TACTGTAAAG AAGAGCTGTT ATTTTTCCCC CATTTGTTAT
TTGTTCAGTC ATTTATTTAA ACTCATATAG ACTTATGGGT ATTTGTTTTA TTCTATTGTT
TGTAGTCCCA ATACTATCAT TATTTAATTT ACTGCTAAAA TTGTCCTAGA TTTGGCCTTT
GGGAGCTCCT TCAAGTTGAC TCATGTATCT TTTTAACATG CCCCATCACT ATTTGAGAAC
TTCTATACTC TGTGTCACCA CCAGCTGTTC TAGGGTCATC TTGGACTTTT ACTTCCCCAG
CCCTGGAATT ACTAATTTTT CTAAGGATCC TTGGTTCCTT TTACTGGAAA TATATTTAGA
AATCAAGTTC TAGGCACCAG GTGTGTTCAT TGCTACTGAT TGTTATTGC TTCCAGACTC
TCTCAGTGAA CAGAGCTTAC AAATAGAGTG TGTGTGTGTG TATATATATA TATATATATA
TATATATATA TACTGACATA TACATACACA TACATTTTA TTTATATACC TAGCTGTGTG
TGTGTATGTG TGTGTGTGTG ACCACAGTTC ATACTAATGC CTCTGATTCC AATCCAAATA
CCACATAGTA TTTGCATAAA CTCCCTCCAT TCCTTATTTG TACCTTCTTT GTTGAACAGT
GGGAAATTTG GCTCTCATTA TCCATAATAT ATTTACTTAT TTTCTCAATT CTAATACACA
AATAGCTTTA GAATTGCTAA TCCACACTCT TGGGAATAAC CATTTTACTA ACTAGAGTAC
AATATTTCTG TACAGTTCTT TTTGCTTTTA TCCTTAGATG AGTCTATCCT TAGCAAAATA
GTCAAGATAC TCTTTTTCCC AAAGTTAATT AGGTTAGTTT TTTTTCCTTC CTTACCCTCT
TTAACTTGGT TTTGTTGCTC ATTTGTAATA CAGGTGGGTT AATTTATTAT TCTCTGTATT
TCTTTTGGGT ACCTCCCATT CCGGTTGACT TTAGTTATTT ATTTAAATTG GAATATGTGA
AGCATTACTA TGGCTATAAA AGTTAGAACA CACAAAATGT TATATGTACT TAGAAAAGTG
TCACTCCCCC TCAGCCTTTC CATTCCACTA ATTCTCCCAT TTTTTTATAC TCTATTCCAA
ATCACCACCT CCTCCAACCC TGTGGGTAAC TAATCTCATT AGTTCTGGT TTATCATTCC
```

Figure 1D 1260 bp around the polymorphism 24E2

```
CCCAGAATTG GCCTTCCAAT GCACCAAAAA CTGTAATCAC AACATTTTCA AGGGTTGTCA
CACTTTACAT CAATGTTTGT ACAATTCAGT GTAAACTAGA CCTTTCTGAT CCAGAAATCA
TCTCTTCAGT AATACACACA CGCACACACA CATACATACA TACACACACA CACATAGAAA
CCAAGATGTA AAGGGAGCTT TTGAGAGGTT GCTTGCAAGG GTGTTAATAA AAAAAAAGG
AATTCTCAAA TTATAGGCCT TTTAAAGACT TCAATTTTAC ATAGCTTATA ATTTAATTCT
CTCCAAATTG CTTTATTATT ACTATTCTTA GAAAAACTAT TATAGTGATC TTCAAATAAA
ATGTCGACAG AGAACTATAT CTGTTTTCTA CTGCCTAAAT ATATTCATTG CACAAGTCTT
AAGAACTGAT CTTTTATGAA CTCTCAAAAT AGCATATCCT TGAAATCTTT AAGGTCTCAA
ACATCTTAGC ACTAGTCTGT ATACATCGGG AAGAGACTTA GACTTCTCTG AAACCAGAAT
AAAAGCCAGA AACAAAACAT TTGATACAT ATACACATGT CCTCATCCTT ACACACACAC
ACACACACAC ACACACACAC ACAAACTCCA TGGCACAAAT TATTTTTCAG ACAATTGTAG
ATCTAACAGA AGTATCCAAA ACCTTGTCTT AATTTTCTCT ATAAGTTTAA CAGCCCTAGC
TTAAATTTTA ACACTATTCG CACATCAACA CAATACTAAA ATCCACAACA ATTCTGCACT
CCCCAGTTTT ACTTAGATCT TCTGTTGTTT CTGTACTTCC CACTTCTAAG TTGAAGTGTC
CTATTCCATC TATCAAATAA AGTTGTAGCT ACATTTAGA CTGAAATCGA ATGCCTGCTT
TTGACCTTTT AAAATGATTC CTCTACTGTA TATATTATCT CTCTCCTTTT AACCTCGAAA
GCACTTATAG GGGCCGGGCG CGGTGGCTTA TGCCTGTAAT CCTAGCACTT TGGGAGGCCG
AGGCAGGCGG ATTGCCTGAG GTTAGGAGTT CAAGACCAGC CTGGGCAACA ATGGTGAAAC
CCTGTCTCTA CTAAAATACA AAAATTAGCC AGGCATGACC GCGTGCGCCT GTAGTCCCAG
CTACTTGGGA GGCTGAGGCA GGAGAATCGC TTGAACCCAG GAGGCGGAGG TTGCGGTGAG
CTGAGGTCAC GCCATTGCAC TCCAGCCTGG GCAACAGAGC GAGACTCCAT CTCAAAAAAA
```

Figure 1E

Approximately 1kb of sequence around the polymorphism 2B8

```
AGCTTTCTTT TGCCATTAAC AAGTAATAAC AAGGATTGAG TAGTAACAAG AAATTCTTCC
TTCCACATAA AGCAAACACC TCATGGTCTT GCTTTATCTC CTTTCTTCTT GATTCTCTAT
CATCTCAGAA AATCAAACAT GAATGTCATT AAGCTCAATT ATATAAATGA TTCAAAATGT
GCAGAATCCA CGGTTGATTA TGGTGTTGGA TATACTAAAG CTGGATAATT AAACAATTTA
TTTTGGCTCT CATTCAAGCA TTTGGCACTA TAAAAGCATA TTTGAACTTT CTAGAAAAAA
ATAAGTGCTT CTTCAGCAAG ACTTCGAAGA TCTTTCGTTT CATATATTGC TGAGGACCTA
CTAAGTCCTT CTAAGATCTT TCTTTTCATA CATCGTTGAG GACCTATTAA ATAACTGTGA
TAGAAACTGG TATGAGAACA AAAATGCCTA GTGTCTACAT TCACGAACAA TATTTTGGAG
GCTTCTGGTG ATGAATGCTT GATTTAGAAG GACTTGAAAG GAATACAAGT GATTGTCAAC
TCAGGAGGAA TATTACATTT TTTACACTCT TGCTTTCTTT CTTTCTTTCC TCTTTCTTTC
TTTCTTTCTT TCTTTCTTTC TTTCTTTCCT CTTTCTTCTC TCTCTCTCTC TCTCTCTCTC
TCTCTCTCTG ACAGGGTCTT GCTCTGTCAC CCAGACTGAG TGCAGTGGCA CAAACACGGC
TCACTGTAGC TTCAAATTCC CAGGCTCAAG CAATCCTCCC ACCTCAGCCT TCTGAGTAGC
TGGGACTGTA GGCATGCACC ACCATGCCTG GCTAACTTTT TAAATTTTTC GTACAGATGG
GGGTCTCACT ATGTTGCTCA GGCTAGTCTC AAACTCCTGG ACTCAAGCAA TACTCCCACC
TCCCAAAGTG CTGGGATTAC AGGCAGGAGC CACTGCTCCT AGCCCTATT TTCTTGACCT
AGCTAAACCA TTGAATTCCC CCATCTCATT AAATGCCTCT TCAGCCTGCA ATGCCAAAAC
ATTCCTATAT TTGCTAGGTC TAACAACATA TATAGAAGAT GGGTCAAAAT ACAATCCCAA
AGTTTAATCA CCCCTTACTA TATTTCTGCA CTCCCCTTCC CTAGCACCTT CTTCATGGCC
TCTTTAACAT CTTTGTTTCT TAGTGTATAG ATCAGGGGGT TAACACTGGG AGTGACAATT
GTGTAGAAAA GGGTAAGAAA CTTGCCCTGG TCCTGGGAAT AAGTATTTGC TGGCTGGAGG
TACATGTATA TGATTGTACC ATAGAAGAGA GAGACAACAA TTAGATGCGA GCTGCAAGTG
```

Figure 1F 731-1

AATTAAGTTA AAGTTGAGGC GGCTCAGTGT GAGGAGAAAG CCCATCATTC AGAATACAGG
GACACCCCTG CCCAGGTGCC ATGACCTGAA TGCACTANGG GACAGGCACC AAGGAAGGCT
CTGGCAGGGT GCGACCCAGA GGGGTTTTGG GATCCACCAT CATGGAGATG CCCTTCCCTT
CATGTGAGGT GGGGTTTCTG CTCTCACTCT GCCTTCAGAG GTCCTACATG AGAACTACTG
GGTGGCAGGG GAATAAAGGA GAATTAAGGA GAAAAGAGTT AACAATGCA TGCCTATCTT
AGAGGAGAGA GGCTATGAAG GAGGCCTAGA GTCTTGCGGC CAGCTCCTGC TTTCTTTAAA
ACTTTCAGGA AGGGAAGGG ATAGATGTCA CAACTTCTCG GGATTGCTTT TTTAGGGACA
CAGGATAGTC TGATTCATCT ACCCTAAAAT ATGATTTTCC TTTGGAATAG ATATTTCAGG
ATCAGAGAGT TGGAGAGATA GGTGTTCTTT TCCTTAATCT TCAA<u>ACACAC ACACACACAC
ACACACACAC A</u>CCATACATA CACCTATGCA TATACCAACA AATACAATTC TACATATCCA
TACACACACA CACACACACA CACACAGCTC CACACACATG CTAAGCAGGT GCTTGGGTAG
TACAGGATGG TTTGGTCATC AGGAGGCTGG GTAGGCACGA GTGTGGAGCA AAGAAGGAGG
AAGATGGATG CTTTGTTAGA CATTCCTGCA G

Figure 1G 5091-1

TAATTTAGAT TCTTTTTACT CTCTTCTATT CGCAAATATA GCAAATTATG AAAATAATTC

TGCACCTTGC CTTTCTCCCT TAGTTATAGC TGGAAAAATA AAAATTTAAA AGCCTCTTTA

ATAGCAAAAG GGGAGGGGAC ACAAGGTGCC GAGCTAGCAA ACGACAGAGT CTGTCAGGGA

GGTGGCTAGA GAGGCCCGGA AGTGGCTTCT GTGCCCCGCC CTGCGGGTGG TTTGCTAGTT

TCAAGCACTT TGTGAGTATG GGGTGAATCG GCGTCGGCCT TCCACTGTGG GGTTAAATCT

CATCCCGCGG CTCTCCTCCT GTCGGTCCTG CAGTTCTTTT GTCCCCGGGT AGAGGTGCGT

TTGCAGGAGT A<u>TGTGTGTGT GTGTGTGTGT GTGTGTGTGT GTGTGTG</u>TTT GTGGAGAGAG

GCCCTTCCCT CCCCAGTTCC TGCAGCCTCG GCTCCCAAGG AGGGAGACCC CTGCGAGAAG

CCGTGGGGGA GGGAAGGGCG CTCTGGGCGG AATGAAGTGG TCCTCGGCGT TCCTGCGTAG

AGCCC

ACGTAAAGGT ATTTAACTAA AAGTGTCTTC CTATAATTTC TGTTAAAGTC GNAACACATG

CCTATGTNGT ATTTCTTTGA CATATGCTGT TATTTCTNCA CTTTTTCCTG TCATTTATAG

AGCCTTTCTA TATATGTGAG ATCAAGATTT NACATTTGN<u>G TGTGTGTGTG TGTGTGTGTG

TGT</u>AAGGGGC TGGGAAATAT AGAGAATATT GTGAGGTNNG GGATTCTNCA GAAAAATCAT

CTCTCACTGC AACAGAGTAC TATTGNNGAA AGANTCCCAT TCTACTGTTA TCTAGA

TTATACCAGA ACTGCATCTA TTACAGCATA AACCAATTAT ATCTTTGACC AGAACCTATA

CTTTACTAAT AGCGGTACTG TCACCTATTT CTGAGAGTGT ATCAAGCTGG AGCAGGAGCA

TGGAAAATAA AACAGAGCTG GAGCTTGAAT TGACACTGAC ATCATCCCTA CCTTAGAAGA

CAAATATATG TATGTGTNTA CACACACACA CACACACACA CACACAGAGN AGAGNCACAG

ATATAGTCAA TCTGAATACT TNGGTAAATT TGTCCTGGAG AGAAAACTTA TCAGACAG

Figure 1J 4073-1
>2          00005

CTGTCATCTC TGTCCTGAGG CCCTGCCTCA CCATTCCCTC AAGGCCCAGA CCATCATCAA

GGCCCTGGCC ACCCAGCCAC TGATGCATAT GGCCTTTTCT TTCTCTCATG CAGCCTCTTC

TCCCTGGGGC AGAGGTTGTG GGGAGGGAGG TGGTGTGTGT GTGTGTGTGT GTGTGTGTGT

GTGTGTGTGT GGTTTGCTGT CCAGTTTTAA AGGATTCCAA GCCATGTGAA ACTNCCTCAC

TAGATGTGAT CTGGTTGCGG CAAGTGCTTA TTACNGAGTG AGGCTGGGGA ATGGGCTGGG

GGTATTAGCA GTCCTTTTGC AGTGTGTGTG GTGGGGTCAC ACCACTATGG CTAAGCCTAA

GACACTCCCA GAGAGAAGTA CTGCAGAAGG AACTGGTTTC CGGACTGCAG AGGGATCTGC

ATTTTGGNTT TTGACCACCC CCACCAAAAA AATAGGTTAG ATCTGAAGGG CAAAGGGAAT

ACCCAAGCCT CTGATGCCTA TGAGAAGTCC CTGGACTTCG ACCCTTCTGA TGTGTGATGT

TAGCCCCGNG GGGAGCTGCT CACCTGAGCA CCTTTGGGGG TGAGAAGGGA GCAGGGAGGT

AGGGT

Figure 1K 3321-1
>RV1          00006

```
GATATCCACT CTCTATACAC TATGTATATT TTTTGGTTTA TTGCCTGCCT CCCCAGCACA
CACACACACA CACACACACA TACACACACA CACAAGATTA TAAATTCCAT GAAAGGAAGG
GCATTGTTTT GCTCAAAATT AGTTCCAGCT TCCACAATAG TGCCTGGCAT AGTAGATAAA
TCAATATTTG TGTAAGAAAG GAGAAGAGGG AGTAAAAAAC TAAGAGCATT TTTCACCCAT
CAATTTGGCA AAGATCAAAA TATTTTATAA CACTGTGTTG ACAAGTATAG GTAAATAAGA
ATACTGCTAG TAGATCCTAT GATTGGTGAT TTGGCATTAA CAAAAGTACA AATTTCCCTA
TTCTATGCTG TAGTAATTCC CTTTCTAGAC ATACAGACTA TGGATATATC CTTACACATG
AAAAATGATG TGAGTTCACA GTAAGTTATT GCAGCAATGT TTGAAAAAGA AGAATTGGAA
ACAACCTCAT GACCACCAAT GGGGTACTTA TTAACAAATT ATAGAACATA ATACACAGTT
GAATACCGTG CAGTTGTTTA AAAAGAGCA AGATCAAGGA AACACTTATG TACAGCCTTT
ACCAAGACCA CCTGGTAAAA AGAAAAATAA GAAAGGTACA GAAGTGCTAC TATTTGTGCA
GAGGGGAAAA AGCGCGGACA ATCTATAACG GTGTAATATA TCTACGGAAG GATATACAAG
TCACGAAAAA TATTGTCAAA CTAGACGCTG GGGACATTT ACTCTTTTA ATAAATGTAT
GTGAATGCAT TACTTATCCA TATTACTCAA TAATTAAACC GAAAAACGTT TTAAAGAAGT
ACAAATAAGA CTTGCTCGCA GATCCCGCAA TCCATCAAT ACGAGGCGTA AAAGCCGGGT
CCTCCACTGG CTAGGGCCGA GGAGGCAAGC ACTCAAGCTG CCACAGAGGC GAAGCTTCCT
AGAGCGGCCC GGAAGTGCCC GGCTGAAGCG GCCGGCGCC GATTGGTGTC TTTGAGTCTA
GTCTTTGTTC GGGGCTGTCC AAAGGACGCT AGCTGTTGCA CCTGTTCCTC CCTGCGCGTA
AGGTGAGTGT CTCCCGGCTC CCAGGTGGAG AAAAGGGGAC AAGACGCAGC TGTGGTCAGC
AGCAACACCC TCCCCACACC TCCCTGTCGC GGGCAGAGTG TAACACTCCT GTCCCTCCCT
CCGCCCCCCA ACAGATCTAC AGGAGAGGAT TTGGCCCAGC CTTCCGGGAG AGGATGGGTG
GAAGGGGGAC ACTGGTTGCG GTTCCTCTGC AGAGGCATCT GTCTGATCCC CTTCCAGGGT
TGGCACACAT ATCCTATAAC CAGTGAATCC TGGGGGCACA AGCTGGCCCG TGCATCTCAT
GGTAACAGAA TGAAGAGCCT TTTAACAAAG CCGTTAATAA TACTTGGCGT TTATTTAGTG
CTTACTAGTG CCCGCTGCCA TGCCAGGGAC GTTGCATACG TTCTCATGTA ATCTGTATAT
CAACCCTGTA ACACACATGA GAATTGTACC TGAGGATCTG TAGTTCTAGT CCAGATAAAT
AACTTCCTCT AAGTTACACA ATAGAGCACA GATTCAAATC ATATCCCTGC GTCACTGTTT
TTTGTTTTGT TTTGTTTTGT TTTGTTTCAG CTTCCTATAA GACTGTTTTC TCTGATTGAC
TTCTGGTGGC TTGGCTTCAT TATGATGTGT TTATGTTCAC AGAAATTTTT GTAATTTCTC
TATGGTAACA ACTTTTTATG CCTTAGGAGT GTCTCTGAGG CAGGATTCTA AGAGATTCTC
TTTGACTCAA TCCCAGATAG AGGATAAATC TCCTGGCAAA GCCCAGAATG ACCACAGCCC
TGGAACCTGA GGACCAAAAA GGACTTCTGA TAATTAAGGC AGAGGACCAT TACTGGGGAC
AGGATTCCAG CTCACAAAAG TGCAGTCCTC ACAGGAGGGA ACTCTATAGA CAACACTTCA
GGAAGCTCTG CTATCAGGAT GCACCTGGAC CCCGTGAAGC TCTTACCCAG CTGTGGGAGC
TCTGCCGTCA GTGGCTGAGG CCAGAATGCC ACACCAAGGA GCAGATTTTA GACCTGCTGG
TGCTAGAACA GTTCCTGAGC ATTCTTCCTA AAGACCTGCA AGCATGGGTG CGTGCACACC
ATCCAGAGAC TGGAGAGGAG GCAGTGACGG TACTGGAGGA TCTGGAGAGA GAGCTTGATG
AACCTGGAAA GCAGGTGTGA AGGGCAGTC ATCTGGCTGT GAGTGATCAG GGGATATGGA
TGGAGCCAAA GCAAAGGCA TATGAAAGAA CATCTGAAAA TATTTATCCT CTAAAGAACA
AGGCATAGGA AGGGACCTGA CTACCTATGT CAAATAATTA AAGTGTGGCT GGGTAAAGAG
AGGAGAGTCA CTAGACTGAT TCTATGCCTG TTTGGAAGGC TAGGATCAGT GGGAAGTTAC
CAAAAGGCAA TCAGGTATCA GAGGAAAAGA AATAATTTTC TGCCATTCAT AGATACCCAT
AAATAAAATA GGCTACCCCA TAAGAAACTC CCTTTCCATA TAGGTATTCA AGCGGAGATT
CAAGTAGATG TCAAGGATAT TGCAGAATAG GACTGTCCAA CAGAAATATA ATGCAAGCTG
TATATGTATT TAAATTTTCT AGTAGCCACA TTAAAAAAAA AGGTGAAATA TATATTTTAT
TTAGCCCACA ATATTTAATC ATGTAATCAA TATTTTTAAT GAGGTATTTT AGATATC
```

Figure 1L 3216-1
>1-5        00001

ATGGTAAGTA TGTGGTTACA ATAACACCAA GGTTGTTTTC ACCTAATTGC AGGATTTATT

GTACCTCAAA GTAGAAATCT TAGAGGCATT CCCAGAACTG GGGTTAATCA GAAGTCAATA

TGGTGGGTTA CCATCCAAGA TGGAGTGGCT TTCAGCTGGG CACAGTTGCA GTTGGCCAAG

ATCATGCCAC TGCACTCCAG CCTGGGCAAT AGAGCTACAG TGTCTAAAAA AAATCTATAT

CTATATCTAT ATATATATAT ACACACACAC ACACACACAC ATATGCACAC ACACACATAT

ATACATATAT AATATTCATG CACACACATA TTTTTGTACT CTAGTTTGTT GNCTTGAACA

TTATTTCCTT CATATCTTTT CACTAGGAGA CAGCGGATTG CCACACCGAA GAGTGAGAGA

TCAATAAATG TTTGTTGAAA TTATATATAA TTTCCTTTGA TTATTGTACA GCTTGGGAGC

CCATATTCAA ACCTCTTTGA TGATCATATG GTCTAGGAAA GAAAGTGCTT TGTTCACCTT

ATAAGAGAAA ATTAAGGGTA TCGTCTTCAC CACCCTCTTT CCTACGATGA AAAAGCCTGT

ACTTTGTACA GTGGACAAGA AGTATCTATA TTCAATTCCT GGCTAGTAGG ATCAACTCAT

TTGAAAATAA GCTGATTTNT TTNNNNNTTC AGATGGAGTC TCGCT

Figure 1M 4072-2
>2-2           00007

TTTTCCAATG AGTTGATCCT ACTAGCCAGG AATTGAATAT AGATACTTCT TGTCCACTGT

ACAAAGTACA GGCTTTTTCA TCGTAGGAAA GAGGGTGGTG AAGACGATAC CCTTAATTTT

CTCTTATAAG GTGAACAAAG CACTTTCTTT CCTAGACCAT ATGATCATCA AAGAGGTTTG

AATATGGGCT CCCAAGCTGT ACAATAATCA AAGGAAATTA TATATAATTT CAACAAACAT

TTATTGATCT CTCACTCTTC GGTGTGGCAA TCCGCTGTCT CTAGTGAAAA GATATGAAGG

AAATAATGTT AAGTAACAAA CTAGAGTACA AAAATATGTG TGTGCATGAA TATTATATAT

GTATATATGT GTGTGTGTGC ATATGTGTGT GTGTGTGTGT GTGTATATAT ATATATAGAT

ATAGATATAG ATTTTTTTTA GACACTGTAG CTCTATTGCC CAGGCTGGAG TGCAGTGGCA

TGATCTTGGC CAACTGCAAC TGTGCCCAGC TGAAAGCCAC TCCATCTTGG ATGGTAACCC

ACCATATTGA CTTCTGATTA ACCCCAGTTC TGGGAATGCC TCTAAGATTT CTACTTTGAG

GTACAATAAA TCCTGCAATT AGGTGAAAAC AACCTTGGTG TTATTGTAAC CACATACTTA

CCATACACAA ATCCTGCCCT TAGGCTAGGC GCGGTATGTC ATGCCTATAA TCCCAACACT

TTGGGAGGCC GAGGTGGGCA GATTACTTGA GGTCCAGAGT TTGAGACCTG CCTGGCCAAC

ATGGTGAAAT GCCATCTCTA CCAAAAACAC AAAAATTAGT TGGGCATGGT GGGGCGTGCC

TATAGTCCCA GCTACTCCAG AGGCTGAGGA AAGAGAATCG CTTGACCTGG GAGGCAGAGG

TTGCAGTGAG CCAAGATCTG GCCATTCCAG CCTGGGCGAC AGAAGGAGAC CGTCTCAAAA

GAAAAGAAAA AAAAAATCC TGCCCTTAGG CAAATTCCCT GTGGTTCATA AGCCCTGGGT

TTGGCTGGTG ACAATGTGGG GATCC

Figure 1N 950-1
>950-1        00005

CTGCAGAAAG ACTCCTGTTG TCCACCTCGG GAGCTGACAC GATAAATGCG GGTCAAATCT

CAATCCTTTA ATATCTTTAT GACTTCTTTC TCTTTCTCTT CAATTTCTAT TTTCTCATGT

TCAAGCTCTG ACATTCAAAA CTAAACACCT TTCTCTAACA TGTTGCTTTA ATTATTTAAG

CATTCTGCCT GGGATTTTTT CAATTACTCT TGGGAGTTTT CATAAAACTC TACCAACATA

TCTCCAAGTG GCCAGGCTTT TCAATCACTG CTTCCCTCCG TGTGTATTTC ACACACACAC

ACACACACAC ACACACACAG CACTTAAATT GAACAGGTTT ATTTCTTCAC ACAGGAATTC

CTACGAACAG CCCGGTTTTC TCCACCATAT GTCCACTCCT TCTCTGCATA GCTGAATCGN

GATTCTCACA CTCTAATATT TTACATATTC TTACACTCTG ATATGATCTT GTCTCTTATT

CTTTATGGC

GATCACCTGA GGTCAGGAGT TCAAGACCAG CCTGGCCAAC ATGGTGAAAC CCCATCTCTA

CTACAGATAG AAAATTAGCC AGGTGTAGTG CCCAGCGCTG TAATCCCAGC TACTTGGGAG

GCCGAGGCAG GAGAATTGNT TGANCTCGGG AGGTGGAGGT TGCAATGAGC TGAGACACGC

CACTGCACTC CAGNCTGGGN GACAAGAGCA AAATTCCTTC TCAAAAAAAA AAAAAANNTG

CAANCCTAGA CTCTTATAGC TTGCAGACGA GAACGATGAA ATCTCAGATG ATTGAGCATC

TCACAGAAAC AAAGGCAATA AAACTCATAT TTACCCTACT CATCTAAATT TATGTTCAAA

GCTTTTATTT CACTACTAGG GCTGTAATGT GNCCTGGAAC ACATGGCATG TATGTGTGTG

CATATGTGTG TGTGTTGACC AAAGAGGTTG GAGGAATTTT TTGATACAAG GNCAAGCACT

CTCNCAGAAT TGGATTCCTA NCTNATGCTG TAGTTATGGG TCTTCTGCCA ACCAAATTCA

AGACTATCAT TTCTCCTTAG GAAAACCTGC CTGGTGGTAC ATGCCTTTGT TAACATCAAA

TTCGTTAAAA TTAAAATTAC ACACACACAC ACACACACAC ACACACACAC ACACTCGCAT

CCCTCCTGAA TTAAACATTT TTCTGCAG

Figure 1P 950-3
>950-3          00001

TGCCAGCAGA CTCTTCTAGC TGGCGAAGGC AAGGAAACAG ATTCTCCTCT AGAGCTTACA
GAAGGAAGAT AGCCCTGCTG ACTCACTCTA GCACCCCTGA CATCCAGAGC TGTGAGATAA
TAAATTTGTG TTGTTTTAAG CTATTAAGTT TGTGGTAATT TTCACAGCA GTAATAGGAA
ACTAATGCAT GCCCTTTCCC AGTCAGTCAC ACTCCGACCA CACAATTTCC AGTCAACTAT
AGGCCCTTTC CATCATGATG GTTTTGCCTT TTCTGGAATT TAATCTAAAT GGATTAAATT
ATATGCTATG TACTCTAGTT CCTGGTTTTT GCTCAGAACA TTTTTGAGAT TCATTCATGT
TGTTGCACAT ATCAGTAATT TATTCCATTT ATTAGCACTT TATTGGTAAA ATGTATTCTA
TTTGTACAGA CATGCCACAA TTTGTTTTTC CATTCATGTG TGGGTGAACA TTTTTATTAT
TTTCACATTC TAGCTATTAT AAATAGGGCT GCTGTGCAAA TTTGTGTAAC AAGTCTTTGT
GTAGACATAT ATAAGCCAGA GTTCTTCAGA AACAGAAAAC CAATAGTGTG TGTGTGTGTG
TGTGTGTGTG TGTGCGTGTG TGTGTGTAGA CAGTGATTTT AAGGAATGGA CTTACATGAT
TGTAGAGTCT GGCCAGTTCA GATTCTGCAC GGTATGCCAG CAGGCTGGAA ACCCAGGAAA
AAGTTAATGT GGCAGCTAAA ACTCAAAGGC TGTCTGCTGC CCAAAAGTCC CTCTTCCTAG
GGAGAGAAGT TAGTCTTTTT TCTCTTAAGT ATTTTCAAC TGATAGGAAG CAATCTGCTT
TACTCAAAGT GTACTGAATT AAATGTTAAT CTCATCCAGA AGTACCTTCA CATCAACGTC
TAAACTAGTG TTCGATCAAA TATCTGAATA CTATGAGCTA GCCATGTTGA CACGAAAAAT
TAACCATTGN ATATGTTTTC ACTTCTTTTC CAGGAAATAC CTAGGAATGG AATTGCTGGT
CATTTAGTAA GTGGGTGTTT AACTTTATAA GAAGCTACCA GTGTTTTCCA AAGTGGTGGT
TCANTTTACA TTCCAAAAAG CATTATATGA GAGTTCCAGT TGNACAACCT CCTCAGCATT
TGNTATTGTC AGACTTAATG TTTATG

Figure 1R 950-4
>950-4        00007

AATCTACCAT AGTTTCAGTT TCATTGTATT TTCTTATATA TTTATATTGT GTACTGATGT

GTGCATGGAT TAGTAATGAG TACTCTATTA TTTTTAATGT CATAATTATT CATTATTTAT

TTATTATTTA TTAAAAATAA TATTTAATAT TAAATATTAT TTATTACTTA TATTATTTAT

TATTATAATA ATTTATAATA TGTCACATTA TAAAATATTA TTTAATTAAA ATTTAATGTC

ACTCTATTAT TTTAATATCA TAAAATACAT GAAAATACAT TTTTCTGTAG AATCACGTTT

TCCTCCTACT GTGAATAAAG ACATAACTCA CTAAGGGGAA GAATCTTGGC CCNAAGTGTG

TGATAAATCA NANAANANAT AAAAGTGTNC NNAAACAAAC AGTAAAGGTG AAAGGAGGCA

CAAATTTAAT AAAGTTACTC CATAAATCAT AATTGACATT AAATGTTGGA ATGTAGGAAC

TGATTTATTA ACCATATAAA TTTAAAACAC ACATGTTATC TTTTGACAAA TTGTTTACCT

ATTTTAGTTT TCAAAGTGGG CAAAATTAAC ACCTCAAAAC ATATAAGTGT TTTCAGAGAA

GGATCACAGA GTGTGTGTGT GTGTGTGTGT GTGTGTGTGT GTGTGTATAA TGGTAATNTG

TAGACTTAAC AGCACCTTTT GCCTAAATGA CAAAATGGCC TAGACCCAAT CTGGCAGAGT

CCTTTTTCCA GAAGAACTGG GAAAACTTTT CATATTTAAG TTTGGAACAA CAGAGAGAAC

GGGAAGACTT TGGCATTTAG AGAATGTGAA TATTTGTATT TCTCGATAAA GTGAGAAATC

TTTGTGGAAA AGCTATGGCT TTANTCAGTT TCAAATCTGA GACCCCTTTC TTGTAGGCAG

ATGTGCTAAC CANTTNACCC CAAAAAACTT TCTCTTCTGT GCAGCAATCC ATAGCAGAAT

GAAAGGAGGA TTCTTTGGAT ATACTCAAAC CTAATAACTT

Figure 1S 950-5
>950-5      00004

CTGCTGAGCA TTGTGTCCCT GTGAGCCCCT CTACGTTATT TTACCTCTGA CTGGAACACA

CCTCCATCAT TTTTCCCTCA CTTCCTGCAA GTTGCTGTCT AAAGGTGACT GTTCCACATT

TTTGTTATGA TAGAGGGTCC TTATTGGTAC CATGTGAGAA ATTACCTTGA TGCCCTGGTA

GGCTCCAAGT ATAGTCCCAT GCAAGCTCTC CCAGAGGACA CAGCACAAAT AGGTTTGCAG

ACTATGCAGT GAAATGCTCA AATCACAGCT TCATTAAAAA ACATAGCAAG CAGCAAGGGG

AAAAAGAAGA GCAAGTTAAT GGTTTAGTCC CTAAGTGATT TGCCAGAACC ACACTATCTG

ACTCAAGTGT GAGCAGTTTC CGTATATCTG ATCTCTTTTA CATCGCTCAA TCAGCCTGTA

GGATAGACAC AGAGATATAT ATGCCTGGAC CAACCAATT AGTTGGTTGA ATAGCCATGG

ATTTTATTTT TGTTCCTAAA GTAGAGAACT TATGGTGTCT CCAATTTGTG GCTGACTCAA

GGCCTCATGA ATAATGAGTC AGTGCTTCGA TGTCTCATAT ATCTGTGAAT TCTGAATGTG

TGGCTCCTTT TGTATATTGG GTGCATCAGG AACATTAGGT ATCTTTTGAC CCTTCCATCC

CTTATATCTA TATTTAACAA CATATGCTCT TTTTACTAAC TACTTATGTC TACTTAAAAC

ATCTTAAGCA TTTTTGCCTA CATTTTACTA ACTAAAAGCA TATTTATCTT TTATAATAGA

ATTGCTCATT TACAAAAGTA AATATGTGTT ACAATCCATA TCATTTATTG GTGTATCCCT

GACATATAGT AGGCACTCAA TACATATATG GAATGAGAGA ATTGTGCTTT CTCTCTCCCT

TTTCGCCTTC CCCTCCTCCT GCTTTTCTC CTACTCTCAC ACTGTCTCTC TCTCTCAAAC

ACACACACAC ACACACACAC ACACACACAC ACACACACAT TGGACAGGAA TCCCAGAGAT

CTGGGTTCTG GCGTGACAGC ATGTTTTTCA CAAATACTTC TTGGTTTCCA TTCCTTCAAA

TGTAAATAAA GGTAGGGTTT AGTAAGATGA TCTTTGAGTT TCCTTCCAGG ATTCAGAGTT

TCATCAATAA TTTCTTTATT CCTTTGCTCT ACAAGGTTTC TTTGTGCTGT GGCTTTAATG

TAGCCTATCA AACACATTTC AACAAAATCA AAAGCCTTTT GTTTGCCCA TCACCATTTC

TAGGAGGATC ACTGCCAAGA TCCCAAAGTA GAGGAAATTT TTCCTATAGA ACATAATTGA

ATTTTGTATT AAGCAAGCTA AAACCAGAGA AAGATTAGAT TTTAAAACCT TTAAAAGTGA

AGCTAGGAGA GGTGCCTCAT GTCTATAGTC CCAGCTACTT GGGAGGCTGG AGTAGGAAGA

TAGCTTGAGC CCAGAAGTTC AAGGCTGCAG

Figure 1T 950-6
>Y950-6        00004

CTGCAGAAAG ACTTCTGCTG TCCACCTCAG GTGCTGACAT GATAAATGTG GGTAAACCTC

AATCCTTTAA TATCTTTATG ACTTCTTTCC CTTTCTCCCC AGTTCCTGTT TTCTCATGTT

CAAGCTCTGA CATTCAAAAC TAAACACCTT TCTCTAACAT GTTGCTTTAA TTATTTAAGC

ATTCTGCCTG GGATATTTTC AGTTAGTCAT GGGATTTTTC ATAAAACTCT CCCAATATAT

CTCCAAGTGG CCAGGCTTTT CAATCACTGC TTCCCTCCAT GTGTTTTCAC ACACACAC

ACACACACAC ACACACTCTC CACTTAAATT GAACAGGTTT ATTTCTTTAC ACAAGAATTC

TTACAAACAG CCCGGTTTTC TCCACCATAT GTCCACTCCT TCTCTGCATA GCTCAATTTT

GATTCTTACA CTATATTTTA CATATTCTTA CACTCTGATA CGATCTTGTC TCTTATTCTT

TATGGCTCTG CTCTGTAATT TTGTTGTTGT TGTTCTGAAA TATAGTTGGA CATGTAACTT

GTACATGACA CACCTTAGCA AGGAGGCAAC TCATATCTCA GATGTAAGTG AAAGAAGCAC

TCTCCAGGGG TTTCCTATGG GAGTGGTCAG CACGCTGGCC TCATTGGTGG AATGGCCTAG

TTACGAAAAC AGCAGGAGCT TTTTGCCTTC CAGAAATCTG ACCATCTCA CAACCCCCAG

ACAG

Figure 1U 950-8
>Y950COS8        00002

CTGCAGATAT GGGCTTCATT AATTACATTG TTTTTCAAGT CTCTCTTTCT ATATATATGT
GTGTGTGTGT GTGTGTGTGT GTGTGTGTGT GTGTGTGTTG TTTTTGTTTT TGTTTTTGAG
ACAGAACCTC ACTCTGTCTC CCAGGCTGGA GTGCAGAGGT GTGATCTTGG TTCACTGAAA
CCTCTACCTC CCAGACTCAA GTCCAGCCTC CCAAGTAGCT GGGACTACAG CTGCAG

TCGACTCTAG AGGATCCCCC NAGGGGAAGA CCAAGTCTGG GACTTCAGCG CCAGCCTCGC
CACCCTGCTT CCCACAACCA GATGTCTCCT GCGAAGTAGC CCCCTCTAAT GCCAAACCAA
AAGCAGAGGT CATAAGGACT ATATCCCTTA CACACACACA CACACACACA CACACACCCT
AACGGCTAAC TTCTCTGGAA GGTGCCTCAT CCAAGCAAAG CAGAACTGAA GATACTTTTA
CATGCCTTTT TCCGTTATTT TTTATCCAAT CAGACTTTTT CAGACTTCCT TTGAATACAA
GTATCTGCAG GATTTTNCCT TGTNCACCTG TAGACACTTT TTCTCTTTTN CAAGGAAGGG
TAC

TCCCTAATGG AATATTATGC AGCTGTTAAA AAGAATGCTT TAAAAAAAAC GACATAAAAT
ATGCTCATGG CATTGTATGG GGTAAATCCA AGTTGCCAAG TAGTGTATTC TTATTTACAT
GATGTCACAC ACACACACAC ACACACACAC ACACACACAC ACATATAGTT TTAGGAAAAA
AGAGTGACTA TAAGGGTCAA TGCCAAGATG TTAACAGTGC TGTTACATTT TTTTTTTTGG
TGCAACAGAC AGCTCCTCTA AAGATAACTT TCTCTATTTG TCTCTATCCC AAACTATCAA
TGGTGTGGTT AAGAAATAGG AAACTCGGCC GGGCGCGGTG GCTCACGCCT GTAATCCCAG
CACTTTGGGA GNCCGAGGCG GCGGATCAC GAGGTCAGGA GATCGAGACC ATCCTGGCTA
ACACGGTGAA ACCCCGTCTC TACTAAAAAT ACAAAAAATT AGCCGGGCGT TGTAGCGGGC
GCCTGTAGTC CCAGCTACTC GGGAGGCTGA GGCAGGAGAA TGGCGTGAAC CCGG

GTCTCGCTAT GTTGCTCAGG CTTATCTTGA AACTCTTGGC CTCAAGCAAT CCTCCTGCCT

CAATTCCCAA AGTACTGGGT TACAGATGTG AGCCACCATG CCCAGCCAAA ACCATAAAGA

TTTTTATTAT GACTTGCAAG GAGCAAAGAC TATGTGTTTC AGTCAGCTAT TGCTCCATTA

AAACACACAC ACACACACAC ACACACACAC ACACACACAC AAATGCTTAA AAACATACAA

TAAGCATCTG TGTGTGTCAG TTGAAGGTCA ATAGCTCTAG GCCAAATTAT ATGAATGGCT

GTACCTTAAG ATGTAAGTAC ACTTCAGCTT ACCTGCTTTG CGCTTCACAG TAGGAACTCT

AGTTAGTTCA AAGCATGTTC TTTCTGGGGC CAAGGGTGAA AAGACAGCAG CTACCCAAGG

GAAAATTTTT CTCATGAAGA TGGCAGAGGT GCATATGGAC ACCCAACTAT GCAGGCATAT

TCAAAGGCCC TAATTGACTC ATGCCTGCTA ACTGCACATT GACCAAAGTC ATTGTCATGC

CCAAGGCCAA AGTCAAAGTG ATATGGAAAT ATACCACATG TCTTTGGGAG GAATTGCAGA

GTTGTTAGGC AAAGGGCTTA GATATGGAAA GAAATGAAGA ATTTACCAAA ACTTACAAAT

TAACCTATAT CT

Figure 1Y 63-2

```
GACGGTATCG ATAAGCTTGA TATCGAATTC TCTGCTGGGA CAGAAAGTAT ATAGTGCTCA
TCAGTCTTCC AGAAGACTTG CATTCATTTG ACAAATATTG ATTAAGTGCT GATTATTTAC
CATGCACCTA TTTTAAGTAC TGGGGATACA GCAGTGAATA AAACAGACAA AAGGCCCTGC
CTTTATGGAG TTGACTTTGT AGTGGACAAA AAGAAAAAA ATTATTTTAT TCAATCAACT
TCCCAAAAAT TCATATAATA CTGTTTATTA TCTCTTTTTC AAAATGAGCA AACTGAGACT
CAGAAAGATC AAATTATTTG TGGGACACAA ATGTTAGTGA GTGGTAGTTT ACCCATAAGC
ATGAATTATA TTGTCCAGGG AGAAACTACA CCCCTAGATG GCGAGGCTGG GGTGCTGGAA
ATAAAAATAC TATAATAGAA ATAAGAATG CCTTTGATGC ATCAGTAGAC TAGACATGAC
CAAGAAAAAT CAGTGAGCTT GATAAATGG CTATAGAAAT TTCTAAAACT GAATTGCCAA
GACAGAAAAA AGAACTAAAA AGACAGAATG GGCTGGGCAT GGTGGCTCAC GCCTGTAATC
CCAGCACTTT GGAAGGCCGA GGCGGGCGGA TCACGTGAGG TCAGGAGTTC ATGACCAGCC
TGGTCAACAT GGTGAAGCCC CGTCTCTTCT AAAAATACAA AAAAATTAGC CGGGCGTAGC
TATGTGCCCC TGTAATCCCA GCTACTCAGG GGGTTGCGGC AGGAGAATCG CTTAAATCCA
GGAGGCTGAG GTTGCAGTGA GCTGAGATAC TGCCATTGCA CTCCAGGCTG GCCGACAAAA
GCAAGACTCT GTCACACAAA CACACACACA CACACACACA CACACACACA CACACACACA
AAGAATGAAA TATCTAAGAA CTGTAGGACA ATTATAAAAG CTGTAATATA CATGTAATAA
AAAAAATCAC AAGGTGTGAT ATACATGTAA AGAAACATAC TGGAAGGAAG AAAGAAAGAA
ATAGAGAAAG AGAGAAAGAG AAAAAAAAGA AAAAGAGAA AGAAAGGAAG AAAGAAAAG
CAAGGAAGGG AGGGAGGTAG CAAGGGAGGG AGGAATGAAG GGAGGGAGGG AGGGGAAAGA
AAAAAATTAG AAAAAATATT TAAAGCAATA ATTACTGAGA ATTTCTTAAA ATTAATAATA
AACCTCAAAC CACAGATATA GGAAGCCCAG AGAATGCCAA GAATAAATAA AAAAAAAAGT
TACAACCTGA CATGTTGTAA CCAAATGACC CCAGTTTTTT AAGAAAACGG GAATGAAGTA
CTATTTTTTG TTTTCTGAGA CGAATTACTA TTTTTTAAAG CTTTCTCTTC TTTTCCCCTT
TCCCCTTTTC CTCTTGCTCC TCATTTCCAA CTTAGCCCTT CAGAAATGCA AATACAACGT
TTCACCTCCT CCCCTCACCA GACATTCGCT ATAGGAAAAA TTCCTCTAAC TACGTGCTTC
AAGACACAGC TCTCCTCCAG AGCTGACAGT CAATTTGCAG ACCAAATTGC CAGGGAACTT
TCATCTCTAG GGCGTGGCCT CGGAACTTCC CACTCTCCAG GAGTGGTCTT GGAACTTTCT
TCCACCTGGA GAGCATATTG AAAACATGCC CTTTTTGGTC ACTTTTTCAA TCTACTTCTG
TCCATGTAAG TGCTACCTCC CACTGTNCAG TAGATAACTN CCCGGTANCA AGGGGACCCC
TNCCCTTGCT CATTTCCTCC CCTACCANAT GNAAATGCTT ACNTTTTTTT TTTTTTTTTG
CCACTTCAGC TCCAAAGGTG AAACGGCACA GTTAAAAGCA AGAAATTTTG TGTCCCTTCC
CCAAGCTAGC TTTGGAATAA ATCCACTTTT CTTGTACCAG ACCCCACTCT TGTTAATTGG
ACTCTACATG TGGTAAGCAA CTAACTTGAT TTTCGGTTAC AATATAATAT TCAACTTCAG
TAAATCAAAG ACAATTTTGA AAGAAGCCAA AGGGAAAAAA ATGACCTGAA GAGTCCTGTT
```

Figure 1Z 63-3

CATCTGTTAC TCTCTGTATC CATCCTGAGT AATGTTCTTT TCAGCTCAGT CACAATCATT

TTTTGATAGC CTATCCTATA AGCTTAACTT ATAGTGTTAA TCAGTATTAA TACATCTTAG

TGGGAAAGAA GGAAAAAATA AACGATCACA CACACACACA CACACACACA CACACACATA

CATTTACGTA ACAGAGCAAG TGTGAAAATA CCTAAAGGCT TTATAGCTCC TTTTGTCAAT

GGATACATGA CAGCATTTTT GGCATTCTTT GCTACTCTTA TTCTATGCTC CATTTGTCTT

CAGTCAGCAC CTCAGCTGCC CTTATGTTTT ACTTGGTAAG GCAAATTCCT AAATGAGCCT

GGTAATTAGT CATCCAGCTT ATAGGAAGGT ACTATAGTTT TTCATTAACT TTTTCACTGG

GCTTGAGAGT AGTAAGGACT CCCAGAGAAT TCCTTGTGTT CCAAAAGTAC TTCTCCTTGA

CATCTTGGTA TAGGATTAAT AACTGTTTAC CTTTGATAAT CAGGAAGAAT GACTCCAGCT

AGTACAGTTA CGTGATGCCT ATACATTCCT TTTTTCTGG GAAAAATGTA ATGTGAAATT

Figure 1AA 373-8

GACTCTAGAG GATCCCCACT TGCTTTTTAA AATTTTATAG CGTGTTAGAC ATTAATGTCA

TTGTTTCATG TAATGCTACT ATTTACTCAT ATTTGGACCT TCCCAGCTCA TTAGTCTTTC

TTGTAGCTCA GACTACATTT TTTGGATAAT TTTTCTTTGT CCTAAAGTAT ATCCTTTAGT

GTTTGGGGTG TGTGTGTGTG TGTGTGTGTG TGTGTGTGTG TGTAGTCTAG TAACAGTAAA

TGATCTCAGT TTTTGCAGTG ATGAAAATGC TTTCATCTTC ATTTGTAAAA ACTAGGTCCA

TTGGGTATAT AATTCTAGAT TGATATGTTA TGTGGGTACC

Figure 1BB 373-29

CCTGCAGGTC GACTCTAGAG GATCCCCACT TACTATTGCT TTTATATTAA CCTCTGTTCA

TTCCATTTCA GGCATATTCG TTTGTTCGTG TGTGTGTGTG TGTGTGTGTG TGTGTGTGTG

TGTTTTCATC AGCATTTACT CTAAATCTTT CTACTAATAG TAATAAACTC TAAACACATT

GTATGTATGC AACAGAATGA ATTTTTAGCT ACTTTGGTTT CTGAATTACT GAGGTTAGCA

TGGGCTATTT GGCACTTTTA TTTGGCAGCC AACTTATGGG TTAATATCCC TAGTGTAGGT

ATAGTGGTGA AGTTAAAATT GTTAGCTAAA TTGAGGTTTG AGAATAATTT ATTATCCTTG

AGATTTNCTG TTGACTATTG CCAGAAAGAG TCCANAAGTT TAGTGTGGGT ACCGAGCTCG

AATTNCATC

Figure 1CC 68-1

AAGCTTGCAT GCCTGCAGGT CGACTCTAGA GGATCCCCTT AGAGGCTTTG AATGCTTTAT

TCTGATTCTG ATTCACATTT GACTCCAAGG GGAAAACACT CAGTTTGTGT CTGGGCAGTC

CACACATAGC AGCCAATACA TATTTAAAAT ACACACACAC ACACACACAC ACACACTCTC

TCTCTCTGTC TCTCTCTCTT CCCTAATACT TCTGATGACA TATAATAAGA TTGATCAAAT

TAGACATATT TAATATCAAT GATGTATAAC ATTTATAAAA CCTGTGCTTG TGATATTTTT

TTGTTAAAAT GTTTNCTTAC AGCAAGGAGA AAAAAGTTT AGATTGATGC CTGACTTTGC

TACATCCTGT AACAGGGTAC

Figure 1DD 241-6

GACTCTAGCA GGATCCCCAT ATGAATTTAA TACATGATAT AAAATACCGC CTANTCATCT

TTTATATTAT GTGGTTTGCC TTNTAACTAA CGTTNGGNAG TTTGNCCCTG TAAATTGAGG

TCACTAACCC CGTNTATGTT TTGGAAATCC TTTATCCCAA CTTATTGCTC TTTCTATAAC

TCTCTTTACA TATATTCTGT CTTAAACCAC TTTTGGACCT ATCTAGTCTG TGTCCTTTCC

TAGATGGCTT TTGTGTTTCC TCCTCACTTA GCAATGACAC CCTCCCATCA CCATTTCCAC

ACACACACAC ACACACACAC ACACACACAC ACACACACAC AAATGAGGTA TATAAAGGGT

CTCCTAAAAT GTCATCTGAT ATTTGTTATT TCATATTCTC AGATTTTTAA TCCATTTAGG

TAGGTCTATT TTAGATAGCC TTGTCTGAAA CAGAGTACCG AGCTCGAATT NCATCGATGA

TATCAGA

Figure 1EE 241-29

GGTACCCCTA TTCCAGGGCT AGGGTGGGAG GATTGTTTGA TCCCTGGAGG TCAAGGCTGC

AGTGAGCCAT GATCACAGCA ATGCGCTCCA GCTCTGGGCA ACAGAGCGAG ACCCTGTCTC

AAAAAAAACA AAAATGCCTA TACAATAAAT CTATAAAAAG TGGGTTTTGT GTGTCTATAC

ACACACACAC ACACACACAC ACACACACAC ACACCTGCAT AGACACTCAG GTGTTCTGGA

AAGACACAGG AATCTGAAGC CAAAATACTT GTGATTTTTT TTCAGGGGGA TCCTCTAGAG

TCGACCTNCA GGCATTCCAA CCTTCAACNT GCTCCGAGTT GCTATAGTGT CACCTAAATC

GTATGTGTAT GATACATAAG NNATG

Figure 1FF

| | | | | SEQ ID NO. |
|---|---|---|---|---|
| AG77 | HHp1-A | | CACCAAGTACACCAGCTC | 31 |
| AG78 | HHP1-B | | ACTCACACGCAAAAAGCC | 32 |
| AG64 | HHp1/3'OLA | POR | p-CTTCCAGAGAAAGAGCCTGT-dig | 33 |
| AG662 | HHp1/5'OLA-G | POR | bio-TCTTTTCAGAGCCACTCACG | 34 |
| AG663 | HHp1/5'OLA-A | OLA | bio-TCTTTTCAGAGCCACTCACA | 35 |
| AG110 | HHp19-A | OLA | CTAACAATCAATAAAATACAACTC | 36 |
| AG111 | HHp19-B | POR | ATACCCAAGAAAAATTCAAAAG | 37 |
| AG143 | HHp19/3'OLA | POR | p-AGACAATTAAGAATGTGAGGT-dig | 38 |
| AG144 | HHp19/5'OLA-A | OLA | bio-ATATATCTATAATCTATATTCTTA | 39 |
| AG145 | HHp19/5'OLA-G | OLA | bio-ATATATCTATAATCTATATTCTTG | 40 |
| AG165 | HHp29-A | POR | CTTCCTCTCTTCCATATC | 41 |
| AG166 | HHp29-B | POR | CCCTCTATATTAGGTTTTC | 42 |
| AG190 | HHp29/3'OLA | OLA | p-TTTTAAAAATGTTAATCTTTGTG-dig | 43 |
| AG191 | HHp29/5'OLA-T | OLA | bio-TTGGGGATTTTATAGATTTAT | 44 |
| AG192 | HHp29/5'OLA-G | OLA | bio-TTGGGGATTTTATAGATTTAG | 45 |

FIG. 2

METHOD TO DIAGNOSE HEREDITARY HEMOCHROMATOSIS

This application is a continuation-in-part of U.S. Ser. No. 08/559,302, filed 15 Nov. 1995, which is a continuation-in-part of U.S. Ser. No. 08/436,074, filed 8 May 1995, the contents of which are incorporated herein by reference.

TECHNICAL FIELD

The invention relates to genetic tests for subjects carrying one or two copies of a mutated gene associated with hereditary hemochromatosis. More specifically, the invention concerns utilization of new markers associated with a common mutation in this gene which indicate the presence or absence of the mutation.

BACKGROUND ART

Hereditary hemochromatosis (HH) is an inherited disorder of iron metabolism wherein the body accumulates excess iron. In symptomatic individuals, this excess iron leads to deleterious effects by being deposited in a variety of organs leading to their failure, and resulting in cirrhosis, diabetes, sterility, and other serious illnesses. Neither the precise physiological mechanism of iron overaccumulation nor the gene which is defective in this disease is known.

HH is inherited as a recessive trait; heterozygotes are asymptomatic and only homozygotes are affected by the disease. It is estimated that approximately 10% of individuals of Western European descent carry an HH gene mutation and that there are about one million homozygotes in the United States. Although ultimately HH produces debilitating symptoms, the majority of homozygotes have not been diagnosed. Indeed, it has been estimated that no more than 10,000 people in the United States have been diagnosed with this condition. The symptoms are often confused with those of other conditions, and the severe effects of the disease often do not appear immediately. It would be desirable to provide a method to identify persons who are ultimately destined to become symptomatic in order to intervene in time to prevent excessive tissue damage. One reason for the lack of early diagnosis is the inadequacy of presently available diagnostic methods to ascertain which individuals are at risk.

Although blood iron parameters can be used as a screening tool, a confirmed diagnosis often employs HLA typing, which is tedious, nonspecific, and expensive and/or liver biopsy which is undesirably invasive and costly. Accordingly, others have attempted to develop inexpensive and noninvasive diagnostics both for detection of homozygotes having existing disease, in that presymptomatic detection would guide intervention to prevent organ damage, and for identification of carriers. The need for such diagnostics is documented for example, in Finch, C. A. *West J Med* (1990) 153:323–325; McCusick, V. et al. *Mendelian Inheritance in Man* 11th ed., Johns Hopkins University Press (Baltimore, 1994) pp. 1882–1887; Report of the Joint World Health Organization/HH Foundation/French HI-I Association Meeting, 1993.

Although the gene carrying the mutation associated with HH is at present unknown, genetic linkage studies in HH families have shown that the gene responsible in Caucasians resides on chromosome 6 near the HLA region at 6p2.13 (Cartwright, *Trans Assoc Am Phys* (1978) 91:273–281; Lipinski, M. et al. *Tissue Antigens* (1978) 11:471–474). Within this gene a single mutation gives rise to the majority of disease-causing chromosomes present in the population today. This is referred to herein as the "common" or "ancestral" or "common ancestral" mutation. These terms are used interchangeably. It appears that 80–90% of all HH patients carry at least one copy of a common ancestral mutation which carries with it specific forms of certain markers close to this ancestral HH gene. These markers are, as a first approximation, in the allelic form in which they were present at the time the HH mutation occurred. See, for example, Simon, M. et al. *Am J Hum Genet* (1987) 41:89–105; Jazwinska, E. C. et al. *Am J Hum Genet* (1993) 53:242–257; Jazwinska, E. C. et al. *Am J Hum Genet* (1995) 56:428–433; Worwood, M. et al. *Brit J Hematol* (1994) 86:833–846; Summers, K. M. et al. *Am J Hum Genet* (1989) 45:41–48.

Although each of such markers is putatively useful in identifying individuals carrying this defective HH gene, of course, crossing over events have, over time, separated some of the ancestral alleles from the relevant genetic locus that is responsible for HH. Therefore, no single marker is currently specific enough to identify all individuals carrying the ancestral HH mutation.

Several markers at the approximate location of the gene associated with HH have been described. Gyapay, G. et al. *Nature Genetics* (1994) 7:246–339 describe the markers D6S306 and D6S258 which have been demonstrated hereinbelow to be in the immediate region of the HH gene. These markers consist of microsatellite regions containing $(CA)_n$ repeats of various lengths. Worwood, M. et al. *Brit J Hematol* (1994) 86:833–846 (supra) describes an allele at D6S265 and Jazwinska, E. C. et al. *Am J Hum Genet* (1993) 53:242–257 (supra) describes D6S105 as associated with an HH-specific genotype. Stone, C. et al. *Hum Molec Genet* (1994) 3:2043–2046 describes an additional HH-associated allele at D6S1001. As described hereinbelow, a multiplicity of previously undiscovered microsatellite markers and the relevant allele associated with the ancestral HH gene defect have now been found permitting the detection of genotypes with very high probabilities of being associated with the presence of the common HH mutated gene. In addition, 3 single base-pair polymorphisms associated with the HH gene have been identified, which can be included in additional diagnostic genotypes. The diagnostic genotypes described below as associated with HH are rare in the general population, consistent with the frequency of the HH gene mutation. However, they are present in a large majority of individuals affected by HH. Accordingly, the presence or absence of these genotypes can be used as a rapid, inexpensive and noninvasive method to assess an individual for the presence or absence of the common version of the defective HH gene.

DISCLOSURE OF THE INVENTION

The invention is directed to a convenient method to assess individuals for the presence or absence, or the likelihood of said presence or absence, of a common HH-associated mutation using genetic techniques that are readily applied noninvasively. Only a sample containing the subject's cells containing genomic DNA from the subject to be tested is required. The present invention includes materials and kits useful in conducting the genetic tests. The allelic variants at specific locations close to the HH gene are marked by distinctive lengths of microsatellite repeats or by specific single base-pair differences in DNA sequence (referred to herein as a "base-pair polymorphism").

Thus, in one aspect, the invention is directed to a method to determine the likelihood of the presence or absence of a hereditary hemochromatosis (HH) gene mutation in an individual, which method comprises obtaining genomic DNA from the cells of said individual and assessing said DNA for the presence or absence of a genotype defined by at least one nonoptional marker comprising the following microsatellite repeat alleles: 19D9:205; 18B4:235; 1A2:239; 1E4:271; 24E2:245; 2B8:206; 3321-1:197; 4073-1:182; 4440-1:180; 4440-2:139; 731-1:177; 5091-1:148; 3216-1:221, 4072-2:148; 950-1:142; 950-2:164; 950-3:165; 950-4: 128; 950-5: 180; 950-6:151; 950-8:137; and 63-1:151. In the notation employed for the microsatellite repeat allele, the number subsequent to the colon indicates the number of nucleotides in the HH-associated allele between and including the flanking primers when the primers are those illustrated herein. The absence of this genotype indicates the likelihood of the absence of the HH gene mutation in the genome of said individual. The presence of this genotype indicates the likelihood of the presence of this HH gene mutation in the genome of said individual.

While the presence of only one of these alleles indicates an increased likelihood for the presence of the common ancestral genetic HH defect, the likelihood is further enhanced by the presence of multiple alleles among these nonoptional markers. Thus, the genotypes to be determined preferably include at least two, more preferably at least three, and more preferably still, at least four, preferably more than four, of these alleles. In addition, the statistical certainty of the results is enhanced by combining the information concerning the presence or absence of one or more of these nonoptional alleles with the information concerning the presence or absence of diagnostic alleles known in the art, including D6S258:199, D6S265:122, D6S105:124, D6S306:238, D6S464:206; and D6S1001:180. The predictive power of such disease-associated alleles when measured in human genomic DNA can be quantified. An example of a computerized method for this is given in Terwilliger, J. D. *Am J Hum Genet* (1995) 56:777-787.

In addition, HHP-1, HHP-19, and HHP-29 (described below) base-pair polymorphisms have been established; the presence of the HH-associated allele of one of these base-pair polymorphisms especially in combination with any HH-mutation- associated microsatellite repeat allele indicates the presence of the common HH mutant gene.

Thus, in another aspect, the invention is directed to a method to determine the presence or absence of the common hereditary hemochromatosis (HH) gene mutation in an individual, which method comprises obtaining genomic DNA from the individual; and assessing the DNA for the presence or absence of the HH-associated allele of the base-pair polymorphism designated herein at HHP-1, HHP-19, or HHP-29; wherein the absence of the HH-associated allele indicates the likelihood of the absence of the ancestral HH gene mutation in the genome of the individual and the presence of the HH-associated allele indicates the likelihood of the presence of the HH gene mutation in the genome of the individual. Preferably, the method also includes determining a genotype which is a combination of the base-pair allele with an HH-associated microsatellite repeat allele.

The invention is further directed to DNA primer pairs for PCR amplification that flank the microsatellite repeat alleles and that flank the base-pair polymorphism markers useful in the method of the invention and to kits containing these primer pairs. The invention is also directed to primers permitting determination of base-pair polymorphisms by oligonucleotide ligation assay (OLA) or by alternative methods. The invention is also directed to use of the nucleotide sequence information around the microsatellite repeats to design additional primer pairs for amplification. Applicants have provided extensive sequence information approximately 500 bp in either direction of the markers 18B4, 19D9, 1A2, 1E4, 24E2, 2B8 and 63-1. The availability of this sequence information provides additional opportunities for the design of primers for amplification of the relevant portion of DNA.

Accordingly, the invention is also directed to primers designed on the basis of this sequence information and to a computer-readable medium having recorded thereon the nucleotide sequences set forth in FIGS. 1A-1W described below or fragments thereof. The claimed fragments are those that do not coincide with nucleotide sequences presently available in computer-readable form.

BRIEF DESCRIPTION OF THE DRAWINGS

FIG. 1 shows sequence information concerning the portions of the genome surrounding several markers of the invention. FIG. 1A (SEQ ID NO:79) shows 1260 bp around 18B4; FIG. 1B (SEQ ID NO:80) shows 1260 bp around 19D9; FIG. 1C (SEQ ID NO:81) shows 1 kb around 1A2; FIG. 1D (SEQ ID NO:82) shows 1380 bp around 1E4; FIG. 1E (SEQ ID NO:83) shows 1260 bp around 24E2; FIG. 1F (SEQ ID NO:84) shows approximately 1 kb around 2B8; FIG. 1G (SEQ ID NO:85) shows sequences bracketing 73 1-1; FIG. 1H (SEQ ID NO:86) shows sequences bracketing 5091-1; FIG. 1I (SEQ ID NO:87) shows sequences bracketing 4440-1; FIG. 1J (SEQ ID NO:88) shows sequences bracketing 4440-2; FIG. 1K (SEQ ID NO:89) shows sequences bracketing 4073-1; FIG. 1L (SEQ ID NO:90) shows sequences bracketing 3321-1; FIG. 1M (SEQ ID NO:91) shows sequences bracketing 3216-1; FIG. 1N (SEQ ID NO:92) shows sequences bracketing 4072-2; FIG. 1O (SEQ ID NO:93) shows sequences bracketing 950-1; FIG. 1P (SEQ ID NO:94) shows sequences bracketing 950-2; FIG. 1R (SEQ ID NO:95) shows sequences bracketing 950-3; FIG. 1S (SEQ ID NO:96) shows sequences bracketing 950-4; FIG. 1T (SEQ ID NO:97) shows sequences bracketing 950-5; FIG. 1U (SEQ ID NO:98) shows sequences bracketing 950-6; FIG. 1V (SEQ ID NO:99) shows sequences bracketing 950-8; FIG. 1W (SEQ ID NO:100) shows sequences bracketing 63-1; FIG. 1X (SEQ ID NO:101) shows sequences bracketing 65-1;FIG. 1Y (SEQ ID NO:102) shows sequences bracketing 65-2; FIG. 1Z shows (SEQ ID NO:103) sequences bracketing 63-2; FIG. 1AA (SEQ ID NO:104) shows sequences bracketing 63-3; FIG. 1BB (SEQ ID NO:105) shows sequences bracketing 373-8; FIG. 1CC (SEQ ID NO:106) shows sequences bracketing 373-29; FIG. 1DD (SEQ ID NO:107) shows sequences bracketing 68-1; FIG. 1EE (SEQ ID NO:108) shows sequences bracketing 241-6; FIG. 1FF (SEQ ID NO:109) shows sequences bracketing 241-29.

The location of the microsatellite repeated sequence itself is underlined in these figures.

FIG. 2 (SEQ ID NO:110through SEQ ID NO:124) shows the primers used for amplification and OLA determination of the base-pair polymorphisms of the invention.

MODES OF CARRYING OUT THE INVENTION

A multiplicity of new markers which are of variant length microsatellite repeats associated with the ancestral mutation in the gene associated with hereditary hemochromatosis have been found and the allelic forms associated with the HH genetic defect have been characterized. In general, the markers reside on chromosome 6 in the neighborhood of the locus which is associated with the defective genotype and exhibit a multiplicity of allelic variations characterized by a variation in the number of nucleotides present in the intervening sequence between flanking sequences conserved in all subjects. The intervening nucleotide sequences consist essentially of di-, tri- and tetranucleotide repeats, most commonly the dinucleotide $(CA)_n$. As is generally known in the art, this type of repeat is known as a "microsatellite" repeat. The microsatellite repeat regions which characterize the markers of the present invention may be simple microsatellite repeats containing only one type of repeated sequence or may be compound. In addition to $(CA)_n$, $(CT)_n$ and other repeated sequences are found. These repeat sequences generically, are designated "microsatellite repeats" herein. As shown hereinbelow, the flanking sequences conserved with respect to each marker are interrupted by intervening nucleotide sequences ranging in number from about 110 to about 300 bases. Generally, the size of each allele differs within the context of a single marker by 2–4 bases from the next closest allele.

As used herein, "marker" refers either to a base-pair polymorphism or to a microsatellite region wherein varying numbers of $(CA)_n$ or other microsatellite repeats are flanked by conserved regions; advantage can be taken of the conserved regions flanking either the base-pair polymorphism or the microsatellite repeat to construct primers for amplifying the relevant DNA portions. In some cases, two sets of PCR primers will be required: one to amplify the general region of the DNA of interest and the other to perform OLA determination of the base-pair polymorphisms. When the microsatellite regions are amplified using the primers set forth herein, representing conserved regions at either end of the repeats intervening sequences of varying lengths result. In the case of each marker, one of the alleles found in the tested population has a higher frequency in individuals known to be affected by HH than in the general population. Each individual marker cannot be completely determinative, since any particular allele associated with HH is also present in at least some normal individuals or chromosomes. However, the presence of the HH-associated allelic form of even one marker indicates an enhanced probability that the subject carries the mutation. By using multiple markers, at least two, preferably at least three, and more preferably at least four, or a greater multiplicity of such alleles to determine a characteristic genotype, this problem is reduced to the extent that substantial predictive power is obtained. The frequency of the occurrence of the characteristic genotype combination of the alleles most commonly encountered in HH-affected individuals has so far reduced to zero in normal subjects; as more individuals are tested, small numbers in the normal population will be found eventually to share some of these genotypes. This is to be expected since approximately one in fifteen individuals is a carrier of the common ancestral mutation and is clinically normal and will remain so.

To standardize the notation, the markers which are microsatellite repeat alleles are denoted by the marker name followed by a colon and the number of nucleotides in the allele found at a higher frequency in HH subjects. Thus, the notation 1A2:239 indicates that the marker bracketed by SEQ ID NO:1 and SEQ ID NO:2 described below has 239 nucleotides which represents the sum of the nucleotides intervening between the two identified primer sequences in the HH genotype plus the nucleotides included in the relevant primers exemplified below, i.e., SEQ ID NO:1 and SEQ ID NO:2. Similarly, 24E2:245 reflects 245 nucleotides between and including the two primers identified as SEQ ID NO:5 and SEQ ID NO:6 in the HH genotype. The location of the intervening nucleotides is shown for the repeat markers as an underlined sequence in FIGS. 1A–1W.

Shown in FIG. 1 are various-length nucleotide sequences either side of the markers described herein. Each portion of the figure shows the relevant sequence surrounding each polymorphism. These sequences are of sufficient length that it is convenient to provide them in computer-readable medium. The medium would include those known in the art such as floppy disks, hard disks, random access memory (RAM), read only memory (ROM), and CD-ROM. The invention is also directed to computer-readable media having recorded thereon the nucleotide sequence depicted with respect to each marker as set forth in FIG. 1 or a portion of each such sequence wherein said portion is novel—i.e., does not currently exist in computer-readable form.

In addition to the microsatellite repeat markers described above, three single base-pair polymorphisms have been found in which one allele is present in high proportion on chromosomes of affected individuals. These base-pair polymorphisms designated HHP-1, HHP-19 and HHP-29, were discovered in the course of sequencing the relevant portion of chromosome 6 derived from affected as compared to unaffected individuals. HHP-1 is about 80,000 base pairs centromere-proximal to the marker D6S105; HHP-19 is about 110,000 base pairs centromere-proximal to the marker D6S105, HHP-29 is about 185,000 base pairs centromere-proximal to the marker D6S105. The precise nature of the base-pair polymorphisms is set forth in the examples hereinbelow. The presence of one allele, especially in combination with any one of the characteristic allelic variants among the microsatellite repeat markers characterized herein or characterized in the prior art indicates the presence of the common HH mutation.

To perform the diagnostic test, a suitable genomic DNA-containing sample from a subject is obtained and the DNA extracted using conventional techniques. DNA can be prepared, for example, simply by boiling the sample in SDS. Most typically, a blood sample, a buccal swab, a hair follicle preparation or a nasal aspirate is used as a source of cells to provide the DNA. The extracted DNA is then subjected to amplification, for example, using the polymerase chain reaction (PCR) according to standard procedures. Sequential amplification is conducted with various pairs of primers and the amplified DNA is recovered after each amplification, or, in the alternative, the DNA sample can be divided into aliquots and each aliquot amplified separately if sufficient DNA is available. The size of the insert of the amplified marker which is a microsatellite repeat is then determined using gel electrophoresis. See Weber and May *Am J Hum Genet* (1989) 44:388–339; Davies, J. et al. *Nature* (1994) 371: 130–136. The presence or absence of the single base-pair polymorphism is determined by conventional methods including manual and automated fluorescent DNA sequencing, primer extension methods (Nikiforov, T. T. et al. *Nucl Acids Res* (1994) 22:4167–4175); oligonucleotide ligation assay (OLA) (Nickerson, D. A. et al. *Proc Natl Acad Sci USA* (1990) 87:8923–8927); allele-specific PCR methods (Rust, S. et al. *Nucl Acids Res* (1993)6:3623–3629); RNase mismatch cleavage, single strand conformation polymorphism (SSCP), denaturing gradient gel electrophoresis (DGGE) and the like.

As will further be described in Example 1, one genotype associated with HH is defined by the following alleles 19D9:205; 18B4:235; 1A2:239; D6S306:238; 1E4:271; 24E2:245; additional alleles that may be included are 2B8:206 and D6S258:199. The absence of this genotype indicates the absence of the ancestral HH gene mutation in the genome of said individual and the presence of said genotype indicates the presence of said HH gene mutation.

In addition to the genotype described above, genotypes characterized by the presence of the allele associated with the HHP-1, the HHP-19 or HHP-29 single base-pair polymorphism in combination with any of the HH-associated allelic variants among the microsatellite repeat markers also characterizes an individual whose genome contains the common HH mutation. If desired, the particular allele associated with the common HH mutation can be designated in a manner analogous to the notation used in connection with the microsatellite repeat markers hereinabove. Thus, the HH-associated alleles for the herein base-pair polymorphisms are HHP-1:A, HHP-19:G, and HHP-29:G. (See Example 4.)

The alleles associated with the single base-pair polymorphisms HHP-1, HHP-19 and HHP-29 have, to date, been observed to be in complete linkage disequilibrium. Thus, the determination that one of these alleles is present or absent specifies the presence or absence of the other. For example, an individual who is homozygous for the HHP-1:A allele is also homozygous for the HHP-19:G and the HHP-29:G alleles.

As will be evident from the above description, individual chromosomes are not necessarily isolated, the particular set of markers associated with a single chromosome can be, but need not be, determined in determining genotypes. Strictly speaking the presence of alleles associated with the common HH mutation should accompany it on the same chromosome. However, the presence of the diagnostic genotype per se is sufficient to indicate the likelihood that the subject carries the common HH mutation even if the chromosomes are not separated in the analysis.

It is apparent, however, that the various genotypes can distinguish between heterozygous carriers and individuals homozygous with respect to the ancestral HH mutation. That is, the presence of more than one genotype can be detected in a single individual even though total DNA is sampled.

The diagnostic methods described below have additional advantages. Although the prior art methods for identification of the presence of the genetic mutation associated with HH are invasive, current medical practice requires investigation of immediate relatives to discover any previously unsuspected cases so that preventive phlebotomy can be initiated (Bothwell, T. H. et al. in *The Metabolic Basis of Inherited Disease*, McGraw Hill, New York, 1995, pp. 2237–2269; Edwards, C. Q. et al. *New Engl J Med* (1993) 328:1616–1620). The methods described in the present invention will be capable of detecting other cases with high accuracy in this family context, even in the event that HH is caused by a nonancestral mutation in this family. This is true because other family members who are affected will carry the same genotype as the affected member (even if these genotypes are not any of the ancestral types listed herein). Thus, these markers will still identify other family members homozygous for the HH gene.

The presence of the HH genotype also has predictive power with respect to certain therapeutic regimes where it is understood that the effectiveness of these regimes is related to the HH genotype. For example, it has been disclosed that the potential for hemochromatosis interferes with the effectiveness of interferon treatment of hepatitis C (Bacon, B. *Abstracts of the Fifth Conference of the International Association for the Study of Disorders of Iron Metabolism* (1995) 15–16. Thus, knowledge of the status of the genotype of the subject with respect to the HH mutation provides guidance in designing therapeutic protocols for conditions affected by disorders of iron metabolism, particularly liver conditions. As the correlations between treatment regimens and iron metabolism continue to become established, the diagnostic methods of the invention provide a useful tool in designing therapeutic protocols consistent with the presence or absence of the common HH mutation.

The following examples are intended to illustrate but not to limit the invention.

EXAMPLE 1

Identification of Markers for HH

Clones containing the relevant sequences were retrieved in a genome walking strategy beginning with the previously described markers D6S306, D6S105 and D6S258. Standard chromosome-walking techniques are described in Sambrook, J. et al. *Molecular Cloning—A Laboratory Manual*, 2nd Ed., Cold Spring Harbor Laboratory Press, New York (1989) and in Dracopoli, H. et al. eds. *Current Protocols in Human Genetics*, J. Wiley & Sons, New York (1994).

The DNA sequence of the human genome in the region of the HH mutated gene was determined. A genomic 3 kb clone library was prepared by sonication of cosmid and phage P1 clones. The sonicated genomic DNA was end-repaired, BstXI adapters were added and the fragments were ligated into pOT2. Resulting clones were subjected to transposon-mediated directed DNA sequencing. See Strathman, et al. *Proc Natl Acad Sci USA* (1991) 88:1247–1250.

As a result of determining the sequence of some of the DNA in this region, the presence of 10 previously unknown microsatellite repeat elements (consisting of repeating di-, tri- and tetranucleotide repeats, most commonly the dinucleotide $(CA)_n$) was noted. The length of these repeats is typically polymorphic in the human population and thus different lengths represent different alleles which are inherited in a Mendelian fashion. This permits them to be used as genetic markers (Weber, J. et al. *Am J Hum Genet* (1989) 44:388–396). Since the genomic sequence surrounding the repeats was thus available, PCR primers that flank the repeats and represent conserved sequences can be designed. Table 1 shows the names of these sequence repeat markers and the corresponding DNA sequences of the flanking PCR primers.

TABLE 1

Markers in the HH Region on Chromosome 6p2.1

| Marker Name | Primer Sequences 5'→3' | SEQ ID NO |
|---|---|---|
| 1A2 | AGT CAT CTG AAG AGT TGG | 1 |
|  | GCA TGT CTT CTT TGT TAA GG | 2 |

TABLE 1-continued

Markers in the HH Region on Chromosome 6p2.1

| Marker Name | Primer Sequences 5'→3' | SEQ ID NO |
|---|---|---|
| 1E4 | AAT CAA GTT CTA GCA CC | 3 |
|  | GAA TGG AGG GAG TTT ATG | 4 |
| 24E2 | CTG TTT ACA TCG GGA AGA GAC TTA G | 5 |
|  | CGA ATA GTG TTA AAA TTT AAG CTA GGG CTG | 6 |
| 18B4 | CTATGGATCTTATTGTGCCT | 7 |
|  | TACAGGGAGTCTACAGGACC | 8 |
| 19D9 | AGACTTTCAAAAACTCACAATCAC | 9 |
|  | GATAGAACATTAGCTTAGACATGG | 10 |
| 2B8 | GAAGGACTTGAAAGGAATAC | 11 |
|  | GGAATTTGAAGCTACAGTG | 12 |
| 3321-1 | TTTGGGTTTATTGCCTGCCTCC | 13 |
|  | AACAATGCCCTTCCTTTC | 14 |
| 4073-1 | AACCCAGAATCACATCTAGTGAGG | 15 |
|  | TGATGCATATGGCCTTTTCTTTCTC | 16 |
| 4440-1 | ATGCTGTTATTTTTTCACTTTTTCCTG | 17 |
|  | AGTACTCTGTTGCAGTGAGAGATG | 18 |
| 4440-2 | ATAGACACTGACATCATCCCTACC | 19 |
|  | GTTTTCTCTCCAGGACAAATTTACC | 20 |
| 731-1 | GTTGGAGAGATAGGTGTTCTTTTCC | 31 |
|  | CCTGTACTACCCAAGCACCTGC | 32 |
| 5091-1 | GGGTTAAATCTCATCCCGCGG | 33 |
|  | GGCTGCAGGAACTGGGGAGGG | 34 |
| 3216-1 | ACTCCAGCCTGGGCAATAGAGC | 35 |
|  | ACTCTTCGGTGTGGCAATCCGC | 36 |
| 4072-2 | AATAATGTTAAGTAACAAACTAGAGTAC | 37 |
|  | ACTCCAGCCTGGGCAATAGAGC | 38 |
| 950-1 | TCATAAAACTCTACCAACATATCTCC | 39 |
|  | GGAATTCCTGTGTGAAGAAATAAACC | 40 |
| 950-2 | TTCTGCCAACCAAATTCAAGACTATC | 41 |
|  | GCAGAAAAATGTTTAATTCAGGAGGG | 42 |
| 950-3 | AGTCTTTGTGTAAGCATATATAAGCC | 43 |
|  | CATACCGTGCAGAATCTGAACTGG | 44 |
| 950-4 | AAAACATATAAGTGTTTTCAGAGAAGG | 45 |
|  | GTCTAGGCCATTTTGTCATTTAGGC | 46 |
| 950-5 | CCCCTCCTCCTGCTTTTTCTCC | 47 |
|  | TTATTTACATTTGAAGGAATGGAAACC | 48 |
| 950-6 | GCTTTTCAATCACTGCTTCCCTCC | 49 |
|  | AGAGAAGGAGTGGACATATGGTGG | 50 |
| 950-8 | GGCTTCATTAATTACATTGTTTTTCAAG | 51 |
|  | CAGCCTGGGAGACAGAGTGAGG | 52 |
| 63-1 | CCACAACCAGATGTCTCCTGCG | 53 |
|  | GCACCTTCCAGAGAAGTTAGCCG | 54 |
| D6S306 | TTTACTTCTGTTGCCTTAATG | 21 |
|  | TGAGAGTTTCAGTGAGCC | 22 |
| D6S258 | GCAAATCAAGAATGTAATTCCC | 23 |
|  | CTTCCAATCCATAAGCATGG | 24 |
| D6S105 | GCCCTATAAAATCCTAATTAAC | 25 |
|  | GAAGGAGAATTGTAATTCCG | 26 |
| D6S1001 | TCTGGGATTCCTGTCCAATG | 27 |
|  | CCTGACATATAGTAGGCACTC | 28 |
| D6S464 | TGCTCCATTGCACTCC | 29 |
|  | CTGATCACCCTCGATATTTAC | 30 |
| 65-1 | TGT ATG GGG TAA ATC CAA GTT GCC | 55 |
|  | ACA AAT AGA GAA AGT TAT CTT TAG AGG | 56 |
| 65-2 | TGT GTT TCA GTC AGC TAT TGC TCC | 57 |
|  | TGT ACT TAC ATC TTA AGG TAC AGC C | 58 |
| 63-2 | CTC CAG GCT GGC CGA CAA AAG C | 59 |
|  | ATG TAT ATT ACA GCT TTT ATA ATT GTC C | 60 |
| 63-3 | TCA CAA TCA TTT TTT GAT AGC CTA TCC | 61 |
|  | AGC CTT TAG GTA TTT TCA CAC TTG C | 62 |
| 373-8 | CCA GCT CAT TAG TCT TTC TTG TAG C | 63 |
|  | ACT GAG ATC ATT TAC TGT TAC TAG AC | 64 |
| 373-29 | GTT CAT TCC ATT TCA GGC ATA TTC G | 65 |
|  | ATT AGT AGA AAG ATT TAG AGT AAA TGC | 66 |
| 68-1 | CTT GAT TCT GAT TCA CAT TTG ACT CC | 67 |
|  | TAT TAT ATG TCA TCA GAA GTA TTA GGG | 68 |
| 241-6 | GCA ATG ACA CCC TCC CAT CAC C | 69 |
|  | TAT CAG ATG ACA TTT TAG GAG ACC C | 70 |
| 241-29 | CCT ATA CAA TAA ATC TAT AAA AAG TGG G | 71 |
|  | ATT CCT GTG TCT TTC CAG AAC ACC | 72 |

As shown in Table 1, a large number of new markers were identified; with respect to the prior art markers D6S306 D6S258, D6S105, D6S1001, and D6S464, the appropriate primer oligonucleotides are also determined. As will be shown in Example 2, the alleles associated with HH for both the new markers and four known markers have also been determined.

EXAMPLE 2

Association of Alleles with the Presence of HH

Total genomic DNA from families represented in the CEPH collection (Dausset, J. et al. *Genomics* (1990) 6:575–577) was used as a substrate for amplification with the 14 pairs of primers representing the markers in Table 1. None of the individuals in the CEPH collection is known to have HH; thus, the results in these individuals indicate the frequencies of the various alleles in the normal population. These results are shown as the "% Normals" in Table 2.

TABLE 2

Allele Distribution for HH Markers

| Marker Name | Allele Size (base pr.) | % Normals | % HH |
|---|---|---|---|
| 1A2 | 237 | 2 | 0 |
|  | 239 | 46 | 77 |
|  | 241 | 35 | 21 |
|  | 243 | 16 | 3 |
| 1E4 | 257 | 1 | 0 |
|  | 261 | 1 | 0 |
|  | 265 | 4 | 0 |
|  | 267 | 10 | 7 |
|  | 269 | 31 | 13 |
|  | 271 | 28 | 70 |
|  | 273 | 9 | 5 |
|  | 275 | 9 | 0 |
|  | 277 | 3 | 0 |
|  | 279 | 1 | 0 |
|  | 281 | 1 | 0 |
|  | 283 | 3 | 5 |
|  | 285 | 1 | 0 |
|  | 287 | 1 | 0 |
| 24E2 | 251 | 2 | 0 |
|  | 235 | 6 | 5 |
|  | 237 | 1 | 0 |
|  | 239 | 1 | 0 |
|  | 241 | 3 | 0 |
|  | 243 | 18 | 9 |
|  | 245 | 63 | 82 |
|  | 247 | 9 | 4 |
| 18B4 | 231 | 1 | 0 |
|  | 233 | 23 | 12 |
|  | 235 | 42 | 78 |
|  | 237 | 25 | 10 |
|  | 239 | 8 | 0 |
| 19D9 | 183 | 1 | 0 |
|  | 185 | 1 | 0 |
|  | 199 | 9 | 1 |
|  | 201 | 2 | 0 |
|  | 203 | 15 | 12 |
|  | 205 | 53 | 87 |
| 2B8 | 198 | 0 | 0 |
|  | 202 | 0 | 4 |
|  | 204 | 4 | 1 |
|  | 206 | 14 | 67 |
|  | 210 | 27 | 10 |
|  | 214 | 11 | 6 |
|  | 216 | 2 | 0 |
|  | 218 | 3 | 1 |
|  | 220 | 5 | 8 |
|  | 226 | 2 | 0 |
|  | 228 | 10 | 0 |
|  | 230 | 4 | 0 |
|  | 232 | 3 | 3 |
|  | 234 | 3 | 0 |
| 3321-1 | 195 | 21 | 12 |
|  | 197 | 71 | 81 |
|  | 199 | 8 | 8 |

TABLE 2-continued

Allele Distribution for HH Markers

| Marker Name | Allele Size (base pr.) | % Normals | % HH |
|---|---|---|---|
|  | 201 | 1 | 0 |
| 4073-1 | 180 | 3 | 2 |
|  | 182 | 49 | 82 |
|  | 184 | 12 | 5 |
|  | 186 | 21 | 5 |
|  | 188 | 7 | 4 |
|  | 190 | 3 | 1 |
|  | 192 | 1 | 0 |
|  | 212 | 1 | 0 |
|  | 238 | 1 | 0 |
| 4440-1 | 176 | 10 | 13 |
|  | 178 | 47 | 25 |
|  | 180 | 38 | 61 |
|  | 182 | 3 | 1 |
| 4440-2 | 139 | 58 | 82 |
|  | 141 | 2 | 0 |
|  | 143 | 9 | 4 |
|  | 145 | 0 | 1 |
|  | 149 | 7 | 1 |
|  | 151 | 1 | 0 |
|  | 155 | 5 | 3 |
|  | 157 | 4 | 4 |
|  | 159 | 8 | 4 |
|  | 161 | 2 | 1 |
|  | 163 | 3 | 0 |
|  | 165 | 1 | 0 |
|  | 167 | 1 | 0 |
| 63-1 | 159 | 0.7 | 0 |
|  | 157 | 4.3 | 1 |
|  | 155 | 3.6 | 1 |
|  | 153 | 0.0 | 3 |
|  | 151 | 13.6 | 76 |
|  | 149 | 0.0 | 1 |
|  | 147 | 0.0 | 2 |
|  | 145 | 0.7 | 1 |
|  | 143 | 1.4 | 0 |
|  | 141 | 21.0 | 3 |
|  | 139 | 33.0 | 9 |
|  | 137 | 0.7 | 0 |
|  | 135 | 20.0 | 5 |
|  | 133 | 0.7 | 0 |
| D6S464 | 202 | 4 | 1 |
|  | 204 | 6 | 3 |
|  | 206 | 52 | 84 |
|  | 208 | 2 | 0 |
|  | 210 | 8 | 3 |
|  | 214 | 2 | 0 |
|  | 216 | 13 | 7 |
|  | 218 | 2 | 0 |
|  | 220 | 2 | 1 |
|  | 222 | 2 | 0 |
|  | 224 | 8 | 1 |
| D6S306 | 230 | 4 | 0 |
|  | 234 | 2 | 3 |
|  | 238 | 54 | 74 |
|  | 240 | 22 | 12 |
|  | 244 | 11 | 10 |
|  | 246 | 6 | 0 |
|  | 248 | 2 | 0 |
| D6S258 | 189 | 11 | 5 |
|  | 193 | 2 | 0 |
|  | 197 | 30 | 12 |
|  | 199 | 33 | 72 |
|  | 201 | 6 | 7 |
|  | 203 | 2 | 2 |
|  | 205 | 6 | 1 |
|  | 207 | 6 | 0 |
| D6S105 | 116 | 2 | 0 |
|  | 122 | 2 | 1 |
|  | 124 | 13 | 64 |
|  | 126 | 8 | 3 |
|  | 128 | 39 | 17 |
|  | 130 | 14 | 5 |
|  | 132 | 11 | 8 |

TABLE 2-continued

Allele Distribution for HH Markers

| Marker Name | Allele Size (base pr.) | % Normals | % HH |
|---|---|---|---|
|  | 134 | 5 | 3 |
|  | 136 | 3 | 0 |
|  | 138 | 3 | 0 |
| D6S1001 | 176 | 18 | 8 |
|  | 178 | 12 | 4 |
|  | 180 | 40 | 79 |
|  | 182 | 11 | 4 |
|  | 184 | 4 | 0 |
|  | 186 | 1 | 0 |
|  | 188 | 2 | 0 |
|  | 190 | 5 | 4 |
|  | 192 | 6 | 1 |
|  | 196 | 1 | 0 |
|  | 200 | 2 | 0 |
| 65-1 | 218 | 1 | 0 |
|  | 216 | 6 | 1 |
|  | 214 | 8 | 1 |
|  | 212 | 11 | 3 |
|  | 210 | 33 | 8 |
|  | 208 | 31 | 11 |
|  | 206 | 8 | 72 |
|  | 204 | 1 | 3 |
|  | 202 | 1 | 2 |
|  | 198 | 0 | 1 |
| 65-2 | 173 | 1 | 0 |
|  | 169 | 9 | 3 |
|  | 167 | 3 | 3 |
|  | 165 | 0 | 1 |
|  | 163 | 1 | 1 |
|  | 161 | 45 | 12 |
|  | 159 | 38 | 81 |
|  | 151 | 1 | 1 |
|  | 141 | 1 | 0 |
|  | 131 | 1 | 0 |
| 63-2 | 133 | 24 | 5 |
|  | 131 | 24 | 7 |
|  | 129 | 2 | 1 |
|  | 127 | 4 | 0 |
|  | 123 | 6 | 2 |
|  | 119 | 0 | 1 |
|  | 117 | 0 | 1 |
|  | 113 | 41 | 85 |
| 63-3 | 171 | 3 | 1 |
|  | 169 | 49 | 90 |
|  | 167 | 49 | 7 |
| 373-8 | 163 | 0 | 1 |
|  | 161 | 2 | 1 |
|  | 159 | 1 | 1 |
|  | 157 | 5 | 1 |
|  | 155 | 12 | 5 |
|  | 153 | 29 | 12 |
|  | 151 | 17 | 69 |
|  | 149 | 21 | 7 |
|  | 147 | 11 | 5 |
|  | 145 | 1 | 0 |
|  | 139 | 0 | 1 |
| 373-29 | 117 | 0 | 1 |
|  | 115 | 1 | 4 |
|  | 113 | 5 | 55 |
|  | 111 | 1 | 7 |
|  | 109 | 17 | 6 |
|  | 107 | 20 | 6 |
|  | 105 | 7 | 1 |
|  | 103 | 48 | 19 |
|  | 101 | 1 | 0 |
|  | 83 | 0 | 1 |
| 68-1 | 171 | 1 | 0 |
|  | 169 | 10 | 12 |
|  | 167 | 52 | 59 |
|  | 165 | 1 | 0 |
|  | 163 | 35 | 29 |
| 241-6 | 115 | 1 | 0 |
|  | 113 | 1 | 1 |
|  | 109 | 4 | 0 |
|  | 107 | 27 | 5 |
|  | 105 | 24 | 80 |
|  | 103 | 10 | 2 |
|  | 101 | 6 | 3 |
|  | 99 | 8 | 1 |
|  | 95 | 0 | 1 |
|  | 93 | 18 | 7 |
|  | 87 | 0 | 1 |
| 241-29 | 121 | 0 | 1 |
|  | 119 | 0 | 1 |
|  | 117 | 20 | 5 |
|  | 115 | 27 | 4 |
|  | 113 | 11 | 82 |
|  | 111 | 0 | 1 |
|  | 103 | 42 | 7 |

With respect to HH, the haplotypes for many of the single chromosomes were obtained from the DNA of cell hybrid lines, each of which contained a single chromosome 6 from an HH-affected individual (Shay, J. W. *Techniques in Somatic Cell Genetics*, Plenem, New York, 1982). These results are shown as "% HH" in Table 2. For each marker, generally one allele was more common in HH chromosomes as compared to normal individuals.

EXAMPLE 3

Determination of Haplotypes Associated with HH

Table 3 shows a compilation of haplotypes assembled from the alleles most commonly occurring in HH chromosomes. Haplotype A assembles six of the ten markers; haplotypes B and C expand the assembly with one additional marker each and haplotype D adds two additional markers for a total of eight.

TABLE 3

6p Marker Haplotype Associations with HH

| Markers | D6S258 | 19D9 | 18B4 | 1A2 | 2B8 | D6S306 | 1E4 | 24E2 |
|---|---|---|---|---|---|---|---|---|
| Haplotype A |  | 205 | 235 | 239 |  | 238 | 271 | 245 |
| Haplotype B |  | 205 | 235 | 239 | 206 | 238 | 271 | 245 |
| Haplotype C | 199 | 205 | 235 | 239 |  | 238 | 271 | 245 |
| Haplotype D | 199 | 205 | 235 | 239 | 206 | 238 | 271 | 245 |

Table 4 shows the distribution of these haplotypes as determined in 74 hemochromatosis chromosomes and 56 chromosomes from unaffected individuals. Inheritance patterns could be used to associate the haplotypes with particular chromosomes in the CEPH individuals and HH individuals.

TABLE 4

Frequency of Haplotypes in Affected and Unaffected: (%)

| | Individuals | | Chromosomes | |
|---|---|---|---|---|
| | Affected | Unaffected | Affected | Unaffected |
| A | 89 | 0 | 68 | 0 |
| B | 86 | 0 | 58 | 0 |
| C | 84 | 0 | 61 | 0 |
| D | 81 | 0 | 51 | 0 |

Table 4 clearly shows that none of the haplotypes A–D occurs in unaffected individuals or in unaffected chromosomes tested to date. A very high percentage of individuals affected by HH contains haplotype A and significant numbers contain B–D. Indeed, these haplotypes are present on a majority of chromosomes from HH-affected individuals.

EXAMPLE 4

Single Base-Pair Polymophisms In the course of sequencing the HH region of genomic DNA prepared as described in Example 1, and by comparing the sequences obtained for DNA from affected as compared to unaffected individuals, three single base-pair polymorphisms were found and designated HHP-1, HHP-19 and HHP-29 as follows:

HHP-1

Unaffected sequence: (SEQ ID NO:73)
TCTTTTCAGAGCCACTCACgCTTCCAGAGAAAGAGCCT
Affected sequence: (SEQ ID NO:74)
TCTTTTCAGAGCCACTCACACTTCCAGAGAAAGAGCCT

HHP-19

Unaffected sequence: (SEQ ID NO:75)
ATATATCTATAATCTATATTTCTTAAGACAATTAAGAATG
Affected sequence: (SEQ ID NO:76)
ATATATCTATAATCTATATTTCTTGAGACAATTAAGAATG

HHP-29

Unaffected sequence: (SEQ ID NO:77)
TTGGGGATTTTATAGATTTTATTTTTAAAAAATGTTTAATCTTTGT
Affected sequence: (SEQ ID NO:78)
TTGGGGATTTTATAGATTTTAGTTTTAAAAAATGTTTAATCTTTGT The presence or absence of these single base-pair sequence differences can, of course, be determined in the same DNA samples as those which provide information on the $(CA)_n$ repeat alleles by use of the appropriate primers for amplification and sequencing. FIG. 2 shows the sequences of primers used for amplification and sequencing of the above three base-pair polymorphisms. The amplification primers for HHP-1 are labeled AG77 and AG78; the amplification primers for HHP-19 are labeled AG110 and AG111; and the amplification primers for HHP-29 are labeled AG165 and AG166. The primers used in the sequence determination by OLA are designated, for HHP-1, AG64, AG62 and AG63; for HHP-19, AG143, AG144 and AG145; and for HHP-29 are designated AG190, AG191 and AG192. As indicated in the sequences shown, "bio" indicates biotin coupling; "dig" indicates coupled digoxygenin.

Table 5 shows the frequency of these point mutations in affected and unaffected chromosomes:

TABLE 5

Frequencies of Alleles as % of Chromosomes Tested

| | Affected Chromosomes | Random Chromosomes |
|---|---|---|
| HHP-1 A | 64% | 6% |
| G | 36% | 94% |
| HHP-19 G | 64% | 6% |
| A | 36% | 94% |
| HHP-29 G | 64% | 6% |
| T | 36% | 94% |

The allele in HHP-1:A occurs in 64% of the affected chromosomes; its occurrence at 6% in random chromosomes approximates the estimated frequency of the common HH mutation in the population. As noted hereinabove, according to the results obtained to date, the presence of HHP-1:A is associated with the presence of HHP-19:G and HHP-29:G.

We claim:

1. A method to determine the likelihood of the presence or absence of common hereditary hemochromatosis (HH) in an individual comprising the steps of:
   (a) obtaining genomic DNA from said individual;
   (b) amplifying a HH-associated microsatellite marker with a primer pair selected from the group consisting of SEQ ID NOS. 31 and 32; SEQ ID NOS. 33 and 34; SEQ ID NOS. 35 and 36; SEQ ID NOS. 37 and 38; SEQ ID NOS. 39 and 40; SEQ ID NOS. 41 and 42; SEQ ID NOS. 43 and 44; SEQ ID NOS. 45 and 46; SEQ ID NOS.47 and 48; SEQ ID NOS. 49 and 50; SEQ ID NOS. 51 and 52; SEQ ID NOS. 53 and 54; SEQ ID NOS. 55 and 56; SEQ ID NOS. 57 and 58; SEQ ID NOS. 59 and 60; SEQ ID NOS. 61 and 62; SEQ ID NOS. 63 and 64; SEQ ID NOS. 65 and 66; SEQ ID NOS. 67 and 68; SEQ ID NOS. 69 and 70; SEQ ID NOS. 71 and 72;
   wherein said amplifying step further comprises the optional step of amplifying said DNA with a primer pair selected from the group consisting of SEQ ID NOS. 21 and 22; SEQ ID NOS. 23 and 24; SEQ ID NOS. 25 and 26; SEQ ID NOS. 27 and 28; and SEQ ID NOS. 29 and 30; and
   (c) determining the presence or absence of said microsatellite marker, wherein the presence of said microsatellite marker is indicative of the likely presence of HH in the individual and absence of said microsatellite marker is indicative of the likely absence of HH in the individual.

2. The method of claim 1 wherein said method tests at least two of said markers.

3. The method of claim 2 wherein said method tests at least three of said markers.

4. The method of claim 3 wherein said method tests at least four of said markers.

5. The method of claim 1 wherein said genomic DNA is prepared from a sample of blood or buccal swab from said individual.

6. A method to identify a potential reduced responsiveness of a subject to interferon treatment for hepatitis C, which method comprises determining the presence or absence of a marker for the common hereditary hemochromatosis in said subject according to the method of claim 1, wherein the presence of one of the HH markers indicates a probable reduced responsiveness to said interferon treatment.

7. The method of claim 1 which further comprises the amplification of a microsatellite marker using a pair of DNA primers selected from the group consisting of SEQ ID NOS. 21 and 22; SEQ ID NOS. 23 and 24; SEQ ID NOS. 25 and 26; SEQ ID NOS. 27 and 28; and SEQ ID NOS. 29 and 30.

8. A method to determine the presence or absence of common hereditary hemochromatosis (HH) in an individual which comprises:
   (a) obtaining genomic DNA from said individual;
   (b) amplifying a HH-associated allele selected from the group consisting of : HHP-1, HHP-19G, and HHP-29G; and
   (c) determining the presence or absence of at least one HH-associated microsatellite marker in said individual using a primer pair selected from the group consisting of SEQ ID NOS. 31 and 32; SEQ ID NOS. 33 and 34; SEQ ID NOS. 35 and 36; SEQ ID NOS. 37 and 38; SEQ ID NOS. 39 and 40; SEQ ID NOS. 41 and 42; SEQ ID NOS. 43 and 44; SEQ ID NOS. 45 and 46; SEQ ID NOS. 47 and 48; SEQ ID NOS. 49 and 50; SEQ ID NOS. 51 and 52; SEQ ID NOS. 53 and 54; SEQ ID NOS. 55 and 56; SEQ ID NOS. 57 and 58; SEQ ID NOS. 59 and 60; SEQ ID NOS. 61 and 62; SEQ ID NOS. 63 and 64; SEQ ID NOS. 65 and 66; SEQ ID NOS. 67 and 68; SEQ ID NOS. 69 and 70; SEQ ID NOS. 71 and 72;
   wherein the presence of said HH-associated allele in combination with at least one microsatellite marker indicates the likely presence of HH in the individual and the absence of said HH-associated allele and said microsatellite marker indicates the likely absence of HH in the individual.

9. A method to identify a potential reduced responsiveness of a subject to interferon treatment for hepatitis C, which method comprises determining the presence or absence of a marker for the common hereditary hemochromatosis in said subject according to the method of claim 8, wherein the presence of one of the HH markers indicates a probable reduced responsiveness to said interferon treatment.

10. A pair of primers of about 18 nucleotides in length wherein said primers specifically amplify a common hereditary hemochromatosis (HH) associated marker selected from the group consisting of SEQ ID NO. 85; SEQ ID NO. 86; SEQ ID NO. 87; SEQ ID NO. 88; SEQ ID NO. 89; SEQ ID NO. 90; SEQ ID NO. 91; SEQ ID NO. 92; SEQ ID NO. 93; SEQ ID NO. 94; SEQ ID NO. 95; SEQ ID NO. 96; SEQ ID NO. 97; SEQ ID NO. 98; SEQ ID NO. 99; SEQ ID NO. 100; SEQ ID NO. 101; SEQ ID NO. 102; SEQ ID NO. 103; SEQ ID NO. 104; SEQ ID NO. 105; SEQ ID NO. 106; SEQ ID NO. 107; SEQ ID NO. 108; and SEQ ID NO. 109.

11. A DNA primer pair for amplification of a microsatellite marker associated with common hereditary hemochromatosis (HH) wherein the sequences of said primers are selected from the group consisting of SEQ ID NOS. 31 and 32; SEQ ID NOS. 33 and 34; SEQ ID NOS. 35 and 36; SEQ ID NOS. 37 and 38; SEQ ID NOS. 39 and 40; SEQ ID NOS. 41 and 42; SEQ ID NOS. 43 and 44; SEQ ID NOS. 45 and 46; SEQ ID NOS. 47 and 48; SEQ ID NOS. 49 and 50; SEQ ID NOS. 51 and 52; SEQ ID NOS. 53 and 54; SEQ ID NOS. 55 and 56; SEQ ID NOS. 57 and 58; SEQ ID NOS. 59 and 60; SEQ ID NOS. 61 and 62; SEQ ID NOS. 63 and 64; SEQ ID NOS. 65 and 66; SEQ ID NOS. 67 and 68; SEQ ID NOS. 69 and 70; and SEQ ID NOS. 71 and 72.

12. A kit for detection for the presence or absence of an hereditary hemochromatosis (HH)-associated microsatellite marker in an individual comprising:

(a) at least one pair of primers of about 18 nucleotides in length, wherein said primer pairs specify amplify said (HH)-associated microsatellite marker selected from the group consisting of SEQ ID NO. 85; SEQ ID NO. 86; SEQ ID NO. 87; SEQ ID NO. 88; SEQ ID NO. 89; SEQ ID NO. 90; SEQ ID NO. 91; SEQ ID NO. 92; SEQ ID NO. 93; SEQ ID NO. 94; SEQ ID NO. 95; SEQ ID NO. 96; SEQ ID NO. 97; SEQ ID NO. 98; SEQ ID NO. 99; SEQ ID NO. 100; SEQ ID NO. 101; SEQ ID NO. 102; SEQ ID NO. 103; SEQ ID NO. 104; SEQ ID NO. 105; SEQ ID NO. 106; SEQ ID NO. 107; SEQ ID NO. 108; and SEQ ID NO. 109; and optionally, a primer pair selected from the group consisting of SEQ ID NOS. 31 and 32; SEQ ID NOS. 33 and 34; SEQ ID NOS. 35 and 36; SEQ ID NOS. 37 and 38; SEQ ID NOS. 39 and 40; SEQ ID NOS. 41 and 42; SEQ ID NOS. 43 and 44; SEQ ID NOS. 45 and 46; SEQ ID NOS. 47 and 48; SEQ ID NOS. 49 and 50; SEQ ID NOS. 51 and 52; SEQ ID NOS. 53 and 54; SEQ ID NOS. 55 and 56; SEQ ID NOS. 57 and 58; SEQ ID NOS. 59 and 60; SEQ ID NOS. 61 and 62; SEQ ID NOS. 63 and 64; SEQ ID NOS. 65 and 66; SEQ ID NOS. 67 and 68; SEQ ID NOS. 69 and 70; and SEQ ID NOS. 71 and 72.

13. The kit of claim 12 which further comprises a pair of primers selected from the group consisting of SEQ ID NOS. 21 and 22; SEQ ID NOS. 23 and 24; SEQ ID NOS. 25 and 26; SEQ ID NOS. 27 and 28; and SEQ ID NOS. 29 and 30.

* * * * *

SEQUENCE LISTING ( 1 ) GENERAL INFORMATION:

( i i i ) NUMBER OF SEQUENCES: 124

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

AGTCATCTGA AGAGTTGG 18

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GCATGTCTTC TTTGTTAAGG 20

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

AATCAAGTTC TAGGCACC 18

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GAATGGAGGG AGTTTATG 18

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CTGTTTACAT CGGGAAGAGA CTTAG 25

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear (x i) SEQUENCE DESCRIPTION: SEQ ID NO:6:

CGAATAGTGT TAAAATTTAA GCTAGGGCTG    30

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (x i) SEQUENCE DESCRIPTION: SEQ ID NO:7:

CTATGGATCT TATTGTGCCT    20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (x i) SEQUENCE DESCRIPTION: SEQ ID NO:8:

TACAGGGAGT CTACAGGACC    20

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (x i) SEQUENCE DESCRIPTION: SEQ ID NO:9:

AGACTTTCAA AAACTCACAA TCAC    24

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (x i) SEQUENCE DESCRIPTION: SEQ ID NO:10:

GATAGAACAT TAGCTTAGAC ATGG    24

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (x i) SEQUENCE DESCRIPTION: SEQ ID NO:11:

GAAGGACTTG AAAGGAATAC    20

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (x i) SEQUENCE DESCRIPTION: SEQ ID NO:12:

```
GGAATTTGAA GCTACAGTG                                                                    19
```

( 2 ) INFORMATION FOR SEQ ID NO:13:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

```
TTTGGGTTTA TTGCCTGCCT CC                                                                22
```

( 2 ) INFORMATION FOR SEQ ID NO:14:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

```
AACAATGCCC TTCCTTTC                                                                     18
```

( 2 ) INFORMATION FOR SEQ ID NO:15:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

```
AACCCAGAAT CACATCTAGT GAGG                                                              24
```

( 2 ) INFORMATION FOR SEQ ID NO:16:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

```
TGATGCATAT GGCCTTTTCT TCTC                                                              25
```

( 2 ) INFORMATION FOR SEQ ID NO:17:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:17:

```
ATGCTGTTAT TTTTTCACTT TTTCCTG                                                           27
```

( 2 ) INFORMATION FOR SEQ ID NO:18:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:18:

```
AGTACTCTGT TGCAGTGAGA GATG                                                              24
```

( 2 ) INFORMATION FOR SEQ ID NO:19:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:19:

ATAGACACTG ACATCATCCC TACC    24

( 2 ) INFORMATION FOR SEQ ID NO:20:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

GTTTCTCTC CAGGACAAAT TTACC    25

( 2 ) INFORMATION FOR SEQ ID NO:21:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

TTTACTTCTG TTGCCTTAAT G    21

( 2 ) INFORMATION FOR SEQ ID NO:22:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

TGAGAGTTTC AGTGAGCC    18

( 2 ) INFORMATION FOR SEQ ID NO:23:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:23:

GCAAATCAAG AATGTAATTC CC    22

( 2 ) INFORMATION FOR SEQ ID NO:24:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:24:

CTTCCAATCC ATAAGCATGG    20

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

GCCCTATAAA ATCCTAATTA AC    22

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

GAAGGAGAAT TGTAATTCCG    20

( 2 ) INFORMATION FOR SEQ ID NO:27:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

TCTGGGATTC CTGTCCAATG    20

( 2 ) INFORMATION FOR SEQ ID NO:28:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

CCTGACATAT AGTAGGCACT C    21

( 2 ) INFORMATION FOR SEQ ID NO:29:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

TGCTCCATTG CACTCC    16

( 2 ) INFORMATION FOR SEQ ID NO:30:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

CTGATCACCC TCGATATTTT AC    22

( 2 ) INFORMATION FOR SEQ ID NO:31:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:31:

GTTGGAGAGA TAGGTGTTCT TTTCC 25

( 2 ) INFORMATION FOR SEQ ID NO:32:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:32:

CCTGTACTAC CCAAGCACCT GC 22

( 2 ) INFORMATION FOR SEQ ID NO:33:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:33:

GGGTTAAATC TCATCCGCG GC 22

( 2 ) INFORMATION FOR SEQ ID NO:34:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:34:

GGCTGCAGGA ACTGGGGAGG G 21

( 2 ) INFORMATION FOR SEQ ID NO:35:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:35:

ACTCCAGCCT GGGCAATAGA GC 22

( 2 ) INFORMATION FOR SEQ ID NO:36:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:36:

ACTCTTCGGT GTGGCAATCC GC 22

( 2 ) INFORMATION FOR SEQ ID NO:37:

( i ) SEQUENCE CHARACTERISTICS:
  ( A ) LENGTH: 28 base pairs ( B ) TYPE: nucleic acid
( C ) STRANDEDNESS: single
( D ) TOPOLOGY: linear ( x i ) SEQUENCE DESCRIPTION: SEQ ID NO:37:

AATAATGTTA AGTAACAAAC TAGAGTAC     28

( 2 ) INFORMATION FOR SEQ ID NO:38:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:38:

ACTCCAGCCT GGGCAATAGA GC     22

( 2 ) INFORMATION FOR SEQ ID NO:39:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:39:

TCATAAAACT CTACCAACAT ATCTCC     26

( 2 ) INFORMATION FOR SEQ ID NO:40:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:40:

GGAATTCCTG TGTGAAGAAA TAAACC     26

( 2 ) INFORMATION FOR SEQ ID NO:41:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:41:

TTCTGCCAAC CAAATTCAAG ACTATC     26

( 2 ) INFORMATION FOR SEQ ID NO:42:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:42:

GCAGAAAAAT GTTTAATTCA GGAGGG     26

( 2 ) INFORMATION FOR SEQ ID NO:43:

( i ) SEQUENCE CHARACTERISTICS:
( A ) LENGTH: 26 base pairs
( B ) TYPE: nucleic acid
( C ) STRANDEDNESS: single ( D ) TOPOLOGY: linear ( x i ) SEQUENCE DESCRIPTION: SEQ ID NO:43:

AGTCTTTGTG TAAGCATATA TAAGCC                                                      26

( 2 ) INFORMATION FOR SEQ ID NO:44:

( i ) SEQUENCE CHARACTERISTICS:
              ( A ) LENGTH: 24 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:44:

CATACCGTGC AGAATCTGAA CTGG                                                        24

( 2 ) INFORMATION FOR SEQ ID NO:45:

( i ) SEQUENCE CHARACTERISTICS:
              ( A ) LENGTH: 27 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:45:

AAAACATATA AGTGTTTTCA GAGAAGG                                                     27

( 2 ) INFORMATION FOR SEQ ID NO:46:

( i ) SEQUENCE CHARACTERISTICS:
              ( A ) LENGTH: 25 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:46:

GTCTAGGCCA TTTTGTCATT TAGGC                                                       25

( 2 ) INFORMATION FOR SEQ ID NO:47:

( i ) SEQUENCE CHARACTERISTICS:
              ( A ) LENGTH: 22 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:47:

CCCCTCCTCC TGCTTTTTCT CC                                                          22

( 2 ) INFORMATION FOR SEQ ID NO:48:

( i ) SEQUENCE CHARACTERISTICS:
              ( A ) LENGTH: 27 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:48:

TTATTTACAT TTGAAGGAAT GGAAACC                                                     27

( 2 ) INFORMATION FOR SEQ ID NO:49:

( i ) SEQUENCE CHARACTERISTICS:
              ( A ) LENGTH: 24 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:49:

GCTTTTCAAT CACTGCTTCC CTCC                                              24

( 2 ) INFORMATION FOR SEQ ID NO:50:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

AGAGAAGGAG TGGACATATG GTGG                                              24

( 2 ) INFORMATION FOR SEQ ID NO:51:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

GGCTTCATTA ATTACATTGT TTTTCAAG                                          28

( 2 ) INFORMATION FOR SEQ ID NO:52:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

CAGCCTGGGA GACAGAGTGA GG                                                22

( 2 ) INFORMATION FOR SEQ ID NO:53:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

CCACAACCAG ATGTCTCCTG CG                                                22

( 2 ) INFORMATION FOR SEQ ID NO:54:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

GCACCTTCCA GAGAAGTTAG CCG                                               23

( 2 ) INFORMATION FOR SEQ ID NO:55:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

TGTATGGGGT AAATCCAAGT TGCC                                                          24

( 2 ) INFORMATION FOR SEQ ID NO:56:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

ACAAATAGAG AAAGTTATCT TTAGAGG                                                       27

( 2 ) INFORMATION FOR SEQ ID NO:57:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

TGTGTTTCAG TCAGCTATTG CTCC                                                          24

( 2 ) INFORMATION FOR SEQ ID NO:58:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:58:

TGTACTTACA TCTTAAGGTA CAGCC                                                         25

( 2 ) INFORMATION FOR SEQ ID NO:59:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:59:

CTCCAGGCTG GCCGACAAAA GC                                                            22

( 2 ) INFORMATION FOR SEQ ID NO:60:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:60:

ATGTATATTA CAGCTTTTAT AATTGTCC                                                      28

( 2 ) INFORMATION FOR SEQ ID NO:61:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:61:

TCACAATCAT TTTTTGATAG CCTATCC                                                       27

( 2 ) INFORMATION FOR SEQ ID NO:62:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:62:

AGCCTTTAGG TATTTTCACA CTTGC     25

( 2 ) INFORMATION FOR SEQ ID NO:63:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:63:

CCAGCTCATT AGTCTTTCTT GTAGC     25

( 2 ) INFORMATION FOR SEQ ID NO:64:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:64:

ACTGAGATCA TTTACTGTTA CTAGAC     26

( 2 ) INFORMATION FOR SEQ ID NO:65:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:65:

GTTCATTCCA TTTCAGGCAT ATTCG     25

( 2 ) INFORMATION FOR SEQ ID NO:66:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:66:

ATTAGTAGAA AGATTTAGAG TAAATGC     27

( 2 ) INFORMATION FOR SEQ ID NO:67:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:67:

CTTGATTCTG ATTCACATTT GACTCC     26

( 2 ) INFORMATION FOR SEQ ID NO:68:

( i ) SEQUENCE CHARACTERISTICS:
   ( A ) LENGTH: 27 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:68:

TATTATATGT CATCAGAAGT ATTAGGG  27

( 2 ) INFORMATION FOR SEQ ID NO:69:

( i ) SEQUENCE CHARACTERISTICS:
   ( A ) LENGTH: 22 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:69:

GCAATGACAC CCTCCCATCA CC  22

( 2 ) INFORMATION FOR SEQ ID NO:70:

( i ) SEQUENCE CHARACTERISTICS:
   ( A ) LENGTH: 25 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:70:

TATCAGATGA CATTTTAGGA GACCC  25

( 2 ) INFORMATION FOR SEQ ID NO:71:

( i ) SEQUENCE CHARACTERISTICS:
   ( A ) LENGTH: 28 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:71:

CCTATACAAT AAATCTATAA AAAGTGGG  28

( 2 ) INFORMATION FOR SEQ ID NO:72:

( i ) SEQUENCE CHARACTERISTICS:
   ( A ) LENGTH: 24 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:72:

ATTCCTGTGT CTTTCCAGAA CACC  24

( 2 ) INFORMATION FOR SEQ ID NO:73:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:73:

TCTTTTCAGA GCCACTCACG CTTCCAGAGA AAGAGCCT  38

( 2 ) INFORMATION FOR SEQ ID NO:74:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:74:

TCTTTTCAGA GCCACTCACA CTTCCAGAGA AAGAGCCT    38

(2) INFORMATION FOR SEQ ID NO:75:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO:75:

ATATATCTAT AATCTATATT TCTTAAGACA ATTAAGAATG    40

(2) INFORMATION FOR SEQ ID NO:76:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO:76:

ATATATCTAT AATCTATATT TCTTGAGACA ATTAAGAATG    40

(2) INFORMATION FOR SEQ ID NO:77:

(i) SEQUENCE CHARACTERISTICS:
(A) LENGTH: 46 base pairs
(B) TYPE: nucleic acid
(C) STRANDEDNESS: single
(D) TOPOLOGY: linear (xi) SEQUENCE DESCRIPTION: SEQ ID NO:77:

TTGGGGATTT TATAGATTTT ATTTTAAAA AATGTTTAAT CTTTGT    46

(2) INFORMATION FOR SEQ ID NO:78:

(i) SEQUENCE CHARACTERISTICS:
(A) LENGTH: 46 base pairs
(B) TYPE: nucleic acid
(C) STRANDEDNESS: single
(D) TOPOLOGY: linear (xi) SEQUENCE DESCRIPTION: SEQ ID NO:78:

TTGGGGATTT TATAGATTTT AGTTTAAAA AATGTTTAAT CTTTGT    46

(2) INFORMATION FOR SEQ ID NO:79:

(i) SEQUENCE CHARACTERISTICS:
(A) LENGTH: 1260 base pairs
(B) TYPE: nucleic acid
(C) STRANDEDNESS: single
(D) TOPOLOGY: linear (xi) SEQUENCE DESCRIPTION: SEQ ID NO:79:

AGCTATACTA AAATTCTTCA GCTTTCATTT TTGGGCCCAT GCTTAGTATT GTTAAAAACT    60

TATTTGTAGA ACATTCATGT TTTGATATA AATTGTATGA ATACAATTTA TTTCAAAACA    120

TTTCCTTTGG CTGAAAACGC CATAGCCTTA AGAAAACTTT ATTAAAAGA CAAAGTCTTT    180

CAGACATTTG CAAAAATGCA TCAGTAATAA CCCTAATTCA TCACACTGGA TAAAATTTCT    240

-continued

```
ATCTGGTTAA GATTTCATCA CTTCAAGCTA AAGCGGAAGA AGGAGGTTTT TATATTGATA     300

TTGGAAAAGT CCTTGATTGT ATTGGATGCC ATTATTCTTA TCTCTAAACA TGAACTGATG     360

TCACCATTTC TTTATATCAG TCTCAGTTTT GATAACAAAT TGACTCTCTT AAACTTCTTA     420

AGCAGATTGA TAATTCATGC ACTTCCTTGT ATCCAGTGAC TCTAATCTTA AACAAATGGA     480

ACATAAAATA CTGAACCAAT TAGCAAAATG AACTGTTTCT TAAACGTTTA TAACAATCTA     540

TGGATCTTAT TGTGCCTAAA TAGATTAATC ATTTTAATTT TTTTAAAAAT TTAAAATTTC     600

TCTAAAGTTT TCTTTTGCTT TCTAGATACA CAAATTACAC ACACACAC ACACACAC         660

ACAAACACAC ACACAGTGGC AATTAAATAT TCGTGCCTTG AAAAGTGAGA AAGGATACAG     720

ATGTCCTTCT GCCTAGTAGA CCTGTTTATG AGAGGTCCTG TAGACTCCCT GTACTCACTT     780

GACTCCCAAA TTCATTACCT CTATCAACCC AAATATGCTC CTTTCCTTC TGTGTATCTA      840

CTTCATTAAA CATCTGTGCA ATCAGCCAGA CACAAACTTG CAGACCCCGC CTCACCACTC     900

TCCTGCCTCT TATCTGATAA ATCTCCCAGT GCCGCAAATT CTCCCTCTAG CCCGGCTTGT     960

TCATCTGTAC ACTTGCCTTT ATTACAGCTC TCATACCATA GCAGATCACC ACTGCTTTTC    1020

TCCTAGATTA CTGCAGCCAT CTCCTGTTTG TCTCTCATTT TCCAGTATCA CTCTCTTCTA    1080

ATTTGCTGCA GCTGGAGTTA GGTTCTAAAT TCCAAATTCA TTCATGTATC TACTTTAAAT    1140

AACTCAGTAC TTCTTTTTG TTTGTTTGTT TTTCATAATG ACAAACTCC TTAACATGAG       1200

CTACAAGATC ATGCATATTC TGGTCCCTAT TCCTTAACTA GTCAGAGTGA ATGTCATTCC    1260
```

( 2 ) INFORMATION FOR SEQ ID NO:80:

( i ) SEQUENCE CHARACTERISTICS:
        ( A ) LENGTH: 1260 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:80:

```
GTAATAAAAT TATTTAGGGT TTTGGATTGT GTCAAAGCCC TATTCAGCAA TGTCTACTTG      60

AAAATTTCAT TGAAAAAGTA ACTTAAATAA AGTAGCTATT TGAAGGGCTC AGTAGGATAG     120

AACCCTTGTC CTTAGCATGA ATCATAGTGA GAAGACACTT TTGAATATGT TTGTTTTTCT     180

TCTATTACCA GGAAAACATA GGATCATAAA TCACAATTAT TCCATATGTT TTAGAAATTA    240

ATCATGTGTA TCTTTGCACA AGCACCATAA TGCTTGTGTG TATAAATGAG TATGCATGCA     300

TACTTGTAAA CACACAGCTT TCATACTCGC TTTTATTATT GTCACTTTTA ACAGCCCCTT     360

ACATGAAATT TATATTTAAA AAGTGAGAAC ATTTATATTC ATTCTGATGT ATTCAGACAC     420

TTGTATTAAA TTCTTAGCTC TACTATTTGT GGTCTGTTTG ATAATGTTTC CTAATCTATC     480

AAATGAAAGG ATTCTGAATT GATCATTTGT TTTCAAATGT ATATTCATGT TAGAATCTCA     540

CAAGGAGCTT TTTCAACAAA ATATTTCCAG ACTTTCAAAA ACTCACAATC ACTGTGGTTG     600

GAACTTGAAA CAAACATATG TGTGTCTGTG TGTGTATATA TATATATATA CACACACACA     660

GACACACATA TATATATCTT TATGTAATTT TAATGCAGCT GATCAGTGAA ACAGTGTTAA     720

GCTCAAAAAT TTAATGATG TCATTTTCCA TGTCTTCACT AACCTTCTCT CTTCTCCTTT      780

TCTCTCTTTT CCTTCCTACC AAATTTTTTC CTACCTATTT TTACTCTCCA TTTTCTCACT     840

CCCCTTTAAC TCATTTCCAT TACACAAACT ACTATTACAC AAACTACTCA TATAATTTTT    900

CCTCATCTTA TCTTCCCAAA GCATAACTTC TGTCAGTCAA TCCACAGTAC TAAAGCATTG    960

ATTTATGGTT CTGTTGGATT TTAATTAGCT GTGGTCAATT TGGAAAGGAG GAGAAAAAAT   1020

GATTTGACAT GTCAGATACA ACATGTTATA CAGATTAAAT TTCAGCTGTA ATCTAACTAG   1080
```

| | | | | | |
|---|---|---|---|---|---|
| TCATCAGCAT | TTTATTCAGG | GCTTTACAAT | AAGTATTCCC | AAGTTCTGCC | TCTGTAGGTT | 1140 |
| TGTATTGGGT | AGGTAGGAAT | ATTTAAATGA | ATTTGAAGT | TTCACTTCAA | GAATTATTTA | 1200 |
| TTTCTATTAA | ATAAGTAAAG | AAGCAGTCTC | AAGAGCAGTC | ACTGTCACTG | TGTTTCTAG | 1260 |

( 2 ) INFORMATION FOR SEQ ID NO:81:

( i ) SEQUENCE CHARACTERISTICS:
        ( A ) LENGTH: 1050 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:81:

| | | | | | |
|---|---|---|---|---|---|
| TTGTTCTGTG | CCTTAGCTTT | ATTTCCAAAG | TTCCAGAAAA | GACAAGTCAC | AGATCGGGAG | 60 |
| AAAATATTTG | CAAAACATAT | ATACCATGAC | CCATGAGGCC | CCTCCTCTGC | CACTGCCACT | 120 |
| GCCACTGCCA | CTGAGATGGT | GTATCTCACT | TCCTACCTAT | TACCTTCCCT | CATGAGCAAC | 180 |
| ACCTCCCTTA | GTGCCAAGGA | CATTAAGAAG | ATCCTGGACA | GAGTAGGCAT | GGAGGCAACT | 240 |
| GATGACTGGC | TAAACAAGGT | TATCAGTGAG | CTGAATGGAA | AAAATATTGA | AGATATCATT | 300 |
| GCCCAAGGTA | TTGGTGAGCT | TGCCAGTGTG | CCTGCTGGTG | GGCTGTGGC | CCTCTCTGCT | 360 |
| TCTCTGGGCT | CTGCAGGTCC | TGCTGCTGGT | TCTACCCCTG | CTGCAGAAGA | AAGATGACAA | 420 |
| GAAGGAGGAG | TCATCTGAAG | AGTTGGCCTG | TTCAATTAAA | TTCCTGGTGT | CCTACAAACA | 480 |
| AAGCCTTTTC | ACATTAAAAA | AAAACAAACA | AACCAGTGTG | TGTGTGTGTG | TGTGTGTGTG | 540 |
| TGTGTGTAAT | AGAGGCTTTG | TATTCAAAAT | ATACAAAGAA | CTCCAAAGTT | CAACAATAAG | 600 |
| AAAACATGTA | AACCAATTAA | AAAATGGGCA | AAATATCTGA | ACTGACACCT | TAACAAAGAA | 660 |
| GACATGCAAA | TGGCAAATAA | GCATGTAAAA | AGATAGTCAA | TGTCATTTTT | TATTAGGAAA | 720 |
| TTGCAAACCA | GAAAACAGGG | AGATACCACT | ACATTCTTAT | TAGAATGGAC | TAAAATCTAA | 780 |
| AAAATCGACA | ATACCAATTG | CTAGCAAGGA | TGCGGAGTGG | CAGAAAGTCT | CATTTATTTC | 840 |
| TTGTGAGATG | CAGAAGAGTA | CATCAATTTC | CTGATCACTG | CAATTCATTC | CATGACCCAC | 900 |
| ATAGATATTT | TTCTCCCCAT | ATGTTAGGGA | AGCAGATCTC | TCATGGTCTT | CATGGACTTC | 960 |
| TCTTTCTGAG | TGGAAATTCA | CAAGGGTATC | TTCTAGTTAT | CTATTCCAAT | CTCCCCCACC | 1020 |
| CTCATCTAGC | ATCTTGAAGG | GTCTTGGTTG | | | | 1050 |

( 2 ) INFORMATION FOR SEQ ID NO:82:

( i ) SEQUENCE CHARACTERISTICS:
        ( A ) LENGTH: 1380 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:82:

| | | | | | |
|---|---|---|---|---|---|
| CTGTAAAGTT | ACCATTTTTC | CTTTTTAAAT | TAATAATTAT | CTTGAGAGGG | AATATTTTGA | 60 |
| GATTATGAAA | ATATTCTGTT | TCTCATCATA | TTTTTGCTAC | TTATATTGAT | GTTCATCAGT | 120 |
| GATTCTTGCC | TGCAACAATT | ATTTCTGTAG | CATCTATTTT | CTATTTCTAT | TGCTAATTCT | 180 |
| ACATTTATTA | ATTGGAATTC | TACTGTAAAG | AAGAGCTGTT | ATTTTTCCCC | CATTTGTTAT | 240 |
| TTGTTCAGTC | ATTTATTTAA | ACTCATATAG | ACTTATGGGT | ATTTGTTTTA | TTCTATTGTT | 300 |
| TGTAGTCCCA | ATACTATCAT | TATTTAATTT | ACTGCTAAAA | TTGTCCTAGA | TTTGGCCTTT | 360 |
| GGGAGCTCCT | TCAAGTTGAC | TCATGTATCT | TTTTAACATG | CCCCATCACT | ATTTGAGAAC | 420 |
| TTCTATACTC | TGTGTCACCA | CCAGCTGTTC | TAGGGTCATC | TTGGACTTTT | ACTTCCCCAG | 480 |

-continued

```
CCCTGGAATT ACTAATTTTT CTAAGGATCC TTGGTTCCTT TTACTGGAAA TATATTTAGA      540
AATCAAGTTC TAGGCACCAG GTGTGTTCAT TGCTACTGAT TTGTTATTGC TTCCAGACTC      600
TCTCAGTGAA CAGAGCTTAC AAATAGAGTG TGTGTGTGTG TATATATATA TATATATATA      660
TATATATATA TACTGACATA TACATACACA TACATTTTTA TTTATATACC TAGCTGTGTG      720
TGTGTATGTG TGTGTGTGTG ACCACAGTTC ATACTAATGC CTCTGATTCC AATCCAAATA      780
CCACATAGTA TTTGCATAAA CTCCCTCCAT TCCTTATTTG TACCTTCTTT GTTGAACAGT      840
GGGAAATTTG GCTCTCATTA TCCATAATAT ATTTACTTAT TTTCTCAATT CTAATACACA      900
AATAGCTTTA GAATTGCTAA TCCACACTCT TGGGAATAAC CATTTTACTA ACTAGAGTAC      960
AATATTTCTG TACAGTTCTT TTTGCTTTTA TCCTTAGATG AGTCTATCCT TAGCAAAATA     1020
GTCAAGATAC TCTTTTTCCC AAAGTTAATT AGGTTAGTTT TTTTTCCTTC CTTACCCTCT     1080
TTAACTTGGT TTTGTTGCTC ATTTGTAATA CAGGTGGGTT AATTTATTAT TCTCTGTATT     1140
TCTTTTGGGT ACCTCCCATT CCGGTTGACT TTAGTTATTT ATTTAAATTG GAATATGTGA     1200
AGCATTACTA TGGCTATAAA AGTTAGAACA CACAAAATGT TATATGTACT TAGAAAAGTG     1260
TCACTCCCCC TCAGCCTTTC CATTCCACTA ATTCTCCCAT TTTTTTATAC TCTATTCCAA     1320
ATCACCACCT CCTCCAACCC TGTGGGTAAC TAATCTCATT AGTTTCTGGT TTATCATTCC     1380
```

( 2 ) INFORMATION FOR SEQ ID NO:83:

( i ) SEQUENCE CHARACTERISTICS:
        ( A ) LENGTH: 1260 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:83:

```
CCCAGAATTG GCCTTCCAAT GCACCAAAAA CTGTAATCAC AACATTTTCA AGGGTTGTCA       60
CACTTTACAT CAATGTTTGT ACAATTCAGT GTAAACTAGA CCTTTCTGAT CCAGAAATCA      120
TCTCTTCAGT AATACACACA CGCACACACA CATACATACA TACACACACA CACATAGAAA      180
CCAAGATGTA AAGGGAGCTT TGAGAGGTT GCTTGCAAGG GTGTTAATAA AAAAAAAAGG       240
AATTCTCAAA TTATAGGCCT TTTAAAGACT TCAATTTTAC ATAGCTTATA ATTTAATTCT      300
CTCCAAATTG CTTTATTATT ACTATTCTTA GAAAAACTAT TATAGTGATC TTCAAATAAA      360
ATGTCGACAG AGAACTATAT CTGTTTTCTA CTGCCTAAAT ATATTCATTG CACAAGTCTT      420
AAGAACTGAT CTTTTATGAA CTCTCAAAAT AGCATATCCT TGAAATCTTT AAGGTCTCAA      480
ACATCTTAGC ACTAGTCTGT ATACATCGGG AAGAGACTTA GACTTCTCTG AAACCAGAAT      540
AAAAGCCAGA AACAAAACAT TTGATACAT ATACACATGT CCTCATCCTT ACACACACAC       600
ACACACACAC ACACACACAC ACAAACTCCA TGGCACAAAT TATTTTCAG ACAATTGTAG       660
ATCTAACAGA AGTATCCAAA ACCTTGTCTT AATTTCTCT ATAAGTTTAA CAGCCCTAGC       720
TTAAATTTTA ACACTATTCG CACATCAACA CAATACTAAA ATCCACAACA ATTCTGCACT      780
CCCCAGTTTT ACTTAGATCT TCTGTTGTTT CTGTACTTCC CACTTCTAAG TTGAAGTGTC      840
CTATTCCATC TATCAAATAA AGTTGTAGCT ACATTTAGA CTGAAATCGA ATGCCTGCTT       900
TTGACCTTTT AAAATGATTC CTCTACTGTA TATATTATCT CTCTCCTTTT AACCTCGAAA      960
GCACTTATAG GGGCCGGGCG CGGTGGCTTA TGCCTGTAAT CCTAGCACTT GGGAGGCCG      1020
AGGCAGGCGG ATTGCCTGAG GTTAGGAGTT CAAGACCAGC CTGGGCAACA ATGGTGAAAC     1080
CCTGTCTCTA CTAAAATACA AAAATTAGCC AGGCATGACC GCGTGCGCCT GTAGTCCAG     1140
```

| | | | | | |
|---|---|---|---|---|---|
| CTACTTGGGA | GGCTGAGGCA | GGAGAATCGC | TTGAACCCAG | GAGGCGGAGG | TTGCGGTGAG | 1200 |
| CTGAGGTCAC | GCCATTGCAC | TCCAGCCTGG | GCAACAGAGC | GAGACTCCAT | CTCAAAAAAA | 1260 |

( 2 ) INFORMATION FOR SEQ ID NO:84:

( i ) SEQUENCE CHARACTERISTICS:
        ( A ) LENGTH: 1320 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:84:

| | | | | | |
|---|---|---|---|---|---|
| AGCTTTCTTT | TGCCATTAAC | AAGTAATAAC | AAGGATTGAG | TAGTAACAAG | AAATTCTTCC | 60 |
| TTCCACATAA | AGCAAACACC | TCATGGTCTT | GCTTTATCTC | CTTTCTTCTT | GATTCTCTAT | 120 |
| CATCTCAGAA | AATCAAACAT | GAATGTCATT | AAGCTCAATT | ATATAAATGA | TTCAAAATGT | 180 |
| GCAGAATCCA | CGGTTGATTA | TGGTGTTGGA | TATACTAAAG | CTGGATAATT | AAACAATTTA | 240 |
| TTTTGGCTCT | CATTCAAGCA | TTTGGCACTA | TAAAAGCATA | TTTGAACTTT | CTAGAAAAA | 300 |
| ATAAGTGCTT | CTTCAGCAAG | ACTTCGAAGA | TCTTTCGTTT | CATATATTGC | TGAGGACCTA | 360 |
| CTAAGTCCTT | CTAAGATCTT | TCTTTTCATA | CATCGTTGAG | GACCTATTAA | ATAACTGTGA | 420 |
| TAGAAACTGG | TATGAGAACA | AAAATGCCTA | GTGTCTACAT | TCACGAACAA | TATTTTGGAG | 480 |
| GCTTCTGGTG | ATGAATGCTT | GATTTAGAAG | GACTTGAAAG | GAATACAAGT | GATTGTCAAC | 540 |
| TCAGGAGGAA | TATTACATTT | TTTACACTCT | TGCTTTCTTT | CTTTCTTTCC | TCTTTCTTTC | 600 |
| TTTCTTTCTT | TCTTTCTTTC | TTTCTTTCCT | CTTTCTTCTC | TCTCTCTCTC | TCTCTCTCTC | 660 |
| TCTCTCTCTG | ACAGGGTCTT | GCTCTGTCAC | CCAGACTGAG | TGCAGTGGCA | CAAACACGGC | 720 |
| TCACTGTAGC | TTCAAATTCC | CAGGCTCAAG | CAATCCTCCC | ACCTCAGCCT | TCTGAGTAGC | 780 |
| TGGGACTGTA | GGCATGCACC | ACCATGCCTG | GCTAACTTTT | TAAATTTTTC | GTACAGATGG | 840 |
| GGGTCTCACT | ATGTTGCTCA | GGCTAGTCTC | AAACTCCTGG | ACTCAAGCAA | TACTCCCACC | 900 |
| TCCCAAAGTG | CTGGGATTAC | AGGCAGGAGC | CACTGCTCCT | AGCCCTATT | TTCTTGACCT | 960 |
| AGCTAAACCA | TTGAATTCCC | CCATCTCATT | AAATGCCTCT | TCAGCCTGCA | ATGCCAAAAC | 1020 |
| ATTCCTATAT | TTGCTAGGTC | TAACAACATA | TATAGAAGAT | GGGTCAAAAT | ACAATCCCAA | 1080 |
| AGTTTAATCA | CCCCTTACTA | TATTTCTGCA | CTCCCCTTCC | CTAGCACCTT | CTTCATGGCC | 1140 |
| TCTTTAACAT | CTTTGTTTCT | TAGTGTATAG | ATCAGGGGGT | TAACACTGGG | AGTGACAATT | 1200 |
| GTGTAGAAAA | GGGTAAGAAA | CTTGCCCTGG | TCCTGGGAAT | AAGTATTTGC | TGGCTGGAGG | 1260 |
| TACATGTATA | TGATTGTACC | ATAGAAGAGA | GAGACAACAA | TTAGATGCGA | GCTGCAAGTG | 1320 |

( 2 ) INFORMATION FOR SEQ ID NO:85:

( i ) SEQUENCE CHARACTERISTICS:
        ( A ) LENGTH: 751 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:85:

| | | | | | |
|---|---|---|---|---|---|
| AATTAAGTTA | AAGTTGAGGC | GGCTCAGTGT | GAGGAGAAAG | CCCATCATTC | AGAATACAGG | 60 |
| GACACCCCTG | CCCAGGTGCC | ATGACCTGAA | TGCACTANGG | GACAGGCACC | AAGGAAGGCT | 120 |
| CTGGCAGGGT | GCGACCCAGA | GGGGTTTTGG | GATCCACCAT | CATGGAGATG | CCCTTCCCTT | 180 |
| CATGTGAGGT | GGGGTTTCTG | CTCTCACTCT | GCCTTCAGAG | GTCCTACATG | AGAACTACTG | 240 |
| GGTGGCAGGG | GAATAAAGGA | GAATTAAGGA | GAAAGAGTT | TAACAATGCA | TGCCTATCTT | 300 |

|                |            |            |            |            |              |       |
|----------------|------------|------------|------------|------------|--------------|-------|
| AGAGGAGAGA     | GGCTATGAAG | GAGGCCTAGA | GTCTTGCGGC | CAGCTCCTGC | TTTCTTTAAA   | 360   |
| ACTTTCAGGA     | AGGGGAAGGG | ATAGATGTCA | CAACTTCTCG | GGATTGCTTT | TTTAGGGACA   | 420   |
| CAGGATAGTC     | TGATTCATCT | ACCCTAAAAT | ATGATTTTCC | TTTGGAATAG | ATATTTCAGG   | 480   |
| ATCAGAGAGT     | TGGAGAGATA | GGTGTTCTTT | TCCTTAATCT | TCAAACACAC | ACACACACAC   | 540   |
| ACACACACAC     | ACCATACATA | CACCTATGCA | TATACCAACA | AATACAATTC | TACATATCCA   | 600   |
| TACACACACA     | CACACACACA | CACACAGCTC | CACACACATG | CTAAGCAGGT | GCTTGGGTAG   | 660   |
| TACAGGATGG     | TTTGGTCATC | AGGAGGCTGG | GTAGGCACGA | GTGTGGAGCA | AAGAAGGAGG   | 720   |
| AAGATGGATG     | CTTTGTTAGA | CATTCCTGCA | G          |            |              | 751   |

( 2 ) INFORMATION FOR SEQ ID NO:86:

( i ) SEQUENCE CHARACTERISTICS:
        ( A ) LENGTH: 545 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:86:

|            |            |            |            |            |            |       |
|------------|------------|------------|------------|------------|------------|-------|
| TAATTTAGAT | TCTTTTTACT | CTCTTCTATT | CGCAAATATA | GCAAATTATG | AAAATAATTC | 60    |
| TGCACCTTGC | CTTTCTCCCT | TAGTTATAGC | TGGAAAAATA | AAAATTTAAA | AGCCTCTTTA | 120   |
| ATAGCAAAAG | GGGAGGGGAC | ACAAGGTGCC | GAGCTAGCAA | ACGACAGAGT | CTGTCAGGGA | 180   |
| GGTGGCTAGA | GAGGCCCGGA | AGTGGCTTCT | GTGCCCCGCC | CTGCGGGTGG | TTTGCTAGTT | 240   |
| TCAAGCACTT | TGTGAGTATG | GGGTGAATCG | GCGTCGGCCT | TCCACTGTGG | GGTTAAATCT | 300   |
| CATCCCGCGG | CTCTCCTCCT | GTCGGTCCTG | CAGTTCTTTT | GTCCCCGGGT | AGAGGTGCGT | 360   |
| TTGCAGGAGT | ATGTGTGTGT | GTGTGTGTGT | GTGTGTGTGT | GTGTGTTT   | GTGGAGAGAG | 420   |
| GCCCTTCCCT | CCCCAGTTCC | TGCAGCCTCG | GCTCCCAAGG | AGGGAGACCC | CTGCGAGAAG | 480   |
| CCGTGGGGGA | GGGAAGGGCG | CTCTGGGCGG | AATGAAGTGG | TCCTCGGCGT | TCCTGCGTAG | 540   |
| AGCCC      |            |            |            |            |            | 545   |

( 2 ) INFORMATION FOR SEQ ID NO:87:

( i ) SEQUENCE CHARACTERISTICS:
        ( A ) LENGTH: 296 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:87:

|            |            |            |            |            |            |       |
|------------|------------|------------|------------|------------|------------|-------|
| ACGTAAAGGT | ATTTAACTAA | AAGTGTCTTC | CTATAATTTC | TGTTAAAGTC | GNAACACATG | 60    |
| CCTATGTNGT | ATTTCTTTGA | CATATGCTGT | TATTTCTNCA | CTTTTTCCTG | TCATTTATAG | 120   |
| AGCCTTTCTA | TATATGTGAG | ATCAAGATTT | NACATTTGNG | TGTGTGTGTG | TGTGTGTGTG | 180   |
| TGTAAGGGGC | TGGGAAATAT | AGAGAATATT | GTGAGGTNNG | GGATTCTNCA | GAAAAATCAT | 240   |
| CTCTCACTGC | AACAGAGTAC | TATTGNNGAA | AGANTCCCAT | TCTACTGTTA | TCTAGA     | 296   |

( 2 ) INFORMATION FOR SEQ ID NO:88:

( i ) SEQUENCE CHARACTERISTICS:
        ( A ) LENGTH: 298 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:88:

|            |            |            |            |            |            |    |
|------------|------------|------------|------------|------------|------------|----|
| TTATACCAGA | ACTGCATCTA | TTACAGCATA | AACCAATTAT | ATCTTTGACC | AGAACCTATA | 60 |

| | | | | | |
|---|---|---|---|---|---|
| CTTTACTAAT | AGCGGTACTG | TCACCTATTT | CTGAGAGTGT | ATCAAGCTGG | AGCAGGAGCA | 120 |
| TGGAAAATAA | AACAGAGCTG | GAGCTTGAAT | TGACACTGAC | ATCATCCCTA | CCTTAGAAGA | 180 |
| CAAATATATG | TATGTGTNTA | CACACACACA | CACACACACA | CACACAGAGN | AGAGNCACAG | 240 |
| ATATAGTCAA | TCTGAATACT | TNGGTAAATT | TGTCCTGGAG | AGAAAACTTA | TCAGACAG | 298 |

( 2 ) INFORMATION FOR SEQ ID NO:89:

( i ) SEQUENCE CHARACTERISTICS:
        ( A ) LENGTH: 605 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:89:

| | | | | | |
|---|---|---|---|---|---|
| CTGTCATCTC | TGTCCTGAGG | CCCTGCCTCA | CCATTCCCTC | AAGGCCCAGA | CCATCATCAA | 60 |
| GGCCCTGGCC | ACCCAGCCAC | TGATGCATAT | GGCCTTTTCT | TTCTCTCATG | CAGCCTCTTC | 120 |
| TCCCTGGGGC | AGAGGTTGTG | GGGAGGGAGG | TGGTGTGTGT | GTGTGTGTGT | GTGTGTGTGT | 180 |
| GTGTGTGTGT | GGTTGCTGT | CCAGTTTTAA | AGGATTCCAA | GCCATGTGAA | ACTNCCTCAC | 240 |
| TAGATGTGAT | CTGGTTGCGG | CAAGTGCTTA | TTACNGAGTG | AGGCTGGGGA | ATGGGCTGGG | 300 |
| GGTATTAGCA | GTCCTTTTGC | AGTGTGTGTG | GTGGGGTCAC | ACCACTATGG | CTAAGCCTAA | 360 |
| GACACTCCCA | GAGAGAAGTA | CTGCAGAAGG | AACTGGTTTC | CGGACTGCAG | AGGGATCTGC | 420 |
| ATTTTGGNTT | TTGACCACCC | CCACCAAAAA | AATAGGTTAG | ATCTGAAGGG | CAAAGGGAAT | 480 |
| ACCCAAGCCT | CTGATGCCTA | TGAGAAGTCC | CTGGACTTCG | ACCCTTCTGA | TGTGTGATGT | 540 |
| TAGCCCCGNG | GGGAGCTGCT | CACCTGAGCA | CCTTTGGGGG | TGAGAAGGGA | GCAGGGAGGT | 600 |
| AGGGT | | | | | | 605 |

( 2 ) INFORMATION FOR SEQ ID NO:90:

( i ) SEQUENCE CHARACTERISTICS:
        ( A ) LENGTH: 2757 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:90:

| | | | | | |
|---|---|---|---|---|---|
| GATATCCACT | CTCTATACAC | TATGTATATT | TTTTGGTTTA | TTGCCTGCCT | CCCCAGCACA | 60 |
| CACACACACA | CACACACACA | TACACACACA | CACAAGATTA | TAAATTCCAT | GAAAGGAAGG | 120 |
| GCATTGTTTT | GCTCAAAATT | AGTTCCAGCT | TCCACAATAG | TGCCTGGCAT | AGTAGATAAA | 180 |
| TCAATATTTG | TGTAAGAAAG | GAGAAGAGGG | AGTAAAAAAC | TAAGAGCATT | TTTCACCCAT | 240 |
| CAATTTGGCA | AAGATCAAAA | TATTTATAA | CACTGTGTTG | ACAAGTATAG | GTAAATAAGA | 300 |
| ATACTGCTAG | TAGATCCTAT | GATTGGTGAT | TTGGCATTAA | CAAAAGTACA | AATTTCCCTA | 360 |
| TTCTATGCTG | TAGTAATTCC | CTTTCTAGAC | ATACAGACTA | TGGATATATC | CTTACACATG | 420 |
| AAAAATGATG | TGAGTTCACA | GTAAGTTATT | GCAGCAATGT | TTGAAAAAGA | AGAATTGGAA | 480 |
| ACAACCTCAT | GACCACCAAT | GGGGTACTTA | TTAACAAATT | ATAGAACATA | ATACACAGTT | 540 |
| GAATACCGTG | CAGTTGTTTA | AAAAAGAGCA | AGATCAAGGA | AACACTTATG | TACAGCCTTT | 600 |
| ACCAAGACCA | CCTGGTAAAA | AGAAAAATAA | GAAAGGTACA | GAAGTGCTAC | TATTTGTGCA | 660 |
| GAGGGGAAAA | AGCGCGGACA | ATCTATAACG | GTGTAATATA | TCTACGGAAG | GATATACAAG | 720 |
| TCACGAAAAA | TATTGTCAAA | CTAGACGCTG | GGGGACATTT | ACTCTTTTTA | ATAAATGTAT | 780 |
| GTGAATGCAT | TACTTATCCA | TATTACTCAA | TAATTAAACC | GAAAAACGTT | TTAAAGAAGT | 840 |

```
ACAAATAAGA CTTGCTCGCA GATCCCGCAA TCCCATCAAT ACGAGGCGTA AAAGCCGGGT      900
CCTCCACTGG CTAGGGCCGA GGAGGCAAGC ACTCAAGCTG CCACAGAGGC GAAGCTTCCT      960
AGAGCGGCCC GGAAGTGCCC GGCTGAAGCG GCCGGGCGCC GATTGGTGTC TTTGAGTCTA     1020
GTCTTTGTTC GGGGCTGTCC AAAGGACGCT AGCTGTTGCA CCTGTTCCTC CCTGCGCGTA     1080
AGGTGAGTGT CTCCGGCTC CCAGGTGGAG AAAAGGGGAC AAGACGCAGC TGTGGTCAGC     1140
AGCAACACCC TCCCCACACC TCCCTGTCGC GGGCAGAGTG TAACACTCCT GTCCCTCCCT     1200
CCGCCCCCCA ACAGATCTAC AGGAGAGGAT TTGGCCCAGC CTTCCGGGAG AGGATGGGTG     1260
GAAGGGGAC ACTGGTTGCG GTTCCTCTGC AGAGGCATCT GTCTGATCCC CTTCCAGGGT     1320
TGGCACACAT ATCCTATAAC CAGTGAATCC TGGGGCACA AGCTGGCCCG TGCATCTCAT     1380
GGTAACAGAA TGAAGAGCCT TTAACAAAG CCGTTAATAA TACTTGGCGT TTATTTAGTG     1440
CTTACTAGTG CCCGCTGCCA TGCCAGGGAC GTTGCATACG TTCTCATGTA ATCTGTATAT     1500
CAACCCTGTA ACACACATGA GAATTGTACC TGAGGATCTG TAGTTCTAGT CCAGATAAAT     1560
AACTTCCTCT AAGTTACACA ATAGAGCACA GATTCAAATC ATATCCCTGC GTCACTGTTT     1620
TTTGTTTTGT TTGTTTTGT TTGTTTCAG CTTCCTATAA GACTGTTTTC TCTGATTGAC     1680
TTCTGGTGGC TTGGCTTCAT TATGATGTGT TTATGTTCAC AGAAATTTTT GTAATTTCTC     1740
TATGGTAACA ACTTTTTATG CCTTAGGAGT GTCTCTGAGG CAGGATTCTA AGAGATTCTC     1800
TTTGACTCAA TCCCAGATAG AGGATAAATC TCCTGGCAAA GCCCAGAATG ACCACAGCCC     1860
TGGAACCTGA GGACCAAAAA GGACTTCTGA TAATTAAGGC AGAGGACCAT TACTGGGGAC     1920
AGGATTCCAG CTCACAAAAG TGCAGTCCTC ACAGGAGGGA ACTCTATAGA CAACACTTCA     1980
GGAAGCTCTG CTATCAGGAT GCACCTGGAC CCCGTGAAGC TCTTACCCAG CTGTGGGAGC     2040
TCTGCCGTCA GTGGCTGAGG CCAGAATGCC ACACCAAGGA GCAGATTTTA GACCTGCTGG     2100
TGCTAGAACA GTTCCTGAGC ATTCTTCCTA AAGACCTGCA AGCATGGGTG CGTGCACACC     2160
ATCCAGAGAC TGGAGAGGAG GCAGTGACGG TACTGGAGGA TCTGGAGAGA GAGCTTGATG     2220
AACCTGGAAA GCAGGTGTGA AGGGCAGTC ATCTGGCTGT GAGTGATCAG GGGATATGGA     2280
TGGAGCCAAA GCAAAAGGCA TATGAAAGAA CATCTGAAAA TATTTATCCT CTAAAGAACA     2340
AGGCATAGGA AGGGACCTGA CTACCTATGT CAAATAATTA AAGTGTGGCT GGGTAAAGAG     2400
AGGAGAGTCA CTAGACTGAT TCTATGCCTG TTTGGAAGGC TAGGATCAGT GGGAAGTTAC     2460
CAAAAGGCAA TCAGGTATCA GAGGAAAAGA AATAATTTTC TGCCATTCAT AGATACCCAT     2520
AAATAAAATA GGCTACCCCA TAAGAAACTC CCTTTCCATA TAGGTATTCA AGCGGAGATT     2580
CAAGTAGATG TCAAGGATAT TGCAGAATAG GACTGTCCAA CAGAAATATA ATGCAAGCTG     2640
TATATGTATT TAAATTTTCT AGTAGCCACA TTAAAAAAAA AGGTGAAATA TATATTTAT     2700
TTAGCCCACA ATATTTAATC ATGTAATCAA TATTTTTAAT GAGGTATTTT AGATATC       2757
```

( 2 ) INFORMATION FOR SEQ ID NO:91:

( i ) SEQUENCE CHARACTERISTICS:
       ( A ) LENGTH: 705 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:91:

```
ATGGTAAGTA TGTGGTTACA ATAACACCAA GGTTGTTTTC ACCTAATTGC AGGATTTATT       60
GTACCTCAAA GTAGAAATCT TAGAGGCATT CCCAGAACTG GGGTTAATCA GAAGTCAATA      120
```

-continued

| | | | | | |
|---|---|---|---|---|---|
| TGGTGGGTTA | CCATCCAAGA | TGGAGTGGCT | TTCAGCTGGG | CACAGTTGCA | GTTGGCCAAG | 180 |
| ATCATGCCAC | TGCACTCCAG | CCTGGGCAAT | AGAGCTACAG | TGTCTAAAAA | AAATCTATAT | 240 |
| CTATATCTAT | ATATATATAT | ACACACACAC | ACACACACAC | ATATGCACAC | ACACACATAT | 300 |
| ATACATATAT | AATATTCATG | CACACACATA | TTTTTGTACT | CTAGTTTGTT | GNCTTGAACA | 360 |
| TTATTTCCTT | CATATCTTTT | CACTAGGAGA | CAGCGGATTG | CCACACCGAA | GAGTGAGAGA | 420 |
| TCAATAAATG | TTTGTTGAAA | TTATATATAA | TTTCCTTTGA | TTATTGTACA | GCTTGGGAGC | 480 |
| CCATATTCAA | ACCTCTTTGA | TGATCATATG | GTCTAGGAAA | GAAAGTGCTT | TGTTCACCTT | 540 |
| ATAAGAGAAA | ATTAAGGGTA | TCGTCTTCAC | CACCCTCTTT | CCTACGATGA | AAAAGCCTGT | 600 |
| ACTTTGTACA | GTGGACAAGA | AGTATCTATA | TTCAATTCCT | GGCTAGTAGG | ATCAACTCAT | 660 |
| TTGAAAATAA | GCTGATTTNT | TTNNNNNTTC | AGATGGAGTC | TCGCT | | 705 |

( 2 ) INFORMATION FOR SEQ ID NO:92:

( i ) SEQUENCE CHARACTERISTICS:
        ( A ) LENGTH: 1045 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:92:

| | | | | | |
|---|---|---|---|---|---|
| TTTTCCAATG | AGTTGATCCT | ACTAGCCAGG | AATTGAATAT | AGATACTTCT | TGTCCACTGT | 60 |
| ACAAAGTACA | GGCTTTTTCA | TCGTAGGAAA | GAGGGTGGTG | AAGACGATAC | CCTTAATTTT | 120 |
| CTCTTATAAG | GTGAACAAAG | CACTTTCTTT | CCTAGACCAT | ATGATCATCA | AAGAGGTTTG | 180 |
| AATATGGGCT | CCCAAGCTGT | ACAATAATCA | AAGGAAATTA | TATATAATTT | CAACAAACAT | 240 |
| TTATTGATCT | CTCACTCTTC | GGTGTGGCAA | TCCGCTGTCT | CTAGTGAAAA | GATATGAAGG | 300 |
| AAATAATGTT | AAGTAACAAA | CTAGAGTACA | AAAATATGTG | TGTGCATGAA | TATTATATAT | 360 |
| GTATATATGT | GTGTGTGTGC | ATATGTGTGT | GTGTGTGTGT | GTGTATATAT | ATATATAGAT | 420 |
| ATAGATATAG | ATTTTTTTTA | GACACTGTAG | CTCTATTGCC | CAGGCTGGAG | TGCAGTGGCA | 480 |
| TGATCTTGGC | CAACTGCAAC | TGTGCCCAGC | TGAAAGCCAC | TCCATCTTGG | ATGGTAACCC | 540 |
| ACCATATTGA | CTTCTGATTA | ACCCCAGTTC | TGGGAATGCC | TCTAAGATTT | CTACTTTGAG | 600 |
| GTACAATAAA | TCCTGCAATT | AGGTGAAAAC | AACCTTGGTG | TTATTGTAAC | CACATACTTA | 660 |
| CCATACACAA | ATCCTGCCCT | TAGGCTAGGC | GCGGTATGTC | ATGCCTATAA | TCCCAACACT | 720 |
| TTGGGAGGCC | GAGGTGGGCA | GATTACTTGA | GGTCCAGAGT | TTGAGACCTG | CCTGGCCAAC | 780 |
| ATGGTGAAAT | GCCATCTCTA | CCAAAAACAC | AAAAATTAGT | TGGGCATGGT | GGGGCGTGCC | 840 |
| TATAGTCCCA | GCTACTCCAG | AGGCTGAGGA | AAGAGAATCG | CTTGACCTGG | GAGGCAGAGG | 900 |
| TTGCAGTGAG | CCAAGATCTG | GCCATTCCAG | CCTGGGCGAC | AGAAGGAGAC | CGTCTCAAAA | 960 |
| GAAAAGAAAA | AAAAAAATCC | TGCCCTTAGG | CAAATTCCCT | GTGGTTCATA | AGCCCTGGGT | 1020 |
| TTGGCTGGTG | ACAATGTGGG | GATCC | | | | 1045 |

( 2 ) INFORMATION FOR SEQ ID NO:93:

( i ) SEQUENCE CHARACTERISTICS:
        ( A ) LENGTH: 489 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:93:

| | | | | | |
|---|---|---|---|---|---|
| CTGCAGAAAG | ACTCCTGTTG | TCCACCTCGG | GAGCTGACAC | GATAAATGCG | GGTCAAATCT | 60 |

| | | | | | |
|---|---|---|---|---|---|
| CAATCCTTTA | ATATCTTTAT | GACTTCTTTC | TCTTTCTCTT | CAATTTCTAT | TTTCTCATGT | 120 |
| TCAAGCTCTG | ACATTCAAAA | CTAAACACCT | TTCTCTAACA | TGTTGCTTTA | ATTATTTAAG | 180 |
| CATTCTGCCT | GGGATTTTTT | CAATTACTCT | TGGGAGTTTT | CATAAAACTC | TACCAACATA | 240 |
| TCTCCAAGTG | GCCAGGCTTT | TCAATCACTG | CTTCCTCCG | TGTGTATTTC | ACACACACAC | 300 |
| ACACACACAC | ACACACACAG | CACTTAAATT | GAACAGGTTT | ATTCTTCAC | ACAGGAATTC | 360 |
| CTACGAACAG | CCCGGTTTTC | TCCACCATAT | GTCCACTCCT | TCTCTGCATA | GCTGAATCGN | 420 |
| GATTCTCACA | CTCTAATATT | TTACATATTC | TTACACTCTG | ATATGATCTT | GTCTCTTATT | 480 |
| CTTTATGGC | | | | | | 489 |

(2) INFORMATION FOR SEQ ID NO:94:

(i) SEQUENCE CHARACTERISTICS:
(A) LENGTH: 688 base pairs
(B) TYPE: nucleic acid
(C) STRANDEDNESS: single
(D) TOPOLOGY: linear (xi) SEQUENCE DESCRIPTION: SEQ ID NO:94:

| | | | | | |
|---|---|---|---|---|---|
| GATCACCTGA | GGTCAGGAGT | TCAAGACCAG | CCTGGCCAAC | ATGGTGAAAC | CCCATCTCTA | 60 |
| CTACAGATAG | AAAATTAGCC | AGGTGTAGTG | CCCAGCGCTG | TAATCCCAGC | TACTTGGGAG | 120 |
| GCCGAGGCAG | GAGAATTGNT | TGANCTCGGG | AGGTGGAGGT | TGCAATGAGC | TGAGACACGC | 180 |
| CACTGCACTC | CAGNCTGGGN | GACAAGAGCA | AAATTCCTTC | TCAAAAAAAA | AAAAAANNTG | 240 |
| CAANCCTAGA | CTCTTATAGC | TTGCAGACGA | GAACGATGAA | ATCTCAGATG | ATTGAGCATC | 300 |
| TCACAGAAAC | AAAGGCAATA | AAACTCATAT | TTACCCTACT | CATCTAAATT | TATGTTCAAA | 360 |
| GCTTTTATTT | CACTACTAGG | GCTGTAATGT | GNCCTGGAAC | ACATGGCATG | TATGTGTGTG | 420 |
| CATATGTGTG | TGTGTTGACC | AAAGAGGTTG | GAGGAATTTT | TTGATACAAG | GNCAAGCACT | 480 |
| CTCNCAGAAT | TGGATTCCTA | NCTNATGCTG | TAGTTATGGG | TCTTCTGCCA | ACCAAATTCA | 540 |
| AGACTATCAT | TTCTCCTTAG | GAAAACCTGC | CTGGTGGTAC | ATGCCTTTGT | TAACATCAAA | 600 |
| TTCGTTAAAA | TTAAAATTAC | ACACACACAC | ACACACACAC | ACACACACAC | ACACTCGCAT | 660 |
| CCCTCCTGAA | TTAAACATTT | TTCTGCAG | | | | 688 |

(2) INFORMATION FOR SEQ ID NO:95:

(i) SEQUENCE CHARACTERISTICS:
(A) LENGTH: 1166 base pairs
(B) TYPE: nucleic acid
(C) STRANDEDNESS: single
(D) TOPOLOGY: linear (xi) SEQUENCE DESCRIPTION: SEQ ID NO:95:

| | | | | | |
|---|---|---|---|---|---|
| TGCCAGCAGA | CTCTTCTAGC | TGGCGAAGGC | AAGGAAACAG | ATTCTCCTCT | AGAGCTTACA | 60 |
| GAAGGAAGAT | AGCCCTGCTG | ACTCACTCTA | GCACCCCTGA | CATCCAGAGC | TGTGAGATAA | 120 |
| TAAATTTGTG | TTGTTTTAAG | CTATTAAGTT | TGTGGTAATT | TTTCACAGCA | GTAATAGGAA | 180 |
| ACTAATGCAT | GCCCTTTCCC | AGTCAGTCAC | ACTCCGACCA | CACAATTTCC | AGTCAACTAT | 240 |
| AGGCCCTTTC | CATCATGATG | GTTTGCCTT | TTCTGGAATT | TAATCTAAAT | GGATTAAATT | 300 |
| ATATGCTATG | TACTCTAGTT | CCTGGTTTTT | GCTCAGAACA | TTTTGAGAT | TCATTCATGT | 360 |
| TGTTGCACAT | ATCAGTAATT | TATTCCATTT | ATTAGCACTT | TATTGGTAAA | ATGTATTCTA | 420 |
| TTTGTACAGA | CATGCCACAA | TTTGTTTTTC | CATTCATGTG | TGGGTGAACA | TTTTTATTAT | 480 |
| TTCACATTC | TAGCTATTAT | AAATAGGGCT | GCTGTGCAAA | TTTGTGTAAC | AAGTCTTTGT | 540 |

| | | | | | | |
|---|---|---|---|---|---|---|
| GTAGACATAT | ATAAGCCAGA | GTTCTTCAGA | AACAGAAAAC | CAATAGTGTG | TGTGTGTGTG | 600 |
| TGTGTGTGTG | TGTGCGTGTG | TGTGTGTAGA | CAGTGATTTT | AAGGAATGGA | CTTACATGAT | 660 |
| TGTAGAGTCT | GGCCAGTTCA | GATTCTGCAC | GGTATGCCAG | CAGGCTGGAA | ACCCAGGAAA | 720 |
| AAGTTAATGT | GGCAGCTAAA | ACTCAAAGGC | TGTCTGCTGC | CCAAAAGTCC | CTCTTCCTAG | 780 |
| GGAGAGAAGT | TAGTCTTTTT | TCTCTTAAGT | ATTTTCAAC | TGATAGGAAG | CAATCTGCTT | 840 |
| TACTCAAAGT | GTACTGAATT | AAATGTTAAT | CTCATCCAGA | AGTACCTTCA | CATCAACGTC | 900 |
| TAAACTAGTG | TTCGATCAAA | TATCTGAATA | CTATGAGCTA | GCCATGTTGA | CACGAAAAAT | 960 |
| TAACCATTGN | ATATGTTTTC | ACTTCTTTTC | CAGGAAATAC | CTAGGAATGG | AATTGCTGGT | 1020 |
| CATTTAGTAA | GTGGGTGTTT | AACTTTATAA | GAAGCTACCA | GTGTTTTCCA | AAGTGGTGGT | 1080 |
| TCANTTTACA | TTCCAAAAAG | CATTATATGA | GAGTTCCAGT | TGNACAACCT | CCTCAGCATT | 1140 |
| TGNTATTGTC | AGACTTAATG | TTTATG | | | | 1166 |

( 2 ) INFORMATION FOR SEQ ID NO:96:

( i ) SEQUENCE CHARACTERISTICS:
        ( A ) LENGTH: 1000 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:96:

| | | | | | | |
|---|---|---|---|---|---|---|
| AATCTACCAT | AGTTTCAGTT | TCATTGTATT | TTCTTATATA | TTTATATTGT | GTACTGATGT | 60 |
| GTGCATGGAT | TAGTAATGAG | TACTCTATTA | TTTTAATGT | CATAATTATT | CATTATTTAT | 120 |
| TTATTATTTA | TTAAAAATAA | TATTTAATAT | TAAATATTAT | TTATTACTTA | TATTATTTAT | 180 |
| TATTATAATA | ATTTATAATA | TGTCACATTA | TAAAATATTA | TTTAATTAAA | ATTTAATGTC | 240 |
| ACTCTATTAT | TTTAATATCA | TAAAATACAT | GAAATACAT | TTTCTGTAG | AATCACGTTT | 300 |
| TCCTCCTACT | GTGAATAAAG | ACATAACTCA | CTAAGGGGAA | GAATCTTGGC | CCNAAGTGTG | 360 |
| TGATAAATCA | NANAANANAT | AAAAGTGTNC | NNAAACAAAC | AGTAAAGGTG | AAAGGAGGCA | 420 |
| CAAATTTAAT | AAAGTTACTC | CATAAATCAT | AATTGACATT | AAATGTTGGA | ATGTAGGAAC | 480 |
| TGATTTATTA | ACCATATAAA | TTTAAAACAC | ACATGTTATC | TTTTGACAAA | TTGTTTACCT | 540 |
| ATTTTAGTTT | TCAAAGTGGG | CAAAATTAAC | ACCTCAAAAC | ATATAAGTGT | TTTCAGAGAA | 600 |
| GGATCACAGA | GTGTGTGTGT | GTGTGTGTGT | GTGTGTGTGT | GTGTGTATAA | TGGTAATNTG | 660 |
| TAGACTTAAC | AGCACCTTTT | GCCTAAATGA | CAAAATGGCC | TAGACCCAAT | CTGGCAGAGT | 720 |
| CCTTTTTCCA | GAAGAACTGG | GAAAACTTTT | CATATTTAAG | TTTGGAACAA | CAGAGAGAAC | 780 |
| GGGAAGACTT | TGGCATTTAG | AGAATGTGAA | TATTTGTATT | TCTCGATAAA | GTGAGAAATC | 840 |
| TTTGTGGAAA | AGCTATGGCT | TTANTCAGTT | TCAAATCTGA | GACCCCTTTC | TTGTAGGCAG | 900 |
| ATGTGCTAAC | CANTTNACCC | CAAAAAACTT | TCTCTTCTGT | GCAGCAATCC | ATAGCAGAAT | 960 |
| GAAAGGAGGA | TTCTTTGGAT | ATACTCAAAC | CTAATAACTT | | | 1000 |

( 2 ) INFORMATION FOR SEQ ID NO:97:

( i ) SEQUENCE CHARACTERISTICS:
        ( A ) LENGTH: 1470 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:97:

| | | | | | | |
|---|---|---|---|---|---|---|
| CTGCTGAGCA | TTGTGTCCCT | GTGAGCCCCT | CTACGTTATT | TTACCTCTGA | CTGGAACACA | 60 |

```
CCTCCATCAT TTTTCCCTCA CTTCCTGCAA GTTGCTGTCT AAAGGTGACT GTTCCACATT    120
TTTGTTATGA TAGAGGGTCC TTATTGGTAC CATGTGAGAA ATTACCTTGA TGCCCTGGTA    180
GGCTCCAAGT ATAGTCCCAT GCAAGCTCTC CCAGAGGACA CAGCACAAAT AGGTTTGCAG    240
ACTATGCAGT GAAATGCTCA AATCACAGCT TCATTAAAAA ACATAGCAAG CAGCAAGGGG    300
AAAAGAAGA GCAAGTTAAT GGTTAGTCC CTAAGTGATT TGCCAGAACC ACACTATCTG      360
ACTCAAGTGT GAGCAGTTTC CGTATATCTG ATCTCTTTTA CATCGCTCAA TCAGCCTGTA    420
GGATAGACAC AGAGATATAT ATGCCTGGAC CCAACCAATT AGTTGGTTGA ATAGCCATGG    480
ATTTTATTTT TGTTCCTAAA GTAGAGAACT TATGGTGTCT CCAATTTGTG GCTGACTCAA    540
GGCCTCATGA ATAATGAGTC AGTGCTTCGA TGTCTCATAT ATCTGTGAAT TCTGAATGTG    600
TGGCTCCTTT TGTATATTGG GTGCATCAGG AACATTAGGT ATCTTTTGAC CCTTCCATCC    660
CTTATATCTA TATTTAACAA CATATGCTCT TTTTACTAAC TACTTATGTC TACTTAAAAC    720
ATCTTAAGCA TTTTTGCCTA CATTTTACTA ACTAAAAGCA TATTTATCTT TTATAATAGA    780
ATTGCTCATT TACAAAAGTA AATATGTGTT ACAATCCATA TCATTTATTG GTGTATCCCT    840
GACATATAGT AGGCACTCAA TACATATATG GAATGAGAGA ATTGTGCTTT CTCTCTCCCT    900
TTTCGCCTTC CCCTCCTCCT GCTTTTTCTC CTACTCTCAC ACTGTCTCTC TCTCTCAAAC    960
ACACACACAC ACACACACAC ACACACACAC ACACACACAT GGACAGGAA TCCCAGAGAT    1020
CTGGGTTCTG GCGTGACAGC ATGTTTTTCA CAAATACTTC TTGGTTTCCA TTCCTTCAAA   1080
TGTAAATAAA GGTAGGGTTT AGTAAGATGA TCTTTGAGTT TCCTTCCAGG ATTCAGAGTT   1140
TCATCAATAA TTTCTTTATT CCTTTGCTCT ACAAGGTTTC TTTGTGCTGT GGCTTTAATG   1200
TAGCCTATCA AACACATTTC AACAAAATCA AAAGCCTTTT GTTTGCCCA TCACCATTTC    1260
TAGGAGGATC ACTGCCAAGA TCCCAAAGTA GAGGAAATTT TTCCTATAGA ACATAATTGA   1320
ATTTTGTATT AAGCAAGCTA AAACCAGAGA AAGATTAGAT TTTAAAACCT TTAAAAGTGA   1380
AGCTAGGAGA GGTGCCTCAT GTCTATAGTC CCAGCTACTT GGGAGGCTGG AGTAGGAAGA   1440
TAGCTTGAGC CCAGAAGTTC AAGGCTGCAG                                    1470
```

( 2 ) INFORMATION FOR SEQ ID NO:98:

( i ) SEQUENCE CHARACTERISTICS:
        ( A ) LENGTH: 724 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:98:

```
CTGCAGAAAG ACTTCTGCTG TCCACCTCAG GTGCTGACAT GATAAATGTG GGTAAACCTC     60
AATCCTTTAA TATCTTTATG ACTTCTTTCC CTTTCTCCCC AGTTCCTGTT TTCTCATGTT    120
CAAGCTCTGA CATTCAAAAC TAAACACCTT TCTCTAACAT GTTGCTTTAA TTATTTAAGC    180
ATTCTGCCTG GGATATTTTC AGTTAGTCAT GGGATTTTTC ATAAAACTCT CCCAATATAT    240
CTCCAAGTGG CCAGGCTTTT CAATCACTGC TTCCCTCCAT GTGTTTCAC ACACACAC      300
ACACACACAC ACACACTCTC CACTTAAATT GAACAGGTTT ATTTCTTTAC ACAAGAATTC    360
TTACAAACAG CCCGGTTTTC TCCACCATAT GTCCACTCCT TCTCTGCATA GCTCAATTTT    420
GATTCTTACA CTATATTTTA CATATTCTTA CACTCTGATA CGATCTTGTC TCTTATTCTT    480
TATGGCTCTG CTCTGTAATT TTGTTGTTGT TGTTCTGAAA TATAGTTGGA CATGTAACTT    540
GTACATGACA CACCTTAGCA AGGAGGCAAC TCATATCTCA GATGTAAGTG AAAGAAGCAC    600
TCTCCAGGGG TTTCCTATGG GAGTGGTCAG CACGCTGGCC TCATTGGTGG AATGGCCTAG    660
```

TTACGAAAAC AGCAGGAGCT TTTTGCCTTC CAGAAATCTG GACCATCTCA CAACCCCAG        720

ACAG        724

( 2 ) INFORMATION FOR SEQ ID NO:99:

( i ) SEQUENCE CHARACTERISTICS:
        ( A ) LENGTH: 236 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:99:

CTGCAGATAT GGGCTTCATT AATTACATTG TTTTCAAGT CTCTCTTTCT ATATATATGT        60

GTGTGTGTGT GTGTGTGTGT GTGTGTGTGT GTGTGTGTTG TTTTGTTTT TGTTTTGAG        120

ACAGAACCTC ACTCTGTCTC CCAGGCTGGA GTGCAGAGGT GTGATCTTGG TTCACTGAAA        180

CCTCTACCTC CCAGACTCAA GTCCAGCCTC CCAAGTAGCT GGGACTACAG CTGCAG        236

( 2 ) INFORMATION FOR SEQ ID NO:100:

( i ) SEQUENCE CHARACTERISTICS:
        ( A ) LENGTH: 363 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:100:

TCGACTCTAG AGGATCCCCC NAGGGGAAGA CCAAGTCTGG GACTTCAGCG CCAGCCTCGC        60

CACCCTGCTT CCCACAACCA GATGTCTCCT GCGAAGTAGC CCCCTCTAAT GCCAAACCAA        120

AAGCAGAGGT CATAAGGACT ATATCCCTTA CACACACACA CACACACACA CACACACCCT        180

AACGGCTAAC TTCTCTGGAA GGTGCCTCAT CCAAGCAAAG CAGAACTGAA GATACTTTTA        240

CATGCCTTTT TCCGTTATTT TTTATCCAAT CAGACTTTTT CAGACTTCCT TTGAATACAA        300

GTATCTGCAG GATTTTNCCT TGTNCACCTG TAGACACTTT TTCTCTTTTN CAAGGAAGGG        360

TAC        363

( 2 ) INFORMATION FOR SEQ ID NO:101:

( i ) SEQUENCE CHARACTERISTICS:
        ( A ) LENGTH: 534 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:101:

TCCCTAATGG AATATTATGC AGCTGTTAAA AAGAATGCTT TAAAAAAAAC GACATAAAAT        60

ATGCTCATGG CATTGTATGG GGTAAATCCA AGTTGCCAAG TAGTGTATTC TTATTTACAT        120

GATGTCACAC ACACACACAC ACACACACAC ACACACACAC ACATATAGTT TTAGGAAAAA        180

AGAGTGACTA TAAGGGTCAA TGCCAAGATG TTAACAGTGC TGTTACATTT TTTTTTTTGG        240

TGCAACAGAC AGCTCCTCTA AAGATAACTT TCTCTATTTG TCTCTATCCC AAACTATCAA        300

TGGTGTGGTT AAGAAATAGG AAACTCGGCC GGGCGCGGTG GCTCACGCCT GTAATCCCAG        360

CACTTTGGGA GNCCGAGGCG GCGGATCAC GAGGTCAGGA GATCGAGACC ATCCTGGCTA        420

ACACGGTGAA ACCCCGTCTC TACTAAAAAT ACAAAAAATT AGCCGGGCGT TGTAGCGGGC        480

GCCTGTAGTC CCAGCTACTC GGGAGGCTGA GGCAGGAGAA TGGCGTGAAC CCGG        534

( 2 ) INFORMATION FOR SEQ ID NO:102:

( i ) SEQUENCE CHARACTERISTICS:
  ( A ) LENGTH: 672 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:102:

| | | | | | | |
|---|---|---|---|---|---|---|
| GTCTCGCTAT | GTTGCTCAGG | CTTATCTTGA | AACTCTTGGC | CTCAAGCAAT | CCTCCTGCCT | 60 |
| CAATTCCCAA | AGTACTGGGT | TACAGATGTG | AGCCACCATG | CCCAGCCAAA | ACCATAAAGA | 120 |
| TTTTTATTAT | GACTTGCAAG | GAGCAAAGAC | TATGTGTTTC | AGTCAGCTAT | TGCTCCATTA | 180 |
| AAACACACAC | ACACACACAC | ACACACACAC | ACACACACAC | AAATGCTTAA | AACATACAA | 240 |
| TAAGCATCTG | TGTGTGTCAG | TTGAAGGTCA | ATAGCTCTAG | GCCAAATTAT | ATGAATGGCT | 300 |
| GTACCTTAAG | ATGTAAGTAC | ACTTCAGCTT | ACCTGCTTTG | CGCTTCACAG | TAGGAACTCT | 360 |
| AGTTAGTTCA | AAGCATGTTC | TTTCTGGGGC | CAAGGGTGAA | AAGACAGCAG | CTACCCAAGG | 420 |
| GAAAATTTTT | CTCATGAAGA | TGGCAGAGGT | GCATATGGAC | ACCCAACTAT | GCAGGCATAT | 480 |
| TCAAAGGCCC | TAATTGACTC | ATGCCTGCTA | ACTGCACATT | GACCAAAGTC | ATTGTCATGC | 540 |
| CCAAGGCCAA | AGTCAAAGTG | ATATGGAAAT | ATACCACATG | TCTTTGGGAG | GAATTGCAGA | 600 |
| GTTGTTAGGC | AAAGGGCTTA | GATATGGAAA | GAAATGAAGA | ATTACCAAA | ACTTACAAAT | 660 |
| TAACCTATAT | CT | | | | | 672 |

( 2 ) INFORMATION FOR SEQ ID NO:103:

( i ) SEQUENCE CHARACTERISTICS:
  ( A ) LENGTH: 2040 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:103:

| | | | | | | |
|---|---|---|---|---|---|---|
| GACGGTATCG | ATAAGCTTGA | TATCGAATTC | TCTGCTGGGA | CAGAAAGTAT | ATAGTGCTCA | 60 |
| TCAGTCTTCC | AGAAGACTTG | CATTCATTTG | ACAAATATTG | ATTAAGTGCT | GATTATTTAC | 120 |
| CATGCACCTA | TTTTAAGTAC | TGGGGATACA | GCAGTGAATA | AACAGACAA | AAGGCCCTGC | 180 |
| CTTTATGGAG | TTGACTTTGT | AGTGGACAAA | AAGAAAAAA | ATTATTTTAT | TCAATCAACT | 240 |
| TCCCAAAAAT | TCATATAATA | CTGTTTATTA | TCTCTTTTTC | AAAATGAGCA | AACTGAGACT | 300 |
| CAGAAAGATC | AAATTATTTG | TGGACACAA | ATGTTAGTGA | GTGGTAGTTT | ACCCATAAGC | 360 |
| ATGAATTATA | TTGTCCAGGG | AGAAACTACA | CCCCTAGATG | GCGAGGCTGG | GGTGCTGGAA | 420 |
| ATAAAAATAC | TATAATAGAA | ATAAGAATG | CCTTTGATGC | ATCAGTAGAC | TAGACATGAC | 480 |
| CAAGAAAAAT | CAGTGAGCTT | GATAAAATGG | CTATAGAAAT | TTCTAAAACT | GAATTGCCAA | 540 |
| GACAGAAAAA | AGAACTAAAA | AGACAGAATG | GGCTGGGCAT | GGTGGCTCAC | GCCTGTAATC | 600 |
| CCAGCACTTT | GGAAGGCCGA | GGCGGGCGGA | TCACGTGAGG | TCAGGAGTTC | ATGACCAGCC | 660 |
| TGGTCAACAT | GGTGAAGCCC | CGTCTCTTCT | AAAAATACAA | AAAATTAGC | CGGGCGTAGC | 720 |
| TATGTGCCCC | TGTAATCCCA | GCTACTCAGG | GGGTTGCGGC | AGGAGAATCG | CTTAAATCCA | 780 |
| GGAGGCTGAG | GTTGCAGTGA | GCTGAGATAC | TGCCATTGCA | CTCCAGGCTG | GCCGACAAAA | 840 |
| GCAAGACTCT | GTCACACAAA | CACACACACA | CACACACACA | CACACACACA | CACACACACA | 900 |
| AAGAATGAAA | TATCTAAGAA | CTGTAGGACA | ATTATAAAAG | CTGTAATATA | CATGTAATAA | 960 |
| AAAAAATCAC | AAGGTGTGAT | ATACATGTAA | AGAAACATAC | TGGAAGGAAG | AAAGAAAGAA | 1020 |
| ATAGAGAAAG | AGAGAAAGAG | AAAAAAAGA | AAAAGAGAA | AGAAAGGAAG | AAAGAAAAAG | 1080 |

-continued

| | | | | | |
|---|---|---|---|---|---|
| CAAGGAAGGG | AGGGAGGTAG | CAAGGGAGGG | AGGAATGAAG | GGAGGGAGGG | AGGGGAAAGA | 1140
| AAAAAATTAG | AAAAAATATT | TAAAGCAATA | ATTACTGAGA | ATTTCTTAAA | ATTAATAATA | 1200
| AACCTCAAAC | CACAGATATA | GGAAGCCCAG | AGAATGCCAA | GAATAAATAA | AAAAAAAGT | 1260
| TACAACCTGA | CATGTTGTAA | CCAAATGACC | CCAGTTTTTT | AAGAAACGG | GAATGAAGTA | 1320
| CTATTTTTTG | TTTTCTGAGA | CGAATTACTA | TTTTTAAAG | CTTTCTCTTC | TTTTCCCCTT | 1380
| TCCCCTTTTC | CTCTTGCTCC | TCATTTCCAA | CTTAGCCCTT | CAGAAATGCA | AATACAACGT | 1440
| TTCACCTCCT | CCCCTCACCA | GACATTCGCT | ATAGGAAAAA | TTCTCCTAAC | TACGTGCTTC | 1500
| AAGACACAGC | TCTCCTCCAG | AGCTGACAGT | CAATTGCAG | ACCAAATTGC | CAGGGAACTT | 1560
| TCATCTCTAG | GGCGTGGCCT | CGGAACTTCC | CACTCTCCAG | GAGTGGTCTT | GGAACTTTCT | 1620
| TCCACCTGGA | GAGCATATTG | AAAACATGCC | CTTTTGGTC | ACTTTTCAA | TCTACTTCTG | 1680
| TCCATGTAAG | TGCTACCTCC | CACTGTNCAG | TAGATAACTN | CCCGGTANCA | AGGGGACCCC | 1740
| TNCCCTTGCT | CATTTCCTCC | CCTACCANAT | GNAAATGCTT | ACNTTTTTT | TTTTTTTTG | 1800
| CCACTTCAGC | TCCAAAGGTG | AAACGGCACA | GTTAAAAGCA | AGAAATTTTG | TGTCCCTTCC | 1860
| CCAAGCTAGC | TTTGGAATAA | ATCCACTTTT | CTTGTACCAG | ACCCCACTCT | TGTTAATTGG | 1920
| ACTCTACATG | TGGTAAGCAA | CTAACTTGAT | TTTCGGTTAC | AATATAATAT | TCAACTTCAG | 1980
| TAAATCAAAG | ACAATTTTGA | AAGAAGCCAA | AGGGAAAAAA | ATGACCTGAA | GAGTCCTGTT | 2040

( 2 ) INFORMATION FOR SEQ ID NO:104:

( i ) SEQUENCE CHARACTERISTICS:
( A ) LENGTH: 600 base pairs
( B ) TYPE: nucleic acid
( C ) STRANDEDNESS: single
( D ) TOPOLOGY: linear ( x i ) SEQUENCE DESCRIPTION: SEQ ID NO:104:

| | | | | | |
|---|---|---|---|---|---|
| CATCTGTTAC | TCTCTGTATC | CATCCTGAGT | AATGTTCTTT | TCAGCTCAGT | CACAATCATT | 60
| TTTTGATAGC | CTATCCTATA | AGCTTAACTT | ATAGTGTTAA | TCAGTATTAA | TACATCTTAG | 120
| TGGGAAAGAA | GGAAAAAATA | AACGATCACA | CACACACACA | CACACACACA | CACACACATA | 180
| CATTACGTA | ACAGAGCAAG | TGTGAAAATA | CCTAAAGGCT | TTATAGCTCC | TTTTGTCAAT | 240
| GGATACATGA | CAGCATTTTT | GGCATTCTTT | GCTACTCTTA | TTCTATGCTC | CATTTGTCTT | 300
| CAGTCAGCAC | CTCAGCTGCC | CTTATGTTTT | ACTTGGTAAG | GCAAATTCCT | AAATGAGCCT | 360
| GGTAATTAGT | CATCCAGCTT | ATAGGAAGGT | ACTATAGTTT | TCATTAACT | TTTTCACTGG | 420
| GCTTGAGAGT | AGTAAGGACT | CCCAGAGAAT | TCCTTGTGTT | CCAAAAGTAC | TTCTCCTTGA | 480
| CATCTTGGTA | TAGGATTAAT | AACTGTTTAC | CTTTGATAAT | CAGGAAGAAT | GACTCCAGCT | 540
| AGTACAGTTA | CGTGATGCCT | ATACATTCCT | TTTTTTCTGG | GAAAAATGTA | ATGTGAAATT | 600

( 2 ) INFORMATION FOR SEQ ID NO:105:

( i ) SEQUENCE CHARACTERISTICS:
( A ) LENGTH: 340 base pairs
( B ) TYPE: nucleic acid
( C ) STRANDEDNESS: single
( D ) TOPOLOGY: linear ( x i ) SEQUENCE DESCRIPTION: SEQ ID NO:105:

| | | | | | |
|---|---|---|---|---|---|
| GACTCTAGAG | GATCCCCACT | TGCTTTTTAA | AATTTTATAG | CGTGTTAGAC | ATTAATGTCA | 60
| TTGTTTCATG | TAATGCTACT | ATTTACTCAT | ATTTGGACCT | TCCCAGCTCA | TTAGTCTTTC | 120
| TTGTAGCTCA | GACTACATTT | TTTGGATAAT | TTTTCTTTGT | CCTAAAGTAT | ATCCTTTAGT | 180

```
GTTTGGGGTG TGTGTGTGTG TGTGTGTGTG TGTGTGTGTG TGTAGTCTAG TAACAGTAAA      240

TGATCTCAGT TTTTGCAGTG ATGAAAATGC TTTCATCTTC ATTTGTAAAA ACTAGGTCCA      300

TTGGGTATAT AATTCTAGAT TGATATGTTA TGTGGGTACC                            340
```

( 2 ) INFORMATION FOR SEQ ID NO:106:

( i ) SEQUENCE CHARACTERISTICS:
        ( A ) LENGTH: 429 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:106:

```
CCTGCAGGTC GACTCTAGAG GATCCCCACT TACTATTGCT TTTATATTAA CCTCTGTTCA       60

TTCCATTTCA GGCATATTCG TTTGTTCGTG TGTGTGTGTG TGTGTGTGTG TGTGTGTGTG      120

TGTTTTCATC AGCATTTACT CTAAATCTTT CTACTAATAG TAATAAACTC TAAACACATT      180

GTATGTATGC AACAGAATGA ATTTTAGCT ACTTGGTTT CTGAATTACT GAGGTTAGCA       240

TGGGCTATTT GGCACTTTTA TTTGGCAGCC AACTTATGGG TTAATATCCC TAGTGTAGGT      300

ATAGTGGTGA AGTTAAAATT GTTAGCTAAA TTGAGGTTTG AGAATAATTT ATTATCCTTG      360

AGATTTNCTG TTGACTATTG CCAGAAAGAG TCCANAAGTT TAGTGTGGGT ACCGAGCTCG      420

AATTNCATC                                                              429
```

( 2 ) INFORMATION FOR SEQ ID NO:107:

( i ) SEQUENCE CHARACTERISTICS:
        ( A ) LENGTH: 380 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:107:

```
AAGCTTGCAT GCCTGCAGGT CGACTCTAGA GGATCCCCTT AGAGGCTTTG AATGCTTTAT       60

TCTGATTCTG ATTCACATTT GACTCCAAGG GGAAAACACT CAGTTTGTGT CTGGGCAGTC      120

CACACATAGC AGCCAATACA TATTTAAAAT ACACACACAC ACACACACAC ACACACTCTC      180

TCTCTCTGTC TCTCTCTCTT CCCTAATACT TCTGATGACA TATAATAAGA TTGATCAAAT      240

TAGACATATT TAATATCAAT GATGTATAAC ATTTATAAAA CCTGTGCTTG TGATATTTTT      300

TTGTTAAAAT GTTTNCTTAC AGCAAGGAGA AAAAAGTTT AGATTGATGC CTGACTTTGC       360

TACATCCTGT AACAGGGTAC                                                  380
```

( 2 ) INFORMATION FOR SEQ ID NO:108:

( i ) SEQUENCE CHARACTERISTICS:
        ( A ) LENGTH: 487 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:108:

```
GACTCTAGCA GGATCCCCAT ATGAATTTAA TACATGATAT AAAATACCGC CTANTCATCT       60

TTTATATTAT GTGGTTTGCC TTNAACTAA CGTTNGGNAG TTTGNCCCTG TAAATTGAGG       120

TCACTAACCC CGTNTATGTT TTGGAAATCC TTTATCCCAA CTTATTGCTC TTTCTATAAC      180

TCTCTTTACA TATATTCTGT CTTAAACCAC TTTTGGACCT ATCTAGTCTG TGTCCTTTCC      240

TAGATGGCTT TTGTGTTTCC TCCTCACTTA GCAATGACAC CCTCCCATCA CCATTCCAC       300

ACACACACAC ACACACACAC ACACACACAC ACACACACAC AAATGAGGTA TATAAAGGGT      360
```

| | | | | | |
|---|---|---|---|---|---|
| CTCCTAAAAT | GTCATCTGAT | ATTTGTTATT | TCATATTCTC | AGATTTTTAA | TCCATTTAGG | 420 |
| TAGGTCTATT | TTAGATAGCC | TTGTCTGAAA | CAGAGTACCG | AGCTCGAATT | NCATCGATGA | 480 |
| TATCAGA | | | | | | 487 |

( 2 ) INFORMATION FOR SEQ ID NO:109:

( i ) SEQUENCE CHARACTERISTICS:
        ( A ) LENGTH: 385 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:109:

| | | | | | |
|---|---|---|---|---|---|
| GGTACCCCTA | TTCCAGGGCT | AGGGTGGGAG | GATTGTTTGA | TCCCTGGAGG | TCAAGGCTGC | 60 |
| AGTGAGCCAT | GATCACAGCA | ATGCGCTCCA | GCTCTGGGCA | ACAGAGCGAG | ACCCTGTCTC | 120 |
| AAAAAAAACA | AAAATGCCTA | TACAATAAAT | CTATAAAAAG | TGGGTTTTGT | GTGTCTATAC | 180 |
| ACACACACAC | ACACACACAC | ACACACACAC | ACACCTGCAT | AGACACTCAG | GTGTTCTGGA | 240 |
| AAGACACAGG | AATCTGAAGC | CAAAATACTT | GTGATTTTTT | TTCAGGGGGA | TCCTCTAGAG | 300 |
| TCGACCTNCA | GGCATTCCAA | CCTTCAACNT | GCTCCGAGTT | GCTATAGTGT | CACCTAAATC | 360 |
| GTATGTGTAT | GATACATAAG | NNATG | | | | 385 |

( 2 ) INFORMATION FOR SEQ ID NO:110:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:110:

| | | |
|---|---|---|
| CACCAAGTAC | ACCAGCTC | 18 |

( 2 ) INFORMATION FOR SEQ ID NO:111:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:111:

| | | |
|---|---|---|
| ACTCACACGC | AAAAAGCC | 18 |

( 2 ) INFORMATION FOR SEQ ID NO:112:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(1, "")
        ( D ) OTHER INFORMATION: /note="This position is p-C."

( x i ) SEQUENCE DESCRIPTION: SEQ ID NO:112:

| | | |
|---|---|---|
| CTTCCAGAGA | AAGAGCCTGT | 20 |

( 2 ) INFORMATION FOR SEQ ID NO:113:

( i ) SEQUENCE CHARACTERISTICS:

(A) LENGTH: 20 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(1, "")
(D) OTHER INFORMATION: /note="This position is bio-T."

(xi) SEQUENCE DESCRIPTION: SEQ ID NO:113:

TCTTTTCAGA GCCACTCACG 20

(2) INFORMATION FOR SEQ ID NO:114:

(i) SEQUENCE CHARACTERISTICS:
(A) LENGTH: 20 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(1, "")
(D) OTHER INFORMATION: /note="This position is bio-T."

(xi) SEQUENCE DESCRIPTION: SEQ ID NO:114:

TCTTTTCAGA GCCACTCACA 20

(2) INFORMATION FOR SEQ ID NO:115:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:115:

CTAACAATCA ATAAAATACA CTC 23

(2) INFORMATION FOR SEQ ID NO:116:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:116:

ATACCCAAGA AAATTCAAAA G 21

(2) INFORMATION FOR SEQ ID NO:117:

(i) SEQUENCE CHARACTERISTICS:
(A) LENGTH: 21 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(1, "")
(D) OTHER INFORMATION: /note="This position is p-A."

(xi) SEQUENCE DESCRIPTION: SEQ ID NO:117:

AGACAATTAA GAATGTGAGG T 21

(2) INFORMATION FOR SEQ ID NO:118:

(i) SEQUENCE CHARACTERISTICS:

(A) LENGTH: 25 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(1, "")
(D) OTHER INFORMATION: /note="This position is bio-A."

(xi) SEQUENCE DESCRIPTION: SEQ ID NO:118:

ATATATCTAT AATCTATATT TCTTA                    25

(2) INFORMATION FOR SEQ ID NO:119:

(i) SEQUENCE CHARACTERISTICS:
(A) LENGTH: 25 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(1, "")
(D) OTHER INFORMATION: /note="This position is bio-A."

(xi) SEQUENCE DESCRIPTION: SEQ ID NO:119:

ATATATCTAT AATCTATATT TCTTG                    25

(2) INFORMATION FOR SEQ ID NO:120:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:120:

CTTCCTCTCT TCCATATC                            18

(2) INFORMATION FOR SEQ ID NO:121:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:121:

CCCTCTATAT TAGGTTTTC                           19

(2) INFORMATION FOR SEQ ID NO:122:

(i) SEQUENCE CHARACTERISTICS:
(A) LENGTH: 25 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(1, "")
(D) OTHER INFORMATION: /note="This position is p-T."

(xi) SEQUENCE DESCRIPTION: SEQ ID NO:122:

TTTTAAAAAA TGTTTAATCT TTGTG                    25

(2) INFORMATION FOR SEQ ID NO:123:

(i) SEQUENCE CHARACTERISTICS:

```
            ( A ) LENGTH: 22 base pairs
            ( B ) TYPE: nucleic acid
            ( C ) STRANDEDNESS: single
            ( D ) TOPOLOGY: linear ( i x ) FEATURE:
            ( A ) NAME/KEY: misc_difference
            ( B ) LOCATION: replace(1, "")
            ( D ) OTHER INFORMATION: /note="This position is bio-T."

( x i ) SEQUENCE DESCRIPTION: SEQ ID NO:123:

TTGGGGATTT TATAGATTTT AT                                                22

( 2 ) INFORMATION FOR SEQ ID NO:124:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i x ) FEATURE:
            ( A ) NAME/KEY: misc_difference
            ( B ) LOCATION: replace(1, "")
            ( D ) OTHER INFORMATION: /note="This position is bio-T."

( x i ) SEQUENCE DESCRIPTION: SEQ ID NO:124:

TTGGGGATTT TATAGATTTT AG                                                22
```